(12) United States Patent
Lai et al.

(10) Patent No.: US 10,392,742 B2
(45) Date of Patent: Aug. 27, 2019

(54) BIOFINISHING SYSTEM

(71) Applicant: Novozymes A/S, Bagsvaerd (DK)

(72) Inventors: Weijian Lai, Beijing (CN); Wenqi Huang, Beijing (CN); Wei Wang, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/735,525

(22) PCT Filed: Jun. 24, 2016

(86) PCT No.: PCT/CN2016/086993
§ 371 (c)(1),
(2) Date: Dec. 11, 2017

(87) PCT Pub. No.: WO2016/206621
PCT Pub. Date: Dec. 29, 2016

(65) Prior Publication Data
US 2018/0171544 A1    Jun. 21, 2018

(30) Foreign Application Priority Data
Jun. 26, 2015   (WO) ................ PCT/CN2015/082480

(51) Int. Cl.
| | |
|---|---|
| *D06M 16/00* | (2006.01) |
| *C12N 9/42* | (2006.01) |
| *D06P 5/13* | (2006.01) |
| *D06P 5/15* | (2006.01) |
| *D06Q 1/02* | (2006.01) |
| *D06L 4/40* | (2017.01) |
| *D06M 101/06* | (2006.01) |

(52) U.S. Cl.
CPC ......... *D06M 16/003* (2013.01); *C12N 9/2437* (2013.01); *D06L 4/40* (2017.01); *D06M 16/00* (2013.01); *D06P 5/137* (2013.01); *D06P 5/158* (2013.01); *D06Q 1/02* (2013.01); *D06M 2101/06* (2013.01); *D06M 2200/50* (2013.01)

(58) Field of Classification Search
CPC .......................... D06M 16/003; D06M 16/00
See application file for complete search history.

(56) References Cited

U.S. PATENT DOCUMENTS

| | | | |
|---|---|---|---|
| 5,958,083 A | 9/1999 | Onishi et al. | |
| 7,256,032 B2 | 8/2007 | Valtakari et al. | |
| 7,741,093 B2 | 6/2010 | Vehmaanpera et al. | |
| 2007/0111278 A1 | 5/2007 | Koga et al. | |
| 2013/0143277 A1* | 6/2013 | Gutierrez ................. | C12N 1/22 435/99 |

FOREIGN PATENT DOCUMENTS

| | | |
|---|---|---|
| WO | 1996017994 A1 | 6/1996 |
| WO | 1997014804 A1 | 4/1997 |
| WO | 2007057418 A1 | 5/2007 |
| WO | 2007118935 A1 | 10/2007 |
| WO | 2009010444 A2 | 1/2009 |
| WO | 2010076388 A1 | 7/2010 |
| WO | 2012089024 A1 | 7/2012 |
| WO | 2012106824 A1 | 8/2012 |
| WO | 2013-167613 A1 | 11/2013 |

OTHER PUBLICATIONS

Aich et al., Biotechnol. Biofuels , 10:135, 1-14, 2017.*
Andersen et al, 2008, Enzyme Microb Technol 42, 362-370.
Cantarel et al, 2009, Nucl Acids Res 37, D233-238.
Cavaco Paulo et al, 1998, Carbo Poly 37, 273-277.
Cavaco-Paulo et al, 1996,Tex Chem Colorist, 28(6),28-32.
Gusakov et al, 2007, Biotechnol Bioeng 97(5), 1028-1038.
Heikinheimo et al, 2001, Textile Res J 71(8), 672-677.
Igarashi et al, 2008, Appl Environ Microbiol 74(18), 5628-563.
Oinonen et al, 2004, Enzy Microbiol Technol 34, 332-341.

* cited by examiner

*Primary Examiner* — Maryam Monshipouri
(74) *Attorney, Agent, or Firm* — Eric J. Fechter

(57) ABSTRACT

The present disclosure relates to a biofinishing system comprising a combination of cellulases, in particular a biofinishing system comprising a combination of GH45 cellulases. The present disclosure further relates to a process for treating a cellulose-containing textile comprising biofinishing the cellulose-containing textile with a combination of GH45 cellulases.

21 Claims, No Drawings
Specification includes a Sequence Listing.

BIOFINISHING SYSTEM

CROSS-REFERENCE TO RELATED APPLICATIONS

This application is a 35 U.S.C. 371 national application of international application no. PCT/CN2016/086993, filed Jun. 24, 2016, which claims priority benefit under 35 U.S.C. 119 of international application no. PCT/CN2015/082480, filed Jun. 26, 2015. The contents of these applications are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to a biofinishing system comprising a combination of celluases, in particular to a combination of cellulases for use in treating a cellulose-containing textile.

Description of the Related Art

Cellulase enzymes are widely used to improve the appearance and softness of cellulose-containing fabrics. A widespread application of cellulase enzymes is to remove cotton fuzz and loose surface fibers in or on the fabric. This process is referred to as "biopolishing" and smoothes the surface of the fabric, which in turn improves its softness and appearance. Cellulase treatment also aids in the prevention of subsequent formation of fiber pills that make the garments appear worn. During depilling it is desirable to minimize strength loss of the fabric due to the hydrolytic action of the cellulases.

Another industrial application of cellulase enzymes is for treating denim fabrics so as to impart to them a "stone-washed" appearance. Such a process is known in the industry as "biostoning". The term biostoning was adopted as pumice stones were traditionally used to treat the fabric. However, cellulases have largely replaced pumice stones in recent years. Biostoning is quite different from depilling in that biostoning aims to remove colour from denim and control its re-deposition on the fabric while depilling aims to solely improve softness and appearance as in depilling.

Cellulase enzymes are a group of glycoside hydrolase enzymes that catalyze the hydrolysis of beta-1,4-glycosidic linkages in the cellulose polymer and often comprise a cellulose binding domain (CBD) and a catalytic domain. A region between these two domains known as a "linker" or "linker peptide" serves as a flexible spacer between the CBD and the catalytic domain. The catalytic domains of individual cellulase components are classified by both the Enzyme Commission (EC) and the Glycoside Hydrolase (GH) family systems. The Enzyme Commission distinguishes two classes of cellulases based on their preference for cleavage of internal beta-1,4 linkages (endoglucanase or "EG", EC 3.2.1.4) or the release of cellobiose from the reducing or non-reducing end of the cellulose polymer (cellobiohydrolases or "CBH", EC 3.2.1.91, sometimes also referred to as exoglucanases). In contrast, the GH family system distinguishes the catalytic domains of cellulase components based on the conservation of primary and secondary structure, as well as the stereochemistry of the catalytic reaction. The GH family designations for all known cellulase catalytic and binding domains is provided and continually updated through the Carbohydrate-Active EnZymes (CAZy) database (Cantarel et al, 2009, Nucleic Acids Res 37:D233-238) available at the URL: cazy.org. Cellulase enzymes may be found in a number of GH Families including, but not limited to, Families 5, 6, 7, 8, 9, 10, 12, 16, 18, 19, 26, 44, 45, 48, 51, 61 and 74. Further, cellulase in some of the larger GH Families may be grouped into subfamilies.

A number of groups have contemplated the use of GH45 cellulases in depilling. WO 97/14804 discloses a neutral Ce145A cellulase (20 K cellulase) from *Melanocarpus* origin for use in the textile and detergent industry. WO2010/076388 discloses the production and use of *Geomyces* or *Fusarium* CelA5 endoglucanases in denim washing and depilling. U.S. Publication No. 2007/0111278 discloses the use of STCE1, a Cel45 endoglucanase, derived from *Staphylotrichum*, in washing or depilling of cellulose-containing fabrics. U.S. Pat. No. 7,741,093 discloses fusion of the *Melanocarpus* CelA5 endoglucanase to a linker peptide of *Trichoderma reesei* CBH I and a cellulose binding domain for biostoning and biofinishing. The purpose of constructing such fusion proteins was to increase the size of the *Melanocarpus* Cel45A enzyme, thereby decreasing the ability of the enzyme to penetrate the fabric, which in turn reduces strength loss. Similar approaches with Cel45 endoglucanases and other cellulase enzymes are disclosed in WO 2007/118935 and U.S. Pat. No. 7,256,032.

Other groups have focused on elucidating whether or not cellulase enzyme components synergize with one another. The identification of synergistic combinations of enzyme components that provide for enhanced depilling could be a step forward with respect to improving process economics. Such improvements may be achieved since less enzyme protein, which is costly, would be needed to impart the desired depilling effect.

Heikinheimo and Buchert (Textile Research Journal, 2001, 71 (8):672-677) investigated the depilling properties of *Trichoderma reesei* EG I and II and CBH I and II cellulase components alone and in combination. Treatment of cotton interlock fabric with EG II-based combinations with CBH I or CBH II resulted in favourable depilling properties. However, the investigators also reported decreased depilling activity for combinations of the two endoglucanases, EG I and EG II. That is, no endo-endo synergy between the cellulase components was observed.

Cavaco-Paulo and Almeida (Textile Chemist and Colorist, 1996, 28(6): 28-32) observed a high activity of EGI and II-deleted *Trichoderma reesei* cellulase mixtures on cotton cellulose. The authors state therein that the effect may possibly be due to synergy between the two CBH components or the CBH components and residual EG III or EG V. In Cavaco-Paulo, Carbohydrate Polymers, 1998, 37:273-277, it was stated that minor EG components seem to cooperate with the CBHs, in a synergistic fashion, to fully hydrolyse cotton. However, no testing was carried out to examine which particular components exhibited synergism with one another.

U.S. Pat. No. 5,958,083 discloses binary cellulase enzyme mixtures for use in biostoning. The first component is a Family 5 endoglucanase derived from *Bacillus* or *Clostridium*, or Family 7 endoglucanase derived from *Humicola insolens*. The second component is a mechanical abrading agent, and/or an abrading cellulase (to form localized variation in color density), which may be a Family 12 or a Family 45 cellulase with a cellulose binding domain.

Although improved biostoning with low backstaining was obtained, the properties of these compositions in depilling assays were not investigated.

Miettinen-Oinonen et al. (Enzyme and Microbial Technology, 2004, 34:332-341) examined the effect of Family 45 enzymes in biostoning, alone or in combination with other cellulase components, including endoglucanases. However, the depilling properties of these enzyme compositions were not tested in these studies.

WO13167613 discloses the use of combinations of GH45 cellulases and auxiliary care enzymes comprising Family 5 cellulase and/or Family 7 cellulase for biopolishing and general fabric care at low temperatures.

WO12106824 discloses a cellulase enzyme mixtures for depilling, comprising a Family 45 cellulase enzyme component and one or more additional cellulase enzyme components selected from a Family 5 cellulase, a Family 6 celluase or a bomination thereof, wherein said enzyme mixture is secreted by a genetically modified microbe overexpressing (i) a Family 45 gene encoding said Family 45 cellulase enzyme, and (ii) a gene or genes encoding the one ore more additional cellulase enzyme components selected from a Family 5 cellulase, a Family 6 celluase or a bomination thereof.

Despite these efforts, there is still need for improved combinations of cellulase enzymes and compositions thereof that are more effective in biofinishing a cellulose-containing textile. In particular, there is a continuous need for more efficient cellulase enzyme composition to improve the process economics. The present invention aims to meet these needs.

SUMMARY OF THE INVENTION

The present invention provides an enzyme composition comprising, a first polypeptide having GH45 cellulase activity and biofinishing activity, and a second polypeptide having GH45 cellulase activity and biofinishing activity.

The present invention also relates to a nucleic acid construct or expression vector comprising a first polypeptide having GH45 cellulase activity and biofinishing activity, and a second polypeptide having GH45 cellulase activity and biofinishing activity.

The present invention also relates to a recombinant host cell comprising a first polypeptide having GH45 cellulase activity and biofinishing activity, and a second polypeptide having GH45 cellulase activity and biofinishing activity.

The present invention also relates to a process for biofinishing a cellulose-containing textile comprising contacting the cellulose-containing textile with the enzyme composition or the recombinant host cell of the present invention.

The present invention also relates to a process for biofinishing a cellulose-containing textile, comprising (a) treating the cellulose-containing textile with a first polypeptide having GH45 cellulase activity and biofinishing activity; and (b) treating the cellulose-containing textile with a second polypeptide having GH45 cellulase activity and biofinishing activity.

The present invention also relates to a process for treating a cellulose-containing textile, comprising (a) desizing;
(b) color modification;
wherein a first polypeptide having GH45 cellulase activity and biofinishing activity and a second polypeptide having GH45 cellulase activity and biofinishing activity are added before, during or after step (a) and step (b).

The present invention also relates to a process for treating a cellulose-containing textile, comprising (a) desizing;
(b) scouring;
(c) bleaching;
(d) dyeing;
wherein a first polypeptide having GH45 cellulase activity and biofinishing activity and a second polypeptide having GH45 cellulase activity and biofinishing activity are added before, during or after step (a), (b), (c) or (d).

The present invention further relates to use of a first polypeptide having GH45 cellulase activity and biofinishing activity and a second polypeptide having GH45 cellulase activity and biofinishing activity for biofinishing a cellulose-containing textile.

Disclosed herein are combinations of a first GH45 cellulase and a second GH45 cellulase that are particularly effective in the biofinishing a cellulose-containing textile. The combinations of GH45 cellulase enzyme components of the present invention provide for enhanced biofinishing of cotton-containing textile relative to the biofinishing effect of the individual enzyme components. For example, the combination of a first GH45 cellulase and a second GH45 cellulase at different protein ratio delivers about 1%, about 5%, about 10%, about 15%, about 20%, about 30%, about 50% stronger biopolishing effect than the individual GH45 cellulases. The combination of a first GH45 cellulase and a second GH45 cellulase at different protein ratio delivers about 1%, about 5%, about 10%, about 15%, about 20%, about 30%, about 50% stronger biostoning effect than the individual GH45 cellulases in denim abrasion. In a pilling notes test, the combination of a first GH45 cellulase and a second GH45 cellulase at different protein ratio delivers about 0.1, about 0.2, about 0.5, about 0.8, about 1.0 pilling note more than that of the individual GH45 cellulases. The utilization of such enzyme combinations could be a step forward with respect to improving process economics. For example, the combination of a first GH45 cellulase and a second GH45 cellulase delivers an equivalent biofinishing effect with about ½, about ⅓, about ¼, about ⅕, about ⅙, about ⅛ or about 1/10 shorter time than the individual GH45 cellulases. For a high-temperature tolerant GH45 cellulase and low-temperature adapted GH45 cellulase, the combination of the GH45 cellulases delivers a stable biofinishing performance at a broad range from the high temperature to the low temperature.

DETAILED DESCRIPTION OF THE INVENTION

GH45 Cellulases

Glycoside hydrolases (GHs) are a large group of enzymes that cleave glycosidic bonds between individual carbohydrate monomers in large polysaccharide molecules. Cellulases cleave the beta 1-4 bond between glucose monomers in the cellulose polymer. GH enzymes all share one of two common mechanisms, called inverting and retaining, for introducing a water molecule at a glycosidic bond thus cleaving the polysaccharide.

The GH Family 45 cellulase enzymes (formerly Family K) act with inversion of anomeric configuration to generate the alpha-D anomer of the oligosaccharide as a product. It has been elucidated that, in the active site, one aspartic acid amino acid acts as a general acid and another as a general base.

The three dimensional structure of Family 45 enzymes has been elucidated (see, for example, the structure of

*Humicola insolens* in Davies et al, 1996, ActaCrystallographica Section D-Biological Crystallography 52: 7-17 Part 1). The enzymes contain a six-stranded beta-barrel to which a seventh strand is appended. The structure contains both parallel and anti-parallel beta-strands. The active center is located in an open substrate-binding groove.

As used herein, the term "GH45 cellulase", "Family 45 cellulase" or "Cel145" means a carbohydrate active cellulase enzyme that contains a glycoside hydrolase Family 45 catalytic domain that is classified under EC 3.2.1.4. The term encompasses a carbohydrate active enzyme that hydrolyzes cellulose and cello-oligosaccharides using an inverting mechanism, and has either of the following two signature sequences in the vicinity of the catalytic aspartic acid amino acids: (i) both a first conserved signature sequence of A/S/T-T-R/N/T-Y/F/T-X-D-X-X-X-X-X-C/A-A/G/S-W/C and a second conserved signature sequence of H/Q/D/N-F/L-D-I/L/F; or (ii) has the second conserved signature sequence of H/Q/D/N-F/L-D-I/L/F but lacks said first conserved sequence. In one embodiment, the second conserved signature sequence is H-F-D-I.

Family 45 cellulase enzymes have been divided into at least two subfamilies referred to as "A" and "B" (Igarashi et al, Applied and Environmental Microbiology, 2008, 74(18): 5628-5634). According to one embodiment of the invention, the Family 45 cellulase enzyme is a subfamily A member. According to another embodiment of the invention, the Family 45 cellulase enzyme is a subfamily B member. This includes, but is not limited to, those subfamily A and subfamily B enzymes listed in the tables below.

Family 45 Cellulase Subfamily B Members:

| Organism | Abreviated Name | GenBank Accession Noumber | SEQ ID NO: |
|---|---|---|---|
| *Trichoderma reesei* | TrCel45A | CAA83846.1 | 9 |
| *Trichomderma viride* | TvEGV | AAQ21385.1 | 10 |
| *Penicillium decumbens* | PdCel 45A | ACF33814.1 | 11 |
| *Aspergillus nidulans* | AnAN6786.2 | EAA58604.1 | 12 |
| *Hadiotis discus discus* | HddEG1 | ABO26608.1 | 13 |
| *Ampullaria crossean* | AcEG27I | ABR92637.1 | 14 |
| *Ampullaria crossean* | AcEG27II | ABR92638.1 | 15 |
| *Mytilus edulis* | MeEG | CAC59695.1 | 16 |
| *Phanerochaete chrysosporium* | PcCel45A | BAG68300.1 | 17 |

Family 45 Cellulase Subfamily A Members:

| Organism | Abreviated Name | GenBank Accession Number and WO publication Number | SEQ ID NO: herein |
|---|---|---|---|
| *Humicola insolens* | HiCel45A | AAE16508.1 | 18 |
| *Humicola grisea* var. *thermoidea* | HgEgl3 | BAA74956.1 | 19 |
| *Humicola nigrescens* | HnCel45A | CAB42308.1 | 20 |
| *Geomyces pannorum* | Gp RF6293 Cel45A | SEQ ID NO: 13 in WO2010/076388 | 21 |
| *Geomyces pannorum* | Gp RF6293 Cel45B | SEQ ID NO: 15 in WO2010/076388 | 22 |
| *Fusarium* cf. *eguiseti* | Fe RF6318 Cel45B | SEQ ID NO: 17 in WO2010/076388 | 23 |
| *Geomyces pannorum* | Gp RF6546 Cel45A | SEQ ID NO: 19 in WO2010/076388 | 24 |
| *Geomyces pannorum* | Gp RF6608 Cel45A | SEQ ID NO: 21 in WO2010/076388 | 25 |
| *Geomyces pannorum* | Gp RF6608 Cel45B | SEQ ID NO: 23 in WO2010/076388 | 26 |
| *Staphylotrichumcoccosporum* | ScSTCE1 | BAG69187.1 | 27 |
| *Staphylatrichum coccosporum* | ScSTCE1 | SEQ ID NO: 3 in WO2005/054475 | 2 |
| *Sordaria fimicola* | Sfcel45 | SEQ ID NO: 2 in WO 2014/026630 | 6 |
| *Melanocarpus albomyces* | MaCel45A | CAD56665.1 | 28 |
| *Podospora anserina* | PaCel45A | CAP61565.1 | 29 |
| *Acremonium thermophilum* | AtSEQ6 | ACE10216.1 | 30 |
| *Thielavia terrestris* | TtCel45A | SEQ. ID NO: 4 in WO 2012/089024 | 4 |
| *Trichothecium roseum* | TroCel45A | CAB42312.1 | 31 |
| *Acremonium thermophilum* | AtSEQ2 | ABW41463.1 | 32 |
| *Fusarium anguioides* | FaCel45A | CAB42310.1 | 33 |
| *Clonostachys rosea* f. *catenulata* | CrCel45A | CAB42311.1 | 34 |
| *Neurospora crassa* | NcCEl45A | CAD70529.1 | 35 |
| *Volutella colletotrichoides* | VcSEQ22 | AAY00854.1 | 36 |
| *Gibberella zeae* | GzCel45A | AAR02399.1 | 37 |
| *Fusarium oxysporum* | FoCel45A | AAA65589.1 | 38 |
| *Acremonium SP.* | AsSEQ10 | AAY00848.1 | 39 |
| *Acremonium SP.* | AsSEQ8 | AAY00847.1 | 40 |
| *Chrysosporium lucknowense* | ClCel45A | AAQ38150.1 | 41 |
| *Thielavia heterothallica* | ThSEQ2 | AAY00844.1 | 42 |
| *Mucor circinelloides* | McMce1 | BAD95808.1 | 43 |
| *Reticulitermes speratus* | RshpCel45A | BAA98037.1 | 44 |
| *Bursaphelenchus xylophilus* | BxEng1 | BAD34546.1 | 45 |
| *Botryotinia fuckeliana* | BfCel45A | XP_JX11547700.1 | 46 |
| *Acremonium thermophilum* | AtSEQ4 | ABW41464.1 | 47 |
| *Scopulariopsis brevicaulis* | SbEgl | Q7M4T4* | 48 |
| *Syncephalastrum racemosum* | SrCBHI | ABU49185.2 | 49 |
| *Rhizopus oryzae* | RoRce1 | BAC53956.1 | 50 |
| *Crinipellis scabella* | CsSEQ16 | AAY00851.1 | 51 |
| *Macrophomina phaseolina* | MpSEQ14 | AAY00850.1 | 52 |
| *Podospora anserina* | PaCel45B | CAP69443.1 | 53 |

-continued

| Organism | Abreviated Name | GenBank Accession Number and WO publication Number | SEQ ID NO: herein |
|---|---|---|---|
| *Rhizopus oryzae* | RoRce3 | BAC53988.1 | 54 |
| *Bursaphelenchus xylophilus* | BxEng2 | BAD34544.1 | 55 |
| *Bursaphelenchus xylophilus* | BxEng3 | BAD34548.1 | 56 |
| *Humicolagrisea* var. *thermoidea* | HgEgl4 | BAA74957.1 | 57 |
| *Phycomyces nitens* | PnPcel | BAD77808.1 | 58 |
| *Rhizopus oryzae* | RoRce2 | BAC53987.1 | 59 |
| *Mastotermes darwiniensis hindgut symbiont* sp. | MdhsFm4 | CAD39200.1 | 60 |
| *Magnaporthe grisea* | MgCel45A | XP_363402.1 | 61 |
| *Mastotermes darwiniensis hindgut symbiont* sp. | MdhsFm3 | CAD39199.1 | 62 |
| *Mastotermes darwiniensis hindgut symbiont* sp. | MdhsFml | CAD39197.1 | 63 |
| *Mastotermes darwiniensis hindgut symbiont* sp. | MdhsFm2 | CAD39198.1 | 64 |
| *Neurospora tetrasperma* | Ntcel45 | SEQ ID NO: 2 in WO 2015/058700 | 8 |
| *Pichia pastoris* GS115 | PpCel45A | CAY71902.1 | 65 |
| *Piromyces equi* | PeCel45A | CAB92325.1 | 66 |
| *Apriona germari* | AgCelI | AAN78326.1 | 67 |
| *Apriona germari* | AgCelII | AAR22385.1 | 68 |
| *Alternaria alternata* | AaKl | AAF05700.1 | 69 |
| *Phaedon cochleariae* | PcEg | CAA76931.1 | 70 |
| *Talaromyces emersonii* | TeCel45A | CAJ75963.1 | 71 |
| *Ustilago maydis* | UmEglI | AAB36147.1 | 72 |

*Uniprot entry

GH5 Cellulases

The amino acid sequences for over 3,000 naturally occurring Family 5 cellulases of fungal and bacterial origin have been elucidated. Regions of Family 5 cellulases are well conserved in most Family 5 cellulase enzymes and this has allowed the alignment of parts of the catalytic domains of family members.

Enzymes of Family 5 or GH5 cellulase share a common (beta/alpha)s-barrel fold and a catalytic mechanism resulting in a net retention of the anomeric sugar conformation. Glycoside hydrolase catalysis is driven by two carboxylic acids found on the side chain of aspartic acid and/or glutamic acid. These two amino acids are highly conserved among family members.

GH6 Cellulase

Family 6 cellulases comprise two aspartic acid (D) amino acids which may serve as catalytic amino acids. These aspartic acid amino acids are found at positions 175 and 221, as determined by alignment with a wild-type *Trichoderma reesei* enzyme. Most of the Family 6 cellulases identified thus far are mesophilic; however, this family also includes thermostable cellulases from *Thermobifida fusca* (TfCel6A and TfCel6B) and the alkalophilic cellulases from *Humicola insolens* (HiCel6A and HiCel6B). Family 6 cellulases also share a similar three dimensional structure: an alpha/beta-barrel with a central beta-barrel containing seven parallel beta-strands connected by five alpha-helices. The three dimensional structures of several Family 6 cellulases are known, such as TrCel6A, *Thermobifida fusca* endo-beta-I,4-glucanase Cel6A, *Humicola insolens* cellobiohydrolase Cel6A, *Humicola insolens* endo-beta-I,A-glucanase Cel16B and *Mycobacterium tuberculosis* H37Rv Cel6A.

As used herein, the term "GH6 cellulase", "Family 6 cellulase" or "Cel16" encompasses a carbohydrate active cellulase enzyme that contains aglycohydrolase (GH) Family 6 catalytic domain that is classified under EC 3.2.1.91 or EC 3.2.1.4.

GH 7 Celllulase

Family 7 cellulase or GH7 cellulase includes endo-beta-1,4-glucanase (EC 3.2.1.4); reducing end-acting cellobiohydrolase (EC 3.2.1.176); chitosanase (EC 3.2.1.132); endo-beta-1,3-1,4-glucanase (EC 3.2.1.73). These enzymes were formerly known as cellulase family C.

Endoglucanase

The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMG) as substrate according to the procedure of Ghose, 1987, *Pure and Appl. Chem.* 59: 257-268, at pH 5, 40° C.

Sources of Cellulase

A polypeptide having cellulase activity, including GH45 cellulase activity, GH5 cellulase activity, GH6 cellulase, or GH7 cellulase activity, of the present invention may be obtained from microorganisms or plants or animals of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* polypeptide having cellulase activity, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another aspect, the polypeptide is a *Streptococcus equisimilis, Streptococcus pyogenes, Streptococcus uberis,* or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus,* or *Streptomyces lividans* polypeptide.

The polypeptide may be a fungal polypeptide. For example, the polypeptide may be a yeast polypeptide such as a *Candida, Kluyveromyces, Pichia, Saccharomyces, Schizosaccharomyces,* or *Yarrowia* polypeptide; or a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Sordaria, Staphylotrichum, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awarnori, Aspergillus foelidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusariurn grarninum, Fusarium heterosporum, Fusarium negundi, Fusarium oxysporum, Fusarium reticulatum, Fusarium roseum, Fusarium sambucinum, Fusarium sarcochrourn, Fusarium sporotrichioides, Fusarium sulphureum, Fusarium torulosum, Fusariurn trichothecioides, Fusarium venenalum, Humicola grisea, Humicola insolens, Humicola lanuginosa, Irpex lacteus, Mucor miehei, Myceliophthora thermophila, Neurospora crassa, Neurospora tetrasperma, Penicillium funiculosum, Penicillium purpurogenum, Phanerochaete chrysosporium, Sordaria fimicola, Staphylotrichum coccosporum, Thielavia achrornatica, Thielavia albomyces, Thielavia athopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

In an preferable embodiment, the polypeptide having GH45 cellulase activity and biofinishing activity has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 2, the mature polypeptide of SEQ ID NO: 4, the mature polypeptide of SEQ ID NO: 6 or the mature polypeptide of SEQ ID NO: 8 of the present invention.

In one aspect, the mature polypeptide of SEQ ID NO: 4 is amino acids 22-299 of SEQ ID NO: 4; the mature polypeptide of SEQ ID NO: 6 is amino acids 22 to 294 of SEQ ID NO: 6; and the mature polypeptide of SEQ ID NO: 8 is amino acids 22-293 of SEQ ID NO: 8 of the present invention.

In a further preferable embodiment, a polynucleotide encoding a polypeptide having GH45 cellulase activity and biofinishing activity has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to nucleotides 64-948 of SEQ ID NO: 1 (i.e., nucleotides 64-948 of SEQ ID NO: 2 in WO2005/054475), the mature polypeptide coding sequence of SEQ ID NO: 3 (i.e., the mature polypeptide coding sequence of SEQ ID NO: 3 in WO2012/089024), the mature polypeptide coding sequence of SEQ ID NO: 5 (i.e., the mature polypeptide coding sequence of SEQ ID NO: 1 in WO2014/026630) or the mature polypeptide coding sequence of SEQ ID NO: 7 (i.e., the mature polypeptide coding sequence of SEQ ID NO: 1 in WO2015/058700) of the present invention.

In the present invention, the polypeptide having the cellulase activity, including GH45 cellulase activity, GH5 cellulase activity, GH6 cellulase activity, or GH7 cellulase activity can a naturally-occurring or wild-type cellulase or a modified cellulase. Preferably, amino acid modifications (i.e. substitution, deletion, and/or insertion of one or more (or several) amino acids) are of a minor nature, that is conservative amino acid substitutions or insertions that do not significantly affect the folding and/or activity of the protein; small deletions, typically of one to about 30 amino acids; small amino or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer. 1988, Science 241: 53-57; Bowie and Sauer, 1989, Proc. Natl. Acad. Sci. USA 86: 2152-2156; WO 95/17413; or WO 95/22625. Other methods that can be used include error-prone FOR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Preferably, the total number of amino acid substitutions, deletions and/or insertions of the polypeptide of SEQ ID NO: 2, the mature polypeptide of SEQ ID NO: 4, the mature polypeptide of SEQ ID NO: 6, or the mature polypeptide of SEQ ID NO: 8, is not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Measurement of the Biofinishing Activity of the Enzyme Composition

In order to determine the specific biofinishing activity of the cellulase components in isolation and in combination, they are typically purified using known techniques.

The term "biofinishing" as used herein refers to the treatment of a textile using cellulases and includes, but not limited to, biopolishing and biostoning.

The "biofinishing activity", especially "biopolishing activity", as used herein, is determined as set forth in Examples. The biopolishing effectiveness of the first GH45 cellulase in combination with the second GH45 cellulase and the respective individual cellulase components can be measured by the activity in removing fuzz, or small balls of fuzz (referred to as pills), from fabric. The depilling can be expressed as the depilling activity per unit of protein (i.e., specific depilling activity).

According to one embodiment of the invention, the first GH45 cellulase enzyme component and the second GH45 cellulase component are present in an enzyme composition that exhibits synergy in an assay that measures biofinishing activity. Preferably, the assay is a pilling note test for biopolishing activity. The combinations of GH45 cellulase enzyme components of the present invention provide for enhanced biofinishing of a cotton-containing textile relative to the biofinishing effect of the individual enzyme components. For example, the combination of a first GH45 cellulase and a second GH45 cellulase delivers about 1%, about 5%, about 10%, about 15%, about 20%, about 30%, about 50% stronger biopolishing effect than the individual GH45 cellulases. The combination of a first GH45 cellulase and a second GH45 cellulase delivers about 1%, about 5%, about 10%, about 15%, about 20%, about 30%, about 50% stronger biostoning effect than the individual GH45 cellulases in denim abrasion. In a pilling notes test, the combination of a first GH45 cellulase and a second GH45 cellulase delivers about 0.1, about 0.2, about 0.5, about 0.8, about 1.0 pilling note more than that of the individual GH45 cellulases. The utilization of such enzyme combinations could be a step forward with respect to improving process economics. For example, the combination of a first GH45 cellulase and a second GH45 cellulase delivers an equivalent biofinishing effect with about ½, about ⅓, about ¼, about ⅕, about ⅙, about ⅛ or about ¹⁄₁₀ shorter time than the individual GH45 cellulases. For a high-temperature tolerant GH45 cellulase and low-temperature adapted GH45 cellulase, the combination of the GH45 cellulases delivers a stable biofinishing performance, including but not limited to biopolishing and biostoning performance, at a broad range from the high temperature to the low temperature.

Nucleic Add Constructs

The present invention also relates to nucleic acid constructs comprising a polynucleotide encoding a first polypeptide having GH45 cellulase activity and biofinishing activity, and a polynucleotide encoding a second polypeptide having GH45 cellulase activity and biofinishing activity, operably linked to one or more control sequences that direct the expression of the coding sequence in a suitable host cell under conditions compatible with the control sequences.

In an embodiment, the present invention relates to nucleic acid constructs comprising a first nucleic acid construct and a second nucleic acid construct, wherein the first nucleic acid construct comprises a polynucleotide encoding a first polypeptide having GH45 cellulase activity and biofinishing activity, operably linked to one or more control sequences that direct the expression of the coding sequence in a suitable host cell under conditions compatible with the control sequences; and the second nucleic acid construct comprises a polynucleotide encoding a second polypeptide having GH45 cellulase activity and biofinishing activity, operably linked to one or more control sequences that direct the expression of the coding sequence in a suitable host cell under conditions compatible with the control sequences.

The polynucleotide may be manipulated in a variety of ways to provide for expression of the GH45 cellulases. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* those phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GALA), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos at al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus*

*subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide encoding a first polypeptide having GH45 cellulase activity and biofinishing activity, and a polynucleotide encoding a second polypeptide having GH45 cellulase activity and biofinishing activity, a promoter, and transcriptional and translational stop signals.

In an embodiment, the present invention relates to recombinant host cells, comprising a first nucleic acid construct or expression vector encoding a first polypeptide having GH45 cellulase activity and biofinishing activity; and a second nucleic acid construct or expression vector encoding a second polypeptide having GH45 cellulase activity and biofinishing activity. In a further embodiment, the present invention relates to recombinant expression vectors comprising a first recombinant expression vector and a second recombinant expression vector, wherein the first recombinant expression vector comprises a polynucleotide encoding a first polypeptide having GH45 cellulase activity and biofinishing activity, a promoter, and transcriptional and translational stop signals; and the second recombinant expression vector comprising a polynucleotide encoding a second polypeptide having GH45 cellulase activity and biofinishing activity, a promoter, and transcriptional and translational stop signals.

The various nucleotide and control sequences may be joined together to produce a recombinant expression vector that may include one or more convenient restriction sites to allow for insertion or substitution of the polynucleotide encoding the GH45 cellulases at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a first polypeptide having GH45 cellulase activity and biofinishing activity, and a second polypeptide having GH45 cellulase activity and biofinishing activity of the present invention, operably linked to one or more control sequences that direct the production of polypeptides of the present invention.

In an embodiment, the present invention relates to recombinant host cells comprising a first recombinant host cell and a second recombinant host cell, wherein the first recombinant host cell comprises a polynucleotide encoding a first polypeptide having GH45 cellulase activity and biofinishing activity, operably linked to one or more control sequences that direct the production of the polypeptide; and the second recombinant host cell comprises a second polypeptide having GH45 cellulase activity and biofinishing activity, operably linked to one or more control sequences that direct the production of the polypeptide.

In an embodiment, the polynucleotide encoding a first polypeptide having GH45 cellulase activity and biofinishing activity and the second polypeptide having GH45 cellulase activity and biofinishing activity are heterologous to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see. e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Can and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45:

409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusariurn sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Biol Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson. J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a composition comprising a first polypeptide having GH45 cellulase activity and biofinishing activity, and a second polypeptide having GH45 cellulase activity and biofinishing activity, comprising (a) cultivating a recombinant host cell comprising a polynucleotide encoding a first polypeptide having GH45 cellulase activity and biofinishing activity, and a second polypeptide having GH45 cellulase activity and biofinishing activity under conditions conducive for production of the polypeptides; and optionally, (b) recovering the composition.

The present invention further relates to methods of producing a composition comprising a first polypeptide having GH45 cellulase activity and biofinishing activity, and a second polypeptide having GH45 cellulase activity and biofinishing activity, comprising (a) cultivating a recombinant host cell comprising a first recombinant host cell and a second recombinant host cell of the present invention under conditions conducive for production of the polypeptides; and optionally, (b) recovering the polypeptides and combining the first polypeptide and the second polypeptide.

The present invention further relates to methods of producing a composition comprising a first polypeptide having GH45 cellulase activity and biofinishing activity, and a second polypeptide having GH45 cellulase activity and biofinishing activity, comprising (a) cultivating a first recombinant host cell of the present invention under conditions conducive for production of the polypeptides and cultivating a second recombinant host cell of the present invention under conditions conducive for production of the polypeptides; and optionally, (b) recovering the polypeptides and combining the first polypeptide and the second polypeptide.

The present invention further relates to methods of producing a composition comprising a first polypeptide having GH45 cellulase activity and biofinishing activity, and a second polypeptide having GH45 cellulase activity and biofinishing activity, comprising (a) cultivating a recombinant host cell comprising a polynucleotide encoding a first polypeptide having GH45 cellulase activity and biofinishing activity, and a polynucleotide encoding a second polypeptide having GH45 cellulase activity and biofinishing activity under conditions conducive for production of the polypeptides; and optionally, (b) recovering the composition.

The host cells are cultivated in a nutrient medium suitable for production of the polypeptides using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the polypeptides to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for a polypeptide. These detection methods include, but are not limited to, use of specific antibodies, formation of an enzyme product, or disappearance of an enzyme substrate. For example, an enzyme assay may be used to determine the activity of the composition.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the composition is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptides are not recovered, but rather a combination of a first host cell of the present invention expressing the first polypeptide having GH45 cellulase activity and biofinishing activity and a second host cell of the present invention expressing the second polypeptide having GH45 cellulase activity and biofinishing activity used as a source of the composition. In another embodiment, a host cell of the present invention expressing the first polypeptide and the second polypeptide is used as a source of the composition.

In an alternative aspect, the polypeptides are not recovered, but rather a combination of a first fermentation broth formulation of the present invention comprising the first polypeptide having GH45 cellulase activity and biofinishing activity and a second fermentation broth formulation of the present invention comprising the second polypeptide having GH45 cellulase activity and biofinishing activity used as a source of the composition. In another embodiment, a fermentation broth formulation of the present invention comprising the first polypeptide having GH45 cellulase activity and biofinishing activity and the second polypeptide having GH45 cellulase activity and biofinishing activity is used as a source of the composition.

Fermentation Broth Formulations or Cell Compositions

The present invention also relates to a fermentation broth formulation or a cell composition comprising a first polypeptide having GH45 cellulase activity and a second polypeptide having GH45 cellulase activity of the present invention.

The present invention further relates to a fermentation broth formulation or a cell composition comprising a first fermentation broth formulation or a cell composition and a second fermentation broth formulation or a cell composition, wherein the first fermentation broth formulation or a cell composition comprises a first polypeptide having GH45 cellulase activity and biofinishing activity, and the second fermentation broth formulation or a cell composition comprises a second polypeptide having GH45 cellulase activity and biofinishing activity.

The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Composition

In the present invention, the enzyme composition comprises or consists of a first polypeptide having GH45 cellulase activity and biofinishing activity, and a second polypeptide having GH45 cellulase activity and biofinishing activity. In one embodiment of the present invention, the first polypeptide and the second polypeptide exhibit synergy in an assay that measures biofinishing activity.

In a preferable embodiment, the assay that measures biofinishing activity is a pilling note test for biopolishing activity. In another preferable embodiment, the first GH45 cellulase and the second GH45 cellulase deliver about 1%, about 5%, about 10%, about 15%, about 20%, about 30%, about 50% stronger biopolishing effect than the individual GH45 cellulases.

In a preferable embodiment, the biofinishing activity is a biostoning activity. In another preferable embodiment, the first GH45 cellulase and the second GH45 cellulase deliver about 1%, about 5%, about 10%, about 15%, about 20%, about 30%, about 50% stronger biostoning effect than the individual GH45 cellulases in denim abrasion.

In the enzyme composition of the present invention, the first polypeptide having GH45 cellulase activity and biofinishing activity and the second polypeptide having GH45 cellulase activity and biofinishing activity are different polypeptides. In another embodiment of the present invention, the first GH45 cellulase is a high-temperature tolerant GH45 cellulase, and the second GH45 cellulase is a low-temperature adapted GH45 cellulase.

In another embodiment of the present invention, the enzyme composition further comprises a polypeptide having GH5 cellulase activity, a polypeptide having a GH6 cellulase activity and/or a polypeptide having GH7 cellulase activity.

Preferably, the enzyme compositions are enriched in such polypeptides having GH45 cellulases activity and biofinishing activity. The term "enriched" indicates that the polypeptides having GH45 cellulase activity and biofinishing activity of the composition has been increased, e.g., with an enrichment factor of at least 1.1.

In an embodiment, the first polypeptide is in an amount of from about 5% to 1000%, preferably, from about 20% to about 500%, more preferably, from about 30% to about 330%, even more preferably from about 40 to about 250%, by weight of the second polypeptide.

The enzyme compositions may be prepared in accordance with the methods of the presentation and may be in the form of a liquid or a dry composition. The compositions may be stabilized in accordance with methods known in the art.

Examples are given below of preferred uses of the enzyme compositions of the present invention. The dosage of the enzyme composition and other conditions under which the enzyme composition is used may be determined on the basis of methods known in the art.

Textile

As used herein, the term "textile" refers to fibers, yarns, fabrics, garments, and non-wovens. The term encompasses textiles made from natural, synthetic (e.g., manufactured), and various natural and synthetic blends. Textiles may be unprocessed or processed fibers, yarns, woven or knit fabrics, non-wovens, and garments and may be made using a variety of materials, some of which are mentioned, herein.

The process of the invention is most beneficially applied o a cellulose-containing textile, such as cotton, viscose, rayon, ramie, linen, Tencel, or mixtures thereof, or mixtures of any of these fibres, or mixtures of any of these fibres together with synthetic fibres such as mixtures of cotton and spandex (stretch-denim). In particular, the fabric is dyed fabric. In an embodiment, the fabric is denim. The denim fabric may be dyed with vat dyes such as indigo, or indigo-related dyes such as thioindigo.

In an embodiment of the process of the invention, a cellulose-containing textile is a cotton-containing textile or a man-made cellulose-containing textile.

Textile Manufacturing Process

The processing of a fabric, such as of a cellulosic material, into material ready for garment manufacture involves several steps: spinning of the fiber into a yarn; construction of woven or knit fabric from the yarn; and subsequent preparation processes, dyeing/printing and finishing operations. Preparation processes are necessary for removing natural and man-induced impurities from fibers and for improving their aesthetic appearance and processability prior to for instance dyeing/printing and finishing. Common preparation processes comprise desizing (for woven goods), scouring, and bleaching, which produce a fabric suitable for dyeing or finishing.

Woven fabric is constructed by weaving "filling" or "weft" yarns between warp yarns stretched in the longitudinal direction on the loom. The warp yarns must be sized before weaving in order to lubricate and protect them from abrasion at the high speed insertion of the filling yarns during weaving. Common size agents are starches (or starch derivatives and modified starches), poly(vinyl alcohol), carboxyl methyl cellulose (i.e. CMC) where starches are dominant. Paraffin, acrylic binders and variety of lubricants are often included in the size mix. The filling yarn can be woven through the warp yarns in a "over one—under the next" fashion (plain weave) or by "over one—under two" (twill) or any other myriad of permutations. Generally, dresses, shirts, pants, sheeting's, towels, draperies, etc. are produced from woven fabric. After the fabric is made, size on the fabric must be removed again (i.e. desizing).

Knitting is forming a fabric by joining together interlocking loops of yarn. As opposed to weaving, which is constructed from two types of yarn and has many "ends", knitted fabric is produced from a single continuous strand of yarn. As with weaving, there are many different ways to loop yarn together and the final fabric properties are dependent both upon the yarn and the type of knit. Underwear, sweaters, socks, sport shirts, sweat shirts, etc. are derived from knit fabrics.

Desizing

Desizing is the degradation and/or removal of sizing compounds from warp yarns in a woven fabric. Starch is usually removed by an enzymatic desizing procedure. In addition, oxidative desizing and chemical desizing with acids or bases are sometimes used.

In some embodiments, the desizing enzyme is an amylolytic enzyme, such as an alpha-amylase, a beta-amylase, a mannanase, a glucoamylase, or a combination thereof.

Suitable alpha and beta-amylases include those of bacterial or fungal origin, as well as chemically or genetically modified mutants and variants of such amylases. Suitable alpha-amylases include alpha-amylases obtainable from *Bacillus* species. Suitable commercial amylases include but are not limited to OPTISIZE® NEXT, OPTISIZE® FLEX and OPTISIZE® COOL (all from Genencor International Inc.), and DURAMYL™, ERMAMYL™, FUNGAMYL™ TERMAMYL™, AQUAZYME™ and BAN™ (all available from Novozymes A/S, Bagsvaerd, Denmark).

Other suitable amylolytic enzymes include the CGTases (cyclodextrin glucanotransferases, EC 2.4.1.19), e.g., those obtained from species of *Bacillus, Thermoanaerobactor* or *Thermeanaero*-bacterium.

Scouring

Scouring is used to remove impurities from the fibers, to swell the fibers and to remove seed coat. It is one of the most critical steps. The main purposes of scouring is to a) uniformly clean the fabric, b) soften the motes and other trashes, c) improve fabric absorbency, d) saponify and solubilize fats, oils, and waxes, and e) minimize immature cotton. Sodium hydroxide scouring at about boiling temperature is the accepted treatment for 100% cotton, while calcium hydroxide and sodium carbonate are less frequently used. Synthetic fibers are scoured at much milder conditions. Surfactant and chelating agents are essential for alkaline scouring. Enzymatic scouring has been introduced, wherein cellulase, hemicellulase, pectinase, lipase, and protease are all reported to have scouring effects.

Bleaching

Bleaching is the destruction of pigmented color and/or colored impurities as well as seed coat fragment removal. Bleaching is performed by the use of oxidizing or reducing chemistry. Oxidizing agents can be further subdivided into those that employ or generate: a) hypochlorite ($OCl^-$), b) chloride dioxide ($ClO_2$), c) permanganate ($MnO_4-$), d) ozone, and hydroperoxide species ($OOH^-$ and/or $OOH$). Reducing agents are typical sulfur dioxide, hydrosulfite salts, etc. Enzymatic bleaching using glucose oxidase or peroxidase (for example, see WO 2013/040991) has been reported. Traditionally, hydrogen peroxide is used in this process.

Printing and Dyeing

Printing and dyeing of textiles is carried out by applying dyes to the textile by any appropriate method for binding the dyestuff to the fibres in the textiles. The dyeing of textiles may for example be carried out by passing the fabric through a concentrated solution of dye, followed by storage of the wet fabric in a vapour tight enclosure to permit time for diffusion and reaction of the dye with the fabric substrate prior to rinsing off un-reacted dye. Alternatively, the dye may be fixed by subsequent steaming of the textile prior to rinsing. The dyes include synthetic and natural dyes. Typical dyes are those with anionic functional groups (e.g. acid dyes, direct dyes, Mordant dyes and reactive dyes), those with cationic groups (e.g. basic dyes), those requiring chemical reaction before application (e.g. vat dyes, sulphur dyes and azoic dyes), disperse dyes and solvent dyes.

Excess soluble dyestuff not bound to the fibres must be removed after dyeing to ensure fastness of the dyed textiles and to prevent unwanted dye transfer during laundering of the textiles by the consumer. Generally, a large amount of water is required for complete removal of excess dye. In a conventional process, the printed or dyed textile is first rinsed with cold water, then washed at high temperature with the addition of a suitable additive to decrease back-staining, like polyvinylpyrrolidone) (PVP).

An enzymatic process for removal of excess dye from dyed fabric with a rinse liquor comprising at least one peroxidase, an oxidase agent and at least one mediator, such as liquor comprising a peroxidase, hydrogen peroxidise and a mediator like 1-hydroxy-benzotriazole is disclosed in WO99/34054.

Biopolishing

Most cotton fabrics and cotton blend fabrics have a hand-feeling problem that is rather hard and stiff without the application of finishing components. The fabric surface also is not smooth because small fuzzy microfibrils protrude from it. In addition, after a relatively short period of wear, pilling appears on the fabric surface thereby giving it an unappealing, worn look.

Biopolishing is a method to treat cellulosic fabrics during their manufacture by enzymes such as cellulases, which improves fabric quality with respect to "reduced pilling formation". The most important effects of biopolishing can be characterized by less fuzz and pilling, increased gloss/luster, improved fabric handle, increased durable softness and/or improved water absorbency. Biopolishing usually takes place in the wet processing of the manufacture of knitted and woven fabrics or garments. Wet processing comprises such steps as e.g., desizing, scouring, bleaching, washing, dying/printing and finishing. Biopolishing could be performed as a separate step after any of the wetting steps or in combination with any of those wetting steps.

In the present invention, the step of biofinishing is carried out before, during or after step of desizing, bleaching, or printing and dyeing.

Manufacturing of Denim Fabric

Some dyed fabric such as denim fabric, requires that the yarns are dyed before weaving. For denim fabric, the warp yarns are dyed for example with indigo, and sized, before weaving. Preferably the dyeing of the denim yarn is a ring-dyeing. A preferred embodiment of the invention is ring-dyeing of the yarn with a vat dye such as indigo, or an indigo-related dye such as thioindigo, or a sulfur dye, or a direct dye, or a reactive dye, or a naphthol. The yarn may also be dyed with more than one dye, e.g., first with a sulphur dye and then with a vat dye, or vice versa.

Preferably, the yarns undergo scouring and/or bleaching before they are dyed, in order to achieve higher quality of denim fabric. In general, after woven into dyed fabric, such as denim, the dyed fabric or garment proceeds to a desizing stage, preferably followed by a stoning or abrasion step and/or a color modification step.

The desizing process as used herein is the same process as mentioned above in the text.

After desizing, the dyed fabric undergoes a biostoning step. The biostoning step can be performed with enzymes or pumice stories or both. As used herein, the term "biostoning", "stone washing" and "abrasion" are interchangeable, which means agitating the denim in an aqueous medium containing a mechanical abrasion agent such as pumice, an abrading cellulase or a combination of these, to provide a "stone-washed" look. In all cases, mechanical action is needed to remove the dye, and the treatment is usually carried out in washing machines, like drum washers, belly washers. As a result of uneven dye removal there are contrasts between dyed areas and areas from which dye has been removed. Treatment with cellulase can completely replace treatment with pumice stones. However, cellulase treatment can also be combined with pumice stone treatment, when it is desired to produce a heavily abraded finish. For denim manufacture, "biofinishing" includes "biostoning".

Preferably, the abrasion is followed by a color modification step. As used herein, the terms "color modification" or "color adjustment" are used without distinction to refer to any change to the color of a textile resulting from the destruction, modification, or removal of a dyestuff associated with the textile. Without being limited to a theory, it is proposed that color modification results from the modification of chromophores associated with a textile material, thereby changing its visual appearance. The chromophores may be naturally-associated with the material used to manufacture a textile (e.g., the white color of cotton) or associated with special finishes, such as dying or printing. Color modification encompasses chemical modification to a chromophore as well as chemical modification to the material to which a chromophore is attached.

Getting faded or bleached look in certain areas on textile especially denim, is an important part in textile manufacturing. This is normally achieved by applying $KMnO_4$ (or $KMnO_4/H_3PO_4$) solution (via brushing, rubbing or spray) onto dried denim after abrasion step. The stained area would get bleached after drying and washing with $Na_2S_2O_5$ solution. During this process indigo/sulphur dyes are destroyed by $KMnO_4$ through oxidation, and then $Na_2S_2O_5$ washing is applied to get rid of the brown colour caused by products of the oxidation. Such treatment will form a local color modification, i.e. a specific bleached pattern on denim to meet the customers' needs. In the present invention, the step of biofinishing is carried out before, during or after step of desizing, or color modification.

The invention is further defined in the following paragraphs:

[1]. An enzyme composition comprising, a first polypeptide having GH45 cellulase activity and biofinishing activity, and a second polypeptide having GH45 cellulase activity and biofinishing activity.

[2]. The enzyme composition of paragraph 1, wherein the first polypeptide and the second polypeptide exhibits synergy in an assay that measures biofinishing activity.

[3]. The enzyme composition of paragraph 1 or 2, wherein the assay is a pilling note test for biopolishing activity.

[4]. The enzyme composition of paragraph 3, wherein the first GH45 cellulase and the second GH45 cellulase deliver about 1%, about 5%, about 10%, about 15%, about 20%, about 30%, about 50% stronger biopolishing effect than the individual GH45 cellulases.

[5]. The enzyme composition of paragraph 1 or 2, wherein the first GH45 cellulase and the second GH45 cellulase deliver about 1%, about 5%, about 10%, about 15%, about 20%, about 30%, about 50% stronger biostoning effect than the individual GH45 cellulases in denim abrasion.

[6]. The enzyme composition of paragraph 1 or 2, wherein the first GH45 cellulase is a high-temperature tolerant GH45 cellulase, and the second GH45 cellulase is a low-temperature adapted GH45 cellulase.

[7]. The enzyme composition of any of paragraphs 1-6, wherein the first polypeptide and the second polypeptide are endoglucanases.

[8]. The enzyme composition of any of paragraphs 1-7, wherein the first polypeptide and the second polypeptides are GH45 cellulase subfamily A members.

[9]. The enzyme composition of any of paragraphs 1-8, wherein the first polypeptide is in an amount of from about 5% to 1000%, preferably, from about 20% to about 500%, more preferably, from about 30% to about 330%, even more preferably from about 40 to about 250%, by weight of the second polypeptide.

[10]. The enzyme composition of any of paragraphs 1-9, further comprising a polypeptide having GH5 cellulase activity, a polypeptide having a GH6 cellulase activity and/or a polypeptide having GH7 cellulase activity.

[11]. The enzyme composition of any of paragraphs 1-10, wherein the first polypeptide or the second polypeptide is derived from the group consisting of *Staphylotrichum, Thielavia, Sordaria* or *Neurospora*.

[12]. The enzyme composition of any of paragraphs 1-11, wherein the first polypeptide or the second polypeptide is derived from the group consisting of *Staphylotrichum coccosporum, Thielavia terrestris, Sordaria fimicola* or *Neurospora tetrasperma*.

[13]. The enzyme composition of any paragraphs 1-12, wherein the first polypeptide or the second polypeptide has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 2, the mature polypeptide of SEQ ID NO: 4, the mature polypeptide of SEQ ID NO: 6 or the mature polypeptide of SEQ ID NO: 8.

[14]. The enzyme composition of paragraph 13 wherein the first polypeptide or the second polypeptide comprises or consists of SEQ ID NO: 2, the mature polypeptide of SEQ ID NO: 4, the mature polypeptide of SEQ ID NO: 6 or the mature polypeptide of SEQ ID NO: 8.

[15]. The enzyme composition of any of paragraphs 1-14, wherein the first polypeptide or the second polypeptide is encoded by a polynucleotide sequence having at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 1, SEQ ID NO: 3, SEQ ID NO: 5 or SEQ ID NO: 7.

[16]. A nucleic acid construct or expression vector comprising a first polynucleotide encoding a first polypeptide having GH45 cellulase activity and biofinishing activity, and a second polynucleotide encoding a second polypeptide having GH45 cellulase activity and biofinishing activity, operably linked to one or more control sequences that direct the production of the polypeptides in an expression host.

[17]. The nucleic acid construct or expression vector of paragraph 16, wherein the first polypeptide or the second polypeptide is derived from the group consisting of *Staphylotrichum, Thielavia, Sordaria* or *Neurospora*.

[18]. The nucleic acid construct or expression vector of paragraph 17, wherein the first polypeptide or the second polypeptide is derived from the group consisting of *Staphylotrichum coccosporum, Thielavia terrestris, Sordaria fimicola* or *Neurospora tetrasperma*.

[19]. The nucleic acid construct or expression vector any of paragraph 16-18, wherein the first polypeptide or the second polypeptide has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 2, the mature polypeptide of SEQ ID NO: 4, the mature polypeptide of SEQ ID NO: 6 or the mature polypeptide of SEQ ID NO: 8.

[20]. The nucleic acid construct or expression vector of paragraph 19, wherein the first polypeptide or the second polypeptide comprises or consists of SEQ ID NO: 2, the mature polypeptide of SEQ ID NO: 4, the mature polypeptide of SEQ ID NO: 6 or the mature polypeptide of SEQ ID NO: 8.

[21]. The nucleic acid construct or expression vector of any of paragraph 16-20, wherein the first polynucleotide or the second polynucleotide has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 1, SEQ ID NO: 3, SEQ ID NO: 5 or SEQ ID NO: 7.

[22]. A recombinant host cell comprising the nucleic acid construct or expression vector of any of paragraphs 16-21.

[23]. The recombinant host cell of paragraph 22, comprising a first nucleic acid construct or expression vector encoding a first polypeptide having GH45 cellulase activity and biofinishing activity; and a second nucleic acid construct or expression vector encoding a second polypeptide having GH45 cellulase activity and biofinishing activity.

[24] A method of producing a composition comprising a first polypeptide having GH45 cellulase activity and a second polypeptide having GH45 cellulase activity, comprising (a) cultivating a recombinant host cell of paragraph 22 under conditions conducive for production of the polypeptides; and optionally, (b) recovering the composition.

[25]. A method of producing a composition comprising a first polypeptide having GH45 cellulase activity and a second polypeptide having GH45 cellulase activity, comprising comprising (a) cultivating a first recombinant host cell comprising the first polypeptide under conditions conducive for production of the polypeptide and cultivating a second recombinant host cell comprising the second polypeptide under conditions conducive for production of the polypeptide; and optionally, (b) recovering the polypeptides and combining the first polypeptide and the second polypeptide.

[26]. A process for biofinishing a cellulose-containing textile, comprising contacting the cellulose-containing textile with the composition of any of paragraphs 1-15 or the recombinant host cell of paragraph 22.

[27]. The process of paragraph 26, wherein the cellulose-containing textile is cotton-containing textile or man-made cellulose-containing textile.

[28]. A process for biofinishing a cellulose-containing textile, comprising.
(a) treating the cellulose-containing textile with a first polypeptide having GH45 cellulase activity and biofinishing activity; and
(b) treating the cellulose-containing textile with a second polypeptide having GH45 cellulase activity and biofinishing activity.

[29]. The process of paragraph 28, wherein the first polypeptide and the second polypeptide exhibits synergy in an assay that measures biofinishing activity.

[30]. The process of paragraph 28 or 29, wherein the first polypeptide and the second polypeptide are endoglucanases or GH45 cellulase subfamily A members.

[31]. The process of any of paragraphs 28-30, wherein the first polypeptide is in an amount of from about 5% to 1000%, preferably, from about 20% to about 500%, more preferably, from about 30% to about 330%, even more preferably from about 40 to about 250%, by weight of the second polypeptide.

[32]. The process of any of paragraphs 28-31, further comprising a GH5 cellulase, GH6 cellulase and/or GH7 cellulase.

[33]. The process of any of paragraphs 28-32, wherein the first polypeptide or the second polypeptide is derived from the group consisting of *Staphylotrichum*, *Thielavia*, *Sordaria* or *Neurospora*.

[34]. The process of paragraph 33 wherein the first polypeptide or the second polypeptide is derived from the group consisting of *Staphylotrichum coccosporum, Thielavia terrestris, Sordaria fimicola* or *Neurospora tetrasperma*.

[35]. The process of any paragraphs 28-34, wherein the first polypeptide or the second polypeptide has at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 2, the mature polypeptide of SEQ ID NO: 4, the mature polypeptide of SEQ ID NO: 6 or the mature polypeptide of SEQ ID NO: 8.

[36]. The process of paragraphs 35, wherein the first polypeptide or the second polypeptide comprises or consists of SEQ ID NO: 2, the mature polypeptide of SEQ ID NO: 4, the mature polypeptide of SEQ ID NO: 6 or the mature polypeptide of SEQ ID NO: 8.

[37]. The process of any of paragraphs 28-36, wherein the first polypeptide or the second polypeptide is encoded by a polynucleotide sequence having at least 60%, at least 70%, at least 80%, at least 85%, at least 90%, at least 91%, at least 92%, at least 93%, at least 94%, at least 95%, at least 96%, at least 97%, at least 98%, at least 99% sequence identity to SEQ ID NO: 1, SEQ ID NO: 3, SEQ ID NO: 5 or SEQ ID NO: 7.

[38]. A process for treating a cellulose-containing textile, comprising
(a) desizing;
(b) color modification;
wherein a first polypeptide having GH45 cellulase activity and biofinishing activity and a second polypeptide having GH45 cellulase activity and biofinishing activity are added before, during or after step (a) and step (b).

[39]. The process of paragraph 38, wherein the cellulose-containing textile is denim.

[40]. A process for treating a cellulose-containing textile, comprising
(a) desizing;
(b) scouring;
(c) bleaching;
(d) dyeing;
wherein a first polypeptide having GH45 cellulase activity and biofinishing activity and a second polypeptide having GH45 cellulase activity and biofinishing activity are added before, during or after step (a), (b), (c) or (d).

[41] The process of any paragraphs 20-34, wherein the biofinishing is biopolishing or biostoning.

[42]. Use of a first polypeptide having GH45 cellulase activity and biofinishing activity and a second polypeptide having GH45 cellulase activity and biofinishing activity for biofinishing a cellulose-containing textile.

[43]. A fermentation broth formulation or a cell composition comprising a first polypeptide having GH45 cellulase and biofinishing activity, and a second polypeptide having GH45 cellulase and biofinishing activity.

The present invention is further described by the following examples that should not be construed as limiting the scope of the invention.

EXAMPLES

Materials

Chemicals used as buffers and substrates were commercial products of at least reagent grade.

Media 1) pH 5.0 buffer with 50 mM acetate: 2.873 g sodium acetate and 0.901 g acetic acid dissolved in 1 L de-ionized water;

2) pH 6.5 buffer with 50 mM phosphate: 5.642 g disodium hydrogen phosphate dodecahydrate ($Na_2HPO_4 \cdot 12H_2O$) and 5.344 g sodium dihydrogen phosphate dehydrate (NaH$_2$PO$_4$.2H$_2$O) dissolved in 1 L de-ionized water;

3) pH 7.5 buffer with 50 mM phosphate:15.045 g disodium hydrogen phosphate dodecahydrate (Na$_2$HPO$_4$.12H$_2$O) and 1.248 g sodium dihydrogen phosphate dehydrate (NaH$_2$PO$_4$.2H$_2$O) dissolved in 1 L de-ionized water;

4) pH 8.5 buffer with 50 mM phosphate: 17.607 g disodium hydrogen phosphate dodecahydrate (Na$_2$HPO$_4$.12H$_2$O) and 0.116 g potassium dihydrogen phosphate (KH$_2$PO$_4$) dissolved in 1 L de-ionized water.

Enzymes

GH45-1: a *Staphylotrichum coccosporum* GH45 cellulase disclosed as mature polypeptide of SEQ ID NO: 3 in WO2005/054475, and as SEQ ID NO: 2 herein.

GH45-2: a *Thielavia terrestris* GH45 cellulase disclosed as the mature polypeptide of SEQ ID NO: 4 in WO 2012/089024 and as the mature polypeptide of SEQ ID NO: 4 herein.

GH45-3: a *Sordaria fimicola* GH45 cellulase disclosed as the mature polypeptide of SEQ ID NO: 2 in WO 2014/026630 and as the mature polypeptide of SEQ ID NO: 6 herein.

GH45-4: *Neurospora tetrasperma* GH45 cellulase disclosed in the mature polypeptide of SEQ ID NO: 2 in WO 2015/058700 and as the mature polypeptide of SEQ ID NO: 8 herein.

Fabrics

Cotton interlock: 40S, bleached, HM-A0008, available from HM Cotton, Guangzhou, China.

Method

Weight Loss Determination

The swatches were placed in a conditioned room (65%+/-5% humidity, 20+/-1° C.) for 24 hours before they were numbered, weighed by an analytical balance (for samples below 100 g) or a precision balance (for samples over 100 g) and recorded. After treatment, all samples were tumbled dried for 1 hour and conditioned for 24 hours in the conditioned room mentioned as above. For each sample, the weight loss was defined as below:

$$\text{Weight loss \%} = \frac{(\text{weight before treatment} - \text{weight after treatment}) * 100}{\text{weight before treatment}}$$

Pilling Notes Test

Fabrics including treated and untreated were pre-conditioned in norm climate (65% humidity, 21° C.) for at least 24 hours and then tested for the pilling notes with Nu-Martindale Tester (James H. Heal Co. Ltd, England), with untreated fabrics of the same type as the abraded fabrics on the bottom. A standard pilling test (Swiss Norm (SN) 198525) was carried out after 2000 Revolutions by marking from 1-5, with the meaning defined as below, where 1 shows poor anti-pilling and 5 shows excellent anti-pilling property. Thus the higher the Martindale pilling notes score the more effective the cellulose biopolishing treatment.

Note 5: No pilling
Note 4: Slight Pilling
Note 3: Moderate Pilling
Note 2: Distinct Pilling
Note 1: Heavy Pilling
½, ¼ notes are allowed To make the test result more reliable, 3 separate readings were carried out by different persons for each sample, and the average of the 3 readings was adopted as the final result of pilling notes.

Protein Content

The enzyme protein in an enzyme product can be measured with BCA™ Protein Assay Kit (product number 23225, commercial available from Thermo Fisher Scientific Inc.) according to the product manual.

Example 1: Biopolishing with GH45-1 and GH45-2 in Launder-O-Meter

Cellulases GH45-1 and GH45-2 were tested on their own and in blending for biopolishing performance in Launder-O-meter (LOM).

Cotton fabric swatches were cut into about 16 cm*16 cm (about 5 grams each). The swatches were placed in a conditioned room (65% humidity, 21° C.) for 24 hours before they were numbered, weighed by an analytical balance and recorded. The biopolishing was conducted with a LOM. Two conditioned swatches were put into each beaker. 20 big steel balls (total eight of 220 grams) or 4 rubber balls (total weight of 5 grams) were placed in each beaker to supply high and low level of mechanical actions, respectively. The beaker was filled with enzymes according to Table 1 and buffers prepared as described in media part to a total volume of around 100 ml, which could get a liquid to fabric ratio of about 10:1 (v/w).

The LOM machine was started after the required program was chosen, and it would hold when the temperature reached the pre-set temperature, e.g. 55° C. Each beaker was fitted with a lid lined with 2 neoprin gaskets and closed tightly with a metal clamping device. The beakers were loaded into the preheated LOM. Metal racks were used to accommodate and secure 5 beakers, in the vertical position, in each of the 4 drum positions. The LOM lid was closed and the washing program was continued and the timing was initiated. 1 hour later, all beakers were removed from LOM and the denim samples were transferred to an inactivation solution (2 g/L sodium carbonate) at 80° C. for 10 minutes. Then the swatches were rinsed in hot water for 2 times and in cold water for 2 times and they were tumble-dried (AEG, LAVA-THERM 37700, Germany) for 1 hour, conditioned for 24 hours at 65% relative humidity, 21° C. prior to evaluation in weight loss and pilling notes.

As summarized in Table 1, it is evident that the blendings of GH45-1 and GH45-2 can deliver stronger biopolishing performance than any one of these two on their own, i.e. the two GH45 can work in a synergetic way: at high mechanical aids with 20 steel balls, when applied alone, 0.049 mg/g GH45-1 and 0.038 mg/g GH45-2 as 100% on their own delivered 3.8 and 3.6 in pilling notes, respectively; while when these two products were applied together at the ratio 50:50 or 25:75, the blendings can delivered pilling notes 4.5, which was 0.7-0.9 higher than they were applied on their own; at low mechanical aids with 4 rubber balls, when applied alone, 0.049 mg/g GH45-1 and 0.076 mg/g GH45-2 as 100% on their own delivered 1.5 and 3.5 in pilling notes, respectively, while when these two products were applied together at the ratio 95:5, 86:14, 67:33 and 40:60, the blendings can delivered pilling notes 3.3, 3.6, 3.5, 3.9, which were much higher than GH45-1 alone and similar or stronger than GH45-2 alone. To obtain a same benefits in pilling notes, the risk in weight loss was also obviously reduced with the blendings with different ratios.

TABLE 1

Biopolishing in LOM at pH 6.5, 55° C., 1 h

| Enzyme dosage (mg protein/g fabric) | | | | Weight | Pilling |
|---|---|---|---|---|---|
| GH45-2 | GH45-1 | Ratio | Mechanical aids | loss(%) | notes |
| 0.038 | | 100% GH45-2 | 20 steel balls in each beaker | 2.9 | 3.6 |
| | 0.049 | 100% GH45-1 | | 1.7 | 3.8 |
| 0.019 | 0.025 | 50% GH45-1 50% GH45-2 | | 2.8 | 4.5 |
| 0.029 | 0.012 | 25% GH45-1 75% GH45-2 | | 2.9 | 4.5 |
| 0.076 | | 100% GH45-2 | 4 rubber balls in each beaker | 2.5 | 3.5 |
| | 0.049 | 100% GH45-1 | | 1.3 | 1.5 |
| 0.004 | 0.047 | 95% GH45-1 5% GH45-2 | | 1.4 | 3.3 |
| 0.011 | 0.042 | 86% GH45-1 14% GH45-2 | | 1.7 | 3.6 |
| 0.025 | 0.033 | 67% GH45-1 33% GH45-2 | | 2.0 | 3.5 |
| 0.046 | 0.020 | 40% GH45-1 60% GH45-2 | | 2.3 | 3.9 |

Example 2: Biopolishing with GH45-2 and GH45-3 in Launder-O-Meter

Cellulases GH45-2 and GH45-3 were tested on their own and in blending for biopolishing performance in LOM with the same protocol and procedure as in Example 1 except that the biopolishing trials were conducted at 45° C. and 55° C., respectively.

From the results as summarized in Table 2, it can be seen that GH45-2 and GH45-3 also had synergetic effects when they were applied together. For example, at 45° C., when applied alone, 0.146 mg/g GH45-2 and 0.115 mg/g GH45-3 as 100% on their own delivered 4.0 in pilling notes, respectively; while when these two products were applied together at the ratio 80:20 or 60:40, the blendings can delivered pilling notes 4.4, which was 0.4 higher than they were applied on their own. At 55° C. similar synergetic effects between these two GH45s were observed. Meanwhile the blendings of GH45-2 and GH45-3 delivered more consistent performance when temperature changed from 45° C. to 55° C.

TABLE 2

LOM biopolishing at pH 6.5, 45/55° C., 1 h, 20 steel balls in each beaker

| Enzyme dosage (mg protein/ g fabric) | | | 45° C. | | 55° C. | |
|---|---|---|---|---|---|---|
| GH45-2 | GH45-3 | Ratio | Weight loss (%) | Pilling notes | Weight loss (%) | Pilling notes |
| | 0.115 | 100% GH45-3 | 2.3 | 4.0 | 1.2 | 3.5 |
| 0.0432 | 0.023 | 80% GH45-2 20% GH45-3 | 2.3 | 4.4 | 2.2 | 4.5 |
| 0.0324 | 0.046 | 60% GH45-2 40% GH45-3 | 2.3 | 4.4 | 2.4 | 4.3 |
| 0.0540 | | 100% GH45-2 | 1.9 | 4.0 | 2.2 | 4.3 |

Example 3: Biopolishing with GH45-1 and GH45-3 in Launder-O-Meter

Cellulase GH45-1 and GH45-3 were tested on their own and in blending for biopolishing performance in LOM with the same protocol and procedure as in Example 1 except that the biopolishing trials were conducted at 35° C.

As summarized in Table 3, at 35° C., 0.114 mg/g GH45-1 and 0.0805 mg/g GH45-3, were set as 100% base for blending, respectively. GH45-1/GH45-3 blending with all the blending ratios (90:10, 75:26, 50:50, 25:76, 10:90 for GH45-1/GH45-3) delivered better anti-pilling performance than GH45-1 alone or GH45-3 alone.

TABLE 3

LOM biopolishing at pH 6.5, 35° C., 1 h

| Enzyme dosage (mg protein/g fabric) | | | Mechanical | Weight | Pilling |
|---|---|---|---|---|---|
| GH45-3 | GH45-1 | Ratio | aids | loss(%) | notes |
| 0.0805 | | 100% GH45-3 | 20 steel balls in each beaker | 1.3 | 3.5 |
| | 0.114 | 100% GH45-1 | | 1.0 | 3.1 |
| 0.00805 | 0.103 | 90% GH45-1 10% GH45-3 | | 1.0 | 3.8 |
| 0.0207 | 0.0855 | 75% GH45-1 26% GH45-3 | | 1.3 | 3.7 |
| 0.0403 | 0.0570 | 50% GH45-1 50% GH45-3 | | 1.3 | 3.9 |
| 0.0610 | 0.0285 | 25% GH45-1 76% GH45-3 | | 1.5 | 3.7 |
| 0.0725 | 0.0114 | 10% GH45-1 90% GH45-3 | | 1.4 | 4.2 |

Example 4: Biopolishing with GH45-2 and GH45-4 in Launder-O-Meter

Similar to Example 3, biopolishing trials were conducted to compare cellulases GH45-2 and GH45-4 on their own and in blending.

As summarized in Table 4, at 55° C., 0.0394 mg/g GH45-2 and 0.0378 mg/g GH45-4 as 100% on their own delivered pilling notes at 3.8 and 2.9, respectively, while the blendings of GH45-2 and GH45-4 at different ratios (30:70, 52:50, 70:30 for GH45-2/GH45-4) can deliver similar performance to GH45-2 and much better performance than GH45-4 alone, which also suggested that these two GH45s can work in a synergetic way.

TABLE 4

LOM biopolishing at pH 6.5, 55° C., 1 h, 20 steel balls in each beaker

| Enzyme dosage (mg protein/g fabric) | | | Weight | Pilling |
|---|---|---|---|---|
| GH45-2 | GH45-4 | Ratio | loss(%) | notes |
| 0.0394 | | 100% GH45-2 | 2.3 | 3.8 |
| | 0.0378 | 100% GH45-4 | 1.7 | 2.9 |
| 0.0117 | 0.0268 | 30% GH45-2 70% GH45-2 | 2.2 | 3.6 |
| 0.0204 | 0.0189 | 52% GH45-2 50% GH45-4 | 2.5 | 3.9 |
| 0.0277 | 0.0113 | 70% GH45-2 30% GH45-4 | 2.0 | 3.5 |

Example 5: Biopolishing with GH45-1 and GH45-4 in Launder-O-Meter

Similar to Example 4, biopolishing trials were conducted to compare cellulases GH45-1 and GH45-4 on their own and in blending.

As summarized in Table 5, at 35° C., 0.114 mg/g GH45-1 and 0.0945 mg/g GH45-4 as 100% on their own delivered pilling notes at 3.1 and 4.3, respectively. When 25%, 50%, 75% and 90% GH45-1 was replaced with the corresponding percentages of GH45-4, the resulting blendings delivered pilling notes in the range of 4.1 to 4.3, which indicated the synergetic effects between these two cellulases.

TABLE 5

LOM biopolishing at pH 6.5, 35° C., 1 h, 20 steel balls in each beaker

| Enzyme dosage (mg protein/g fabric) | | | Weight | Pilling |
|---|---|---|---|---|
| GH45-2 | GH45-4 | Ratio | loss(%) | notes |
| 0.0114 | | 100% GH45-1 | 1.0 | 3.1 |
| | 0.0945 | 100% GH45-4 | 2.2 | 4.3 |
| 0.0855 | 0.0236 | 75% GH45-1 25% GH45-4 | 2.0 | 4.2 |
| 0.0570 | 0.0473 | 50% GH45-1 50% GH45-4 | 1.9 | 4.3 |
| 0.0285 | 0.0709 | 25% GH45-1 75% GH45-4 | 2.4 | 4.3 |
| 0.0114 | 0.0851 | 10% GH45-1 90% GH45-4 | 2.3 | 4.1 |

Example 6: Biopolishing with GH45-2 and GH45-3 in a Jet Dyer

Celluases GH45-2 and GH45-3 which had been tested in Example 2, were also tested in a production machine in a textile mill.

In each trial, about 20 kg 100% cotton fabrics which had been scoured and bleached by the mill were loaded into a dyeing machine (Shuangxi ECO Jet). The winch speed and pump pressure were adjusted to make sure the fabric circulate once every 55 seconds and ran smoothly in the machine; 200 L water was loaded in each step to keep the liquor ratio of about 10:1 (water volume/fabric weight). In each trial, the fabric was treated as followed:
1) Pre-washed with water at room temperature for 10 min;
2) Drained;
3) Main-washed with a cellulase bath at 35° C. or 55° C. pH 6-6.5 adjusted with acetic acid, initiated timing when cellulase was loaded into the bath and collected the fabrics after 45, 60, 75, 90 and 105 min;
4) Drained;
5) Rinsed with water twice;
6) Centrifuged and dried.

The fabrics collected in the process were sent for further evaluation for fuzz level and pilling notes (after Nu-Martindale treatment).

From Table 6 it can be seen that the two cellulases works in a synergetic way: 0.244 mg/g GH45-2 at 55° C. delivered similar biopolishing performance as 0.380 mg/g GH45-3 at 35° C., while the blending of these two cellulases at 50:50 or 70:30 for GH45-2/GH45-3 at 55° C. delivered a stronger and faster biopolishing than both on their own. In 60 min treatment, GH45-2 and GH45-3 delivered pilling notes 2.0 and 2.5, respectively; while the blendings at two ratios delivered 3.5 and 2.8, respectively. It can also been seen that a similar trend in fuzz level: the blendings delivered an equivalent fuzz level with 15-30 min shorter time than GH45-2 or GH45-3 on their own. It can further been seen that the blending with 50% GH45-2 and 50% GH45-3 delivered a stable biopolishing performance when the main washes were conducted at 35° C. or 55° C.

TABLE 6

Biopolishing at pH 6-6.5, 35° C. or 55° C. in a jet dyer

| Enzyme dosage (mg protein/g fabric) | | | Temp- erature | Pilling notes | | | | |
|---|---|---|---|---|---|---|---|---|
| GH45-2 | GH45-3 | Ratio | (° C.) | 45' | 60' | 75' | 90' | 105' |
| 0.244 | | 100% GH45-2 | 55 | 1.9 | 2.0 | 3.3 | 3.5 | 4.0 |
| | 0.380 | 100% GH45-3 | 35 | 2.0 | 2.5 | 2.8 | 3.4 | 3.9 |
| 0.121 | 0.192 | 50% GH45-2 50% GH45-3 | 55 | 2.3 | 3.5 | 3.4 | 3.6 | 3.9 |
| 0.121 | 0.192 | 50% GH45-2 50% GH45-3 | 35 | 2.1 | 3.5 | 3.3 | 3.4 | 3.9 |
| 0.171 | 0.115 | 70% GH45-2 30% GH45-3 | 55 | 2.1 | 2.8 | 3.0 | 3.9 | 4.1 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for biofinishing a cellulose-containing textile, comprising:
    (a) treating the cellulose-containing textile with a first GH45 cellulase having biofinishing activity; and
    (b) treating the cellulose-containing textile with a second GH45 cellulase having biofinishing activity,
    wherein the first GH45 cellulase or the second GH45 cellulase has at least 90% sequence identity to SEQ ID NO: 2, at least 90% sequence identity to amino acids 22-299 of SEQ ID NO: 4, at least 90% sequence identity to amino acids 22 to 294 of SEQ ID NO: 6 or at least 90% sequence identity to amino acids 22-293 of SEQ ID NO: 8.

2. A process for treating a cellulose-containing textile, comprising
    (a) desizing;
    (b) color modification;
    wherein a first GH45 cellulase having biofinishing activity and a second GH45 cellulase having biofinishing activity are added before, during or after step (a) and step (b),
    wherein the first GH45 cellulase or the second GH45 cellulase has at least 90% sequence identity to SEQ ID NO: 2, at least 90% sequence identity to amino acids 22-299 of SEQ ID NO: 4, at least 90% sequence identity to amino acids 22 to 294 of SEQ ID NO: 6 or at least 90% sequence identity to amino acids 22-293 of SEQ ID NO: 8.

3. A process for treating a cellulose-containing textile, comprising
    (a) desizing;
    (b) scouring;
    (c) bleaching;
    (d) dyeing;
    wherein a first GH45 cellulase having biofinishing activity and a second GH45 cellulase having biofinishing activity are added before, during or after step (a), (b), (c) or (d),
    wherein the first GH45 cellulase or the second GH45 cellulase has at least 90% sequence identity to SEQ ID NO: 2, at least 90% sequence identity to amino acids 22-299 of SEQ ID NO: 4, at least 90% sequence identity to amino acids 22 to 294 of SEQ ID NO: 6 or at least 90% sequence identity to amino acids 22-293 of SEQ ID NO: 8.

4. The process of claim 1, wherein the first GH45 cellulase or the second GH45 cellulase has at least 95% sequence identity to SEQ ID NO: 2, at least 95% sequence identity to amino acids 22-299 of SEQ ID NO: 4, at least 95% sequence identity to amino acids 22 to 294 of SEQ ID NO: 6 or at least 95% sequence identity to amino acids 22-293 of SEQ ID NO: 8.

5. The process of claim 1, wherein the first GH45 cellulase or the second GH45 cellulase has at least 97% sequence identity to SEQ ID NO: 2, at least 97% sequence identity to amino acids 22-299 of SEQ ID NO: 4, at least 97% sequence identity to amino acids 22 to 294 of SEQ ID NO: 6 or at least 97% sequence identity to amino acids 22-293 of SEQ ID NO: 8.

6. The process of claim 1, wherein the first GH45 cellulase or the second GH45 cellulase comprises or consists of SEQ ID NO: 2, amino acids 22-299 of SEQ ID NO: 4, amino acids 22 to 294 of SEQ ID NO: 6 or amino acids 22-293 of SEQ ID NO: 8.

7. The process of claim 1, wherein the first GH45 cellulase or the second GH45 cellulase has at least 95% sequence identity to amino acids 22-299 of SEQ ID NO: 4.

8. The process of claim 1, wherein the first GH45 cellulase or the second GH45 cellulase has at least 97% sequence identity to amino acids 22-299 of SEQ ID NO: 4.

9. The process of claim 1, wherein the first GH45 cellulase or the second GH45 cellulase comprises or consists of amino acids 22-299 of SEQ ID NO: 4.

10. The process of claim 2, wherein the first GH45 cellulase or the second GH45 cellulase has at least 95% sequence identity to SEQ ID NO: 2, at least 95% sequence identity to amino acids 22-299 of SEQ ID NO: 4, at least 95% sequence identity to amino acids 22 to 294 of SEQ ID NO: 6 or at least 95% sequence identity to amino acids 22-293 of SEQ ID NO: 8.

11. The process of claim 2, wherein the first GH45 cellulase or the second GH45 cellulase has at least 97% sequence identity to SEQ ID NO: 2, at least 97% sequence identity to amino acids 22-299 of SEQ ID NO: 4, at least 97% sequence identity to amino acids 22 to 294 of SEQ ID NO: 6 or at least 97% sequence identity to amino acids 22-293 of SEQ ID NO: 8.

12. The process of claim 2, wherein the first GH45 cellulase or the second GH45 cellulase comprises or consists of SEQ ID NO: 2, amino acids 22-299 of SEQ ID NO: 4, amino acids 22 to 294 of SEQ ID NO: 6 or amino acids 22-293 of SEQ ID NO: 8.

13. The process of claim 2, wherein the first GH45 cellulase or the second GH45 cellulase has at least 95% sequence identity to amino acids 22-299 of SEQ ID NO: 4.

14. The process of claim 2, wherein the first GH45 cellulase or the second GH45 cellulase has at least 97% sequence identity to amino acids 22-299 of SEQ ID NO: 4.

15. The process of claim 2, wherein the first GH45 cellulase or the second GH45 cellulase comprises or consists of amino acids 22-299 of SEQ ID NO: 4.

16. The process of claim 3, wherein the first GH45 cellulase or the second GH45 cellulase has at least 95% sequence identity to SEQ ID NO: 2, at least 95% sequence identity to amino acids 22-299 of SEQ ID NO: 4, at least 95% sequence identity to amino acids 22 to 294 of SEQ ID NO: 6 or at least 95% sequence identity to amino acids 22-293 of SEQ ID NO: 8.

17. The process of claim 3, wherein the first GH45 cellulase or the second GH45 cellulase has at least 97% sequence identity to SEQ ID NO: 2, at least 97% sequence identity to amino acids 22-299 of SEQ ID NO: 4, at least 97% sequence identity to amino acids 22 to 294 of SEQ ID NO: 6 or at least 97% sequence identity to amino acids 22-293 of SEQ ID NO: 8.

18. The process of claim 3, wherein the first GH45 cellulase or the second GH45 cellulase comprises or consists of SEQ ID NO: 2, amino acids 22-299 of SEQ ID NO: 4, amino acids 22 to 294 of SEQ ID NO: 6 or amino acids 22-293 of SEQ ID NO: 8.

19. The process of claim 3, wherein the first GH45 cellulase or the second GH45 cellulase has at least 95% sequence identity to amino acids 22-299 of SEQ ID NO: 4.

20. The process of claim 3, wherein the first GH45 cellulase or the second GH45 cellulase has at least 97% sequence identity to amino acids 22-299 of SEQ ID NO: 4.

21. The process of claim 3, wherein the first GH45 cellulase or the second GH45 cellulase comprises or consists of amino acids 22-299 of SEQ ID NO: 4.

* * * * *

SEQUENCE LISTING

<160> NUMBER OF SEQ ID NOS: 72

<210> SEQ ID NO 1
<211> LENGTH: 951
<212> TYPE: DNA
<213> ORGANISM: Staphylotrichum coccosporum

<400> SEQUENCE: 1

```
atgcgttcct cccccgtcct ccgcacggcc ctggccgctg ccctcccct  ggccgccctc      60 gctgccgatg gcaagtcgac ccgctactgg gactgttgca agccgtcgtg ctcgtggccc     120
ggcaaggcct cggtgaacca gcccgtcttc gcctgcagcg ccaacttcca gcgcatcagc     180
gaccccaacg tcaagtcggg ctgcgacggc ggctccgcct acgcctgcgc cgaccagacc     240
ccgtgggccg tcaacgacaa cttctcgtac ggcttcgccg ccacgtccat ctcgggcggc     300
aacgaggcct cgtggtgctg tggctgctac gagctgacct tcacctcggg ccccgtcgct     360
ggcaagacca tggttgtcca gtccacctcg accggcggcg acctcggcac caaccacttc     420
```

```
gacctggcca tgcccggtgg tggtgtcggc atcttcgacg gctgctcgcc ccagttcggc    480
ggcctcgccg cgaccgcta cggcggcgtc tcgtcgcgca gccagtgcga ctcgttcccc    540
gccgccctca agcccggctg ctactggcgc ttcgactggt tcaagaacgc cgacaacccg    600
accttcacct tccgccaggt ccagtgcccg tcggagctcg tcgcccgcac cggctgccgc    660
cgcaacgacg acggcaactt ccccgtcttc acccctccct cgggcggtca gtcctcctcg    720
tcttcctcct ccagcagcgc caagcccacc tccacctcca cctcgaccac ctccaccaag    780
gctacctcca ccacctcgac cgcctccagc cagacctcgt cgtccaccgg cggcggctgc    840
gccgcccagc gctgggcgca gtgcggcggc atcgggttct cgggctgcac cacgtgcgtc    900
agcggcacca cctgcaacaa gcagaacgac tggtactcgc agtgccttta a              951
```

<210> SEQ ID NO 2
<211> LENGTH: 295
<212> TYPE: PRT
<213> ORGANISM: Staphylotrichum coccosporum

<400> SEQUENCE: 2

```
Ala Asp Gly Lys Ser Thr Arg Tyr Trp Asp Cys Cys Lys Pro Ser Cys
 1               5                  10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270
```

Ser Gly Cys Thr Thr Cys Val Ser Gly Thr Thr Cys Asn Lys Gln Asn
          275                 280                 285

Asp Trp Tyr Ser Gln Cys Leu
    290             295

<210> SEQ ID NO 3
<211> LENGTH: 1044
<212> TYPE: DNA
<213> ORGANISM: Thielavia terrestris
<220> FEATURE:
<221> NAME/KEY: Intron
<222> LOCATION: (90)..(167)
<220> FEATURE:
<221> NAME/KEY: Intron
<222> LOCATION: (417)..(485)

<400> SEQUENCE: 3
atgcgctcta ctcccgttct tcgcacaacc ctggccgctg cacttcctct ggtcgcctcc      60
gcggccagtg gcagtggcca gtccacgagg tatgcgtccc tcaatgcgaa tgcctcacca     120
aacgagctag gtgtccagga cgccgcccat gctgactcgt tcccagata ctgggactgc     180 tgcaagccgt cgtgcgcttg gcccgggaag ccgccgtca gccaaccggt ctacgcgtgc     240
gatgccaact tccagcgcct gtccgacttc aatgtccagt cgggctgcaa cggcggctcg     300
gcctactcct cgccgaccac gactccctgg gcggtgaacg acaatctcgc ctacggcttc     360
gccgcgacga gcatcgccgg cgggtccgaa tcctcgtggt gctgcgcctg ctacgcgtaa     420
gtcctctctg ccagctacca ggaagttgga ttagcgcgag ctaacctcac tccatcacac     480
tccaggctca ccttcacttc cggtcccgtc gccggcaaga caatggtggt gcagtcaacg     540
agcactggcg gcgacctggg aagtaaccat ttcgatatcg ccatgcccgg cggcggcgtg     600
ggcatcttca acggctgcag ctcgcagttc ggcggcctcc ccggcgctca atacggcggc     660
atttcgtcgc gcgaccagtg cgattccttc cccgcgccgc tcaagcccgg ctgccagtgg     720
cggtttgact ggttccagaa cgccgacaac ccgacgttca cgttccagca ggtgcagtgc     780
cccgccgaga tcgttgcccg ctccggctgc aagcgcaacg acgactccag cttccccgtc     840
ttcacccccc caagcggtgg caacggtggc accgggacgc ccacgtcgac tgcgcctggg     900
tcgggccaga cgtctcccgg cggcggcagt ggctgcacgt ctcagaagtg gctcagtgc      960 ggtggcatcg gcttcagcgg atgcaccacc tgtgtctctg caccacctg ccagaagttg     1020 aacgactact actcgcagtg cctc                                           1044

<210> SEQ ID NO 4
<211> LENGTH: 299
<212> TYPE: PRT
<213> ORGANISM: Thielavia terrestris
<220> FEATURE:
<221> NAME/KEY: SIGNAL
<222> LOCATION: (1)..(21)

<400> SEQUENCE: 4

Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
            20                  25                  30

Asp Cys Cys Lys Pro Ser Cys Ala Trp Pro Gly Lys Ala Ala Val Ser
        35                  40                  45

Gln Pro Val Tyr Ala Cys Asp Ala Asn Phe Gln Arg Leu Ser Asp Phe
    50                  55                  60

Asn Val Gln Ser Gly Cys Asn Gly Gly Ser Ala Tyr Ser Cys Ala Asp
 65                  70                  75                  80

Gln Thr Pro Trp Ala Val Asn Asp Asn Leu Ala Tyr Gly Phe Ala Ala
                 85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
    130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
    210                 215                 220

Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
        275                 280                 285

Gln Lys Leu Asn Asp Tyr Tyr Ser Gln Cys Leu
    290                 295

<210> SEQ ID NO 5
<211> LENGTH: 1048
<212> TYPE: DNA
<213> ORGANISM: Sordaria fimicola

<400> SEQUENCE: 5
caagatacaa tatgcgttcc tccactattt tgcaaaccgg cctggtggcc gttctcccct    60
tcgccgtcca ggccgcctca ggatccggca agtccaccag atattgggac tgctgcaaac   120
catcttgtgc ctggtccggc aaggcttctg tcaaccgccc tgttctcgcc tgcgacgcaa   180
acaacaaccc gctgaacgac gccaacgtca agtcaggatg tgatggcggt tctgcataca   240
cctgtgccaa caactctccc tgggcagtga atgacaatct ggcctacggc ttcgcggcca   300
cgaaactcag cggggggacc gagtcatctt ggtgctgcgc ctgttatgcc ctcacattca   360
catcgggtcc tgtttctggc aagaccttgg ttgtccagtc taccagtacc ggtggtgatc   420
ttggctctaa tcatttcgat ctcaacatgc ccggcggagg cgttggccta tttgacggtt   480
gtaaacggga gtttggcggt ctccccggcg cccaatacgg cggcatcagc tctcgcagcg   540
agtgcgactc cttcccggcc gctcttaagc ccggctgcca gtggcgcttc gactggttca   600
agaacgccga caacccggag ttcacctca gcaggtcca atgcccgtcc gagcttacct   660
cccgcaccgg ctgcaagcga acgacgact cccagttccc ggcttttact cctccttctg   720
gtggaggcag caaccctct actccgacaa ctcctccct ttctggcggc ggcggctccg   780

```
gatgtgctgc ggctatgtac gctcagtgtg gcggctcagg attttctggt tgcaccaatt    840
gcccatctgg atcgacctgc aaggccatca atgattacta tcaccagtgt gcctaagtag    900
tgccaagtgg tatgcggggt tgtggtgtct cgaattgaga gtagggaccg gctaaaaggg    960
atcggtagag agcacatcct tcaagtacaa tctcatactg ctgtgggcat tttgtttatc   1020
caaaaaaaaa aaaaaaaaaa aaaaaaa                                       1048
```

<210> SEQ ID NO 6
<211> LENGTH: 294
<212> TYPE: PRT
<213> ORGANISM: Sordaria fimicola

<400> SEQUENCE: 6

```
Met Arg Ser Ser Thr Ile Leu Gln Thr Gly Leu Val Ala Val Leu Pro
1               5                   10                  15

Phe Ala Val Gln Ala Ala Ser Gly Ser Gly Lys Ser Thr Arg Tyr Trp
                20                  25                  30

Asp Cys Cys Lys Pro Ser Cys Ala Trp Ser Gly Lys Ala Ser Val Asn
            35                  40                  45

Arg Pro Val Leu Ala Cys Asp Ala Asn Asn Asn Pro Leu Asn Asp Ala
        50                  55                  60

Asn Val Lys Ser Gly Cys Asp Gly Gly Ser Ala Tyr Thr Cys Ala Asn
65                  70                  75                  80

Asn Ser Pro Trp Ala Val Asn Asp Asn Leu Ala Tyr Gly Phe Ala Ala
                85                  90                  95

Thr Lys Leu Ser Gly Gly Thr Glu Ser Ser Trp Cys Cys Ala Cys Tyr
                100                 105                 110

Ala Leu Thr Phe Thr Ser Gly Pro Val Ser Gly Lys Thr Leu Val Val
            115                 120                 125

Gln Ser Thr Ser Thr Gly Gly Asp Leu Gly Ser Asn His Phe Asp Leu
        130                 135                 140

Asn Met Pro Gly Gly Gly Val Gly Leu Phe Asp Gly Cys Lys Arg Glu
145                 150                 155                 160

Phe Gly Gly Leu Pro Gly Ala Gln Tyr Gly Gly Ile Ser Ser Arg Ser
                165                 170                 175

Glu Cys Asp Ser Phe Pro Ala Ala Leu Lys Pro Gly Cys Gln Trp Arg
            180                 185                 190

Phe Asp Trp Phe Lys Asn Ala Asp Asn Pro Glu Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Ala Phe Thr Pro Pro Ser Gly Gly Gly Ser
225                 230                 235                 240

Asn Pro Ser Thr Pro Thr Thr Pro Pro Ser Gly Gly Gly Ser
                245                 250                 255

Gly Cys Ala Ala Ala Met Tyr Ala Gln Cys Gly Gly Ser Gly Phe Ser
            260                 265                 270

Gly Cys Thr Asn Cys Pro Ser Gly Ser Thr Cys Lys Ala Ile Asn Asp
        275                 280                 285

Tyr Tyr His Gln Cys Ala
    290
```

<210> SEQ ID NO 7
<211> LENGTH: 935
<212> TYPE: DNA
<213> ORGANISM: Neurospora tetrasperma

<400> SEQUENCE: 7

```
atgcgctcct ccactgttct gcaaaccggg ctagtggccg ctcttccctt cgccgttcag     60
gccgcgtccg gatccggcca gtccaccaga tattgggact gctgcaaacc atcttgctcc    120
tggtccggca aggcttctgt caaccgaccc gtcctcgctt gcgatgcaaa caacaacccc    180
ctgagcgacg ccagtgtcaa gtctggatgt gacggcggtt ctgcatacac ctgtgccaac    240
aactcaccat gggcggtgaa cgaccagctc tcctacggct tgctgccac gaaactcagt     300
ggtggaaccg agtcgtcttg gtgctgtgcc tgttatgcgt gagtttcgcg tcaacagctg    360
ggtatcactt gatggctaat ttatactgca gccttacctt cacttcgggt cctgttgctg    420
gcaagaccat ggtcgttcag tctaccagta ccggcggtga tctcggctcc aaccacttcg    480
atatcaacat gccggcggc ggcgtcggcc tgtttgatgg ctgtacacga cagtttggcg     540
gtctccccgg cgctcaatat ggcggcatca gctcccgcag ccagtgcgat tcattccctg    600
ccgcgctcaa gccggttgc cagtggcgct tcgactggtt ccagaacgcc gacaacccca     660
acttcacctt caagcaggtc caatgcccat ccgagctcac ctcccgcacc ggctgcaagc    720
gaaacgacga ctctcaattc cctgtcttca ctccgccctc tggtggaggc accaacccct    780
ctactccgac aaccctcccc tcttcaggcg gcggttccgg atgtacggcg ataaatacg     840
ctcagtgtgg cggctcgggg tggtctggct gcaccaactg cccgtctgga tcgacctgca    900
agactatcaa cgattattac caccagtgtg cctaa                               935
```

<210> SEQ ID NO 8
<211> LENGTH: 293
<212> TYPE: PRT
<213> ORGANISM: Neurospora tetrasperma

<400> SEQUENCE: 8

```
Met Arg Ser Ser Thr Val Leu Gln Thr Gly Leu Val Ala Ala Leu Pro
1               5                   10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Ser Val Asn
        35                  40                  45

Arg Pro Val Leu Ala Cys Asp Ala Asn Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
    130                 135                 140

Asn Met Pro Gly Gly Gly Val Gly Leu Phe Asp Gly Cys Thr Arg Gln
145                 150                 155                 160

Phe Gly Gly Leu Pro Gly Ala Gln Tyr Gly Gly Ile Ser Ser Arg Ser
                165                 170                 175
```

```
Gln Cys Asp Ser Phe Pro Ala Ala Leu Lys Pro Gly Cys Gln Trp Arg
                180                 185                 190

Phe Asp Trp Phe Gln Asn Ala Asp Asn Pro Asn Phe Thr Phe Lys Gln
            195                 200                 205

Val Gln Cys Pro Ser Glu Leu Thr Ser Arg Thr Gly Cys Lys Arg Asn
        210                 215                 220

Asp Asp Ser Gln Phe Pro Val Phe Thr Pro Ser Gly Gly Gly Thr
225                 230                 235                 240

Asn Pro Ser Thr Pro Thr Thr Pro Pro Ser Ser Gly Gly Ser Gly
                245                 250                 255

Cys Thr Ala Asp Lys Tyr Ala Gln Cys Gly Gly Ser Gly Trp Ser Gly
                260                 265                 270

Cys Thr Asn Cys Pro Ser Gly Ser Thr Cys Lys Thr Ile Asn Asp Tyr
                275                 280                 285

Tyr His Gln Cys Ala
        290

<210> SEQ ID NO 9
<211> LENGTH: 225
<212> TYPE: PRT
<213> ORGANISM: Trichoderma reesei

<400> SEQUENCE: 9

Tyr Lys Ala Thr Thr Arg Tyr Tyr Asp Gly Gln Glu Gly Ala Cys
1               5                   10                  15

Gly Cys Gly Ser Ser Ser Gly Ala Phe Pro Trp Gln Leu Gly Ile Gly
                20                  25                  30

Asn Gly Val Tyr Thr Ala Ala Gly Ser Gln Ala Leu Phe Asp Thr Ala
            35                  40                  45

Gly Ala Ser Trp Cys Gly Ala Gly Cys Gly Lys Cys Tyr Gln Leu Thr
        50                  55                  60

Ser Thr Gly Gln Ala Pro Cys Ser Ser Cys Gly Thr Gly Gly Ala Ala
65                  70                  75                  80

Gly Gln Ser Ile Ile Val Met Val Thr Asn Leu Cys Pro Asn Asn Gly
                85                  90                  95

Asn Ala Gln Trp Cys Pro Val Val Gly Gly Thr Asn Gln Tyr Gly Tyr
            100                 105                 110

Ser Tyr His Phe Asp Ile Met Ala Gln Asn Glu Ile Phe Gly Asp Asn
        115                 120                 125

Val Val Val Asp Phe Glu Pro Ile Ala Cys Pro Gly Gln Ala Ala Ser
130                 135                 140

Asp Trp Gly Thr Cys Leu Cys Val Gly Gln Gln Glu Thr Asp Pro Thr
145                 150                 155                 160

Pro Val Leu Gly Asn Asp Thr Gly Ser Thr Pro Pro Gly Ser Ser Pro
                165                 170                 175

Pro Ala Thr Ser Ser Ser Pro Pro Ser Gly Gly Gln Gln Thr Leu
            180                 185                 190

Tyr Gly Gln Cys Gly Gly Ala Gly Trp Thr Gly Pro Thr Thr Cys Gln
        195                 200                 205

Ala Pro Gly Thr Cys Lys Val Gln Asn Gln Trp Tyr Ser Gln Cys Leu
210                 215                 220

Pro
225
```

```
<210> SEQ ID NO 10
<211> LENGTH: 247
<212> TYPE: PRT
<213> ORGANISM: Trichoderma viride

<400> SEQUENCE: 10

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro Trp Glu Gly Pro Arg
                245

<210> SEQ ID NO 11
<211> LENGTH: 266
<212> TYPE: PRT
<213> ORGANISM: Penicillium decumbens

<400> SEQUENCE: 11

Met Lys Gly Lys Val Ala Phe Leu Leu Leu Asp Leu Leu Ala Ser Ala
1               5                   10                  15

Ala Ala Tyr Lys Ala Thr Thr Thr Arg Tyr Tyr Asp Gly Gln Glu Gly
            20                  25                  30

Ala Cys Gly Cys Gly Ser Ser Ser Gly Leu Phe Pro Trp Gln Leu Gly
        35                  40                  45

Ile Gly Asn Gly Val Tyr Thr Ala Ala Gly Ser Gln Ala Leu Phe Asp
    50                  55                  60

Thr Ala Gly Ala Asp Trp Cys Gly Ala Gly Cys Gly Lys Cys Tyr Lys
65                  70                  75                  80

Leu Thr Ser Thr Gly Glu Pro Pro Cys Lys Asp Cys Gly Thr Gly Gly
```

```
                85                  90                  95
Val Ala Gly Gln Ser Ile Ile Val Met Val Thr Asn Leu Cys Pro Tyr
            100                 105                 110

Asn Gly Asn Gln Gln Trp Cys Pro Asn Pro Gly Ser Thr Asn Gln Tyr
            115                 120                 125

Gly Tyr Ser Tyr His Phe Asp Ile Met Ala Gln Asn Glu Ile Phe Gly
        130                 135                 140

Asp Asn Val Val Val Asp Phe Glu Pro Ile Ala Cys Pro Gly Gln Ala
145                 150                 155                 160

Asn Ser Asp Trp Gln Ser Cys Val Cys Tyr Gly Lys Thr Glu Thr Asp
                165                 170                 175

Thr Thr Pro Val Gly Leu Thr Ala Gly Gly Gly Gly Gly Gly Ser Ser
            180                 185                 190

Gln Ser Ser Thr Thr Ser Gln Gly Ser Thr Thr Arg Thr Thr Leu
                195                 200                 205

Thr Ala Thr Thr Thr Ala Gly Ser Gly Ser Gly Ser Gly Ser
        210                 215                 220

Gly Ser Ser Gly Thr Gln Ser Val Tyr Gly Gln Cys Gly Gly Ser
225                 230                 235                 240

Gly Trp Thr Gly Pro Thr Asn Cys Ala Ser Gly Ser Lys Cys Thr Ala
                245                 250                 255

Gln Asn Gln Trp Tyr Ser Gln Cys Leu Pro
            260                 265
```

<210> SEQ ID NO 12
<211> LENGTH: 247
<212> TYPE: PRT
<213> ORGANISM: Aspergillus nidulans

<400> SEQUENCE: 12

```
Met Gln Arg Ile Pro Asp Arg Leu Ser Asp Ser Thr Arg Ile Thr Arg
1               5                   10                  15

Pro His Arg Ser Leu Cys Cys Asn Thr Gly Gly Ala Ser Ser Ser Cys
                20                  25                  30

Pro Gly Tyr His Asn Cys Ala Cys Gly Cys Gly Asn Lys Ile Gly Thr
            35                  40                  45

Tyr Asp Trp Ser Tyr Gly Ile Ala Asn Lys Val Tyr Thr Ala Ala Ala
50                  55                  60

Asn Gln Ala Leu Phe Asp Ser Gly Pro Asn Asp Ala Thr His Trp Cys
65                  70                  75                  80

Gly Asn Gly Cys Gly Lys Cys Tyr Arg Leu Thr Ser Thr Gly Val Ser
                85                  90                  95

Thr Cys Glu Thr Cys Gly Ala Gly Gly Glu Gln Gly Lys Ser Ile Val
            100                 105                 110

Val Met Val Thr Asn Leu Cys Pro Phe Lys Gly Asn Glu Arg Trp Cys
        115                 120                 125

Pro Asn Pro Gly Gln Leu Asn Pro His Gly Tyr Ala Tyr His Phe Asp
130                 135                 140

Ile Met Gly Gly Ala Gly Val Phe Gly Asp Asn Val Val Glu Phe
145                 150                 155                 160

Glu Glu Val Pro Cys Pro Gly Asp Ala Ala Phe Lys Trp Ala Ala Cys
                165                 170                 175

Glu Cys His Pro Asn Leu Arg Asn Lys Asp Leu Thr Leu Asn Ala Gly
            180                 185                 190
```

```
Ala His Ala Ala Gly Ser Lys Ile Val Gly Pro Ala Gln Ala Ala Ile
            195                 200                 205

Ile Ser Val Asn Gly Leu Pro Ala Pro Ala Ala Met Ala Val Gln Pro
210                 215                 220

Pro Pro Pro Pro Pro Pro Ala Pro Ala Arg Pro Ala Ile Glu Ile
225                 230                 235                 240

Pro Pro Pro Pro Ala Pro Val
            245
```

<210> SEQ ID NO 13
<211> LENGTH: 194
<212> TYPE: PRT
<213> ORGANISM: Haliotis discus discus

<400> SEQUENCE: 13

```
Met Lys Thr Ala Val Ser Ile Leu Leu Leu Phe Ala Ala Ser Ala Trp
1               5                   10                  15

Ala Asn Gln Lys Cys Gln Met His Asn Gly Ile Arg Met Tyr Asn Gly
            20                  25                  30

Lys His Cys Ala Ser Thr Thr Arg Tyr Asn Asp Gly His Lys Gly Ala
        35                  40                  45

Cys Gly Cys Gly Gln Asn Asp Thr Pro Phe Pro Trp Asn Asn Asn Gln
50                  55                  60

Tyr Val Ala Ala Ala Asn Gln Lys Leu Phe Ser Asn Ser Gly Ser Thr
65                  70                  75                  80

Trp Cys Gly Asp Ser Cys Gly Lys Cys Val Lys Leu Thr Thr Thr Gly
                85                  90                  95

Gly Ser Ile Pro Gly Ala Gly Thr Gly Ala His Ala Gly Gln Ser His
            100                 105                 110

Val Phe Met Ile Thr Asn Asp Cys Pro Asp Val Ala Pro Asn Leu Glu
        115                 120                 125

Trp Cys Ala Gln Lys Gly Ala Pro Gly Ser Gly His Gly Asn Thr His
130                 135                 140

Gly Tyr Glu Val His Phe Asp Leu Glu Asn Asn Gly Asn Gln Ile Ser
145                 150                 155                 160

Lys Leu Gly Trp Asp Asn Pro Glu Val Thr Trp Glu Trp Ser Ser Cys
                165                 170                 175

His Gly Ser Asn Thr Pro Thr Asp Gln Met Trp His Thr Cys Glu Cys
            180                 185                 190

Ser His
```

<210> SEQ ID NO 14
<211> LENGTH: 195
<212> TYPE: PRT
<213> ORGANISM: Ampullaria crossean

<400> SEQUENCE: 14

```
Met Lys Leu Phe Tyr Leu Leu Cys Leu Ala Val Pro Leu Leu Glu Ala
1               5                   10                  15

Ala Gln Leu Cys Gln Pro Asp Ser Arg Gly Val Arg Arg Phe Asn Gly
            20                  25                  30

Lys Pro Cys Ala Ser Thr Thr Arg Tyr Val Asp Gly His Lys Gly Ala
        35                  40                  45

Cys Gly Cys Gly Gln Lys Gly Ser Asp Thr Pro Phe Pro Trp Asn Ile
50                  55                  60

Gln Lys His Val Thr Ala Pro Ser Glu Arg Tyr Phe Asp Gly Gly Gly
```

```
            65                  70                  75                  80
Ser Ser Leu Trp Cys Gly Arg Asn Cys Gly Lys Cys Val Lys Leu Thr
                85                  90                  95

Pro Thr Gly Gly Phe Val Pro Gly Lys Gly Asn Ala Pro Pro Asn His
                100                 105                 110

Asn Pro Val Val Phe Gln Val Thr Asn Ala Cys Pro Ile Asn Gly Asn
                115                 120                 125

Glu Glu Trp Cys Gly Ile Ser Gly Ala Pro Thr Gly His Val Asn
        130                 135                 140

Ser His Gly Tyr Glu Val His Phe Asp Leu Gln Asp Gln Val Gly Gln
145                 150                 155                 160

Val Glu Ala Leu His Trp Asp Asn Pro Glu Val Thr Trp Glu Glu Thr
                165                 170                 175

Ser Cys Pro Gly Asp Leu Gln Ser Asn Tyr Gln Gln Cys Glu Cys His
                180                 185                 190

Asn Ser Gly
        195

<210> SEQ ID NO 15
<211> LENGTH: 195
<212> TYPE: PRT
<213> ORGANISM: Ampullaria crossean

<400> SEQUENCE: 15

Met Lys Leu Phe Tyr Leu Leu Cys Leu Ala Val Pro Val Leu Glu Ala
1               5                   10                  15

Ala Gln Leu Cys Gln Pro Asp Ala His Gly Val Arg Arg Phe Asn Gly
                20                  25                  30

Arg Pro Cys Ala Ser Thr Thr Arg Tyr Val Asp Gly His Lys Gly Ala
                35                  40                  45

Cys Gly Cys Gly Gln Lys Gly Ser Asp Thr Pro Phe Pro Trp Asn Leu
        50                  55                  60

Gln Lys His Val Thr Ala Pro Ser Glu Arg Tyr Phe Asp Asp Gly Gly
65                  70                  75                  80

Ser Asn Leu Trp Cys Gly Lys Asn Cys Gly Lys Cys Val Arg Leu Thr
                85                  90                  95

Pro Thr Gly Gly Phe Val Pro Gly Lys Gly Ala Pro Pro Asn His
                100                 105                 110

Asn Pro Val Val Phe Met Val Thr Asn Ala Cys Pro Ile Asn Gly Asn
                115                 120                 125

Glu Glu Trp Cys Gly Ile Ser Gly Lys Pro Gly Thr Asn His Val Asn
        130                 135                 140

Ser His Gly Tyr Glu Val His Phe Asp Leu Gln Asp Gln Val Gly Gln
145                 150                 155                 160

Val Glu Ala Leu His Trp Asp Asn Pro Glu Val Thr Trp Glu Glu Val
                165                 170                 175

Pro Cys Pro Gly Asp Leu Gln Ala Asn Tyr Gln Gln Cys Glu Cys His
                180                 185                 190

Asn Ser Asp
        195

<210> SEQ ID NO 16
<211> LENGTH: 211
<212> TYPE: PRT
<213> ORGANISM: Mytilus edulis
```

<400> SEQUENCE: 16

```
Met Lys Tyr Leu Val Leu Ser Leu Leu Val Leu Val Tyr Ser Val Ser
1               5                   10                  15

Ala Asn Gln Lys Cys Ser Gly Asn Pro Arg Arg Tyr Asn Gly Lys Ser
                20                  25                  30

Cys Ala Ser Thr Thr Asn Tyr His Asp Ser His Lys Gly Ala Cys Gly
            35                  40                  45

Cys Gly Pro Ala Ser Gly Asp Ala Gln Phe Gly Trp Asn Ala Gly Ser
        50                  55                  60

Phe Val Ala Ala Ala Ser Gln Met Tyr Phe Asp Ser Gly Asn Lys Gly
65                  70                  75                  80

Trp Cys Gly Gln His Cys Gly Gln Cys Ile Lys Leu Thr Thr Thr Gly
                85                  90                  95

Gly Tyr Val Pro Gly Gln Gly Gly Pro Val Arg Glu Gly Leu Ser Lys
            100                 105                 110

Thr Phe Met Ile Thr Asn Leu Cys Pro Asn Ile Tyr Pro Asn Gln Asp
        115                 120                 125

Trp Cys Asn Gln Gly Ser Gln Tyr Gly Gly His Asn Lys Tyr Gly Tyr
    130                 135                 140

Glu Leu His Leu Asp Leu Glu Asn Gly Arg Ser Gln Val Thr Gly Met
145                 150                 155                 160

Gly Trp Asn Asn Pro Glu Thr Thr Trp Glu Val Val Asn Cys Asp Ser
                165                 170                 175

Glu His Asn His Asp His Arg Thr Pro Ser Asn Ser Met Tyr Gly Gln
            180                 185                 190

Cys Gln Cys Ala His Gln Gly Lys Arg Gly Leu Asn Glu Thr Ser Asn
        195                 200                 205

Glu Ser Leu
    210
```

<210> SEQ ID NO 17
<211> LENGTH: 206
<212> TYPE: PRT
<213> ORGANISM: Phanerochaete chrysosporium

<400> SEQUENCE: 17

```
Met Ala Lys Leu Ser Met Phe Leu Gly Phe Val Ala Val Ala Thr Leu
1               5                   10                  15

Ala Ser Ala Leu Thr Val Ser Glu Lys Arg Ala Thr Gly Gly Tyr Val
                20                  25                  30

Gln Gln Ala Thr Gly Gln Ala Ser Phe Thr Met Tyr Ser Gly Cys Gly
            35                  40                  45

Ser Pro Ala Cys Gly Lys Ala Ala Ser Gly Phe Thr Ala Ala Ile Asn
        50                  55                  60

Gln Leu Ala Phe Gly Ser Ala Pro Gly Leu Gly Ala Gly Asp Ala Cys
65                  70                  75                  80

Gly Arg Cys Phe Ala Leu Thr Gly Asn His Asp Pro Tyr Ser Pro Asn
                85                  90                  95

Tyr Thr Gly Pro Phe Gly Gln Thr Ile Val Val Lys Val Thr Asp Leu
            100                 105                 110

Cys Pro Val Gln Gly Asn Gln Glu Phe Cys Gly Gln Thr Thr Ser Asn
        115                 120                 125

Pro Thr Asn Gln His Gly Met Pro Phe His Phe Asp Ile Cys Glu Asp
    130                 135                 140
```

```
Thr Gly Gly Ser Ala Lys Phe Phe Pro Ser Gly His Gly Ala Leu Thr
145                 150                 155                 160

Gly Thr Phe Thr Glu Val Ser Cys Ser Gln Trp Ser Gly Ser Asp Gly
            165                 170                 175

Gly Gln Leu Trp Asn Gly Ala Cys Leu Ser Gly Glu Thr Ala Pro Asn
        180                 185                 190

Trp Pro Ser Thr Ala Cys Gly Asn Lys Gly Thr Ala Pro Ser
        195                 200                 205
```

<210> SEQ ID NO 18
<211> LENGTH: 284
<212> TYPE: PRT
<213> ORGANISM: Humicola insolens

<400> SEQUENCE: 18

```
Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Ile Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Pro Ser Ser Ser Thr Ser Ser Pro Val Asn Gln Pro
    210                 215                 220

Thr Ser Thr Ser Thr Ser Thr Ser Thr Ser Ser Pro Pro Val
225                 230                 235                 240

Gln Pro Thr Thr Pro Ser Gly Cys Thr Ala Glu Arg Trp Ala Gln Cys
                245                 250                 255

Gly Gly Asn Gly Trp Ser Gly Cys Thr Thr Cys Val Ala Gly Ser Thr
            260                 265                 270

Cys Thr Lys Ile Asn Asp Trp Tyr His Gln Cys Leu
        275                 280
```

<210> SEQ ID NO 19
<211> LENGTH: 305
<212> TYPE: PRT
<213> ORGANISM: Humicola grisea var. thermoidea

<400> SEQUENCE: 19

```
Met Arg Ser Ser Pro Leu Leu Pro Ser Asp Val Val Ala Ala Leu Pro
1               5                  10                  15

Val Leu Ala Leu Ala Ala Asp Gly Lys Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Leu Thr Asp Phe Asp Ala
    50                  55                  60

Lys Ser Gly Cys Glu Pro Gly Val Ala Tyr Ser Cys Ala Asp Gln
65                  70                  75                  80

Thr Pro Trp Ala Val Asn Asp Asp Phe Ala Phe Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Gly Gln Pro Thr Ser Thr Ser Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 20
<211> LENGTH: 306
<212> TYPE: PRT
<213> ORGANISM: Humicola nigrescens

<400> SEQUENCE: 20

```
Pro Phe Met Met Val Ala Trp Trp Ser Leu Phe Leu Tyr Gly Leu Gln
1               5                  10                  15

Val Ala Ala Pro Ala Phe Ala Ala Asp Gly Arg Ser Thr Arg Tyr Trp
            20                  25                  30

Asp Cys Cys Lys Pro Ser Cys Ser Trp Pro Gly Lys Ala Leu Val Asn
        35                  40                  45
```

```
Gln Pro Val Tyr Ala Arg Asn Ala Asn Phe Gln Arg Ile Thr Asp Pro
         50                  55                  60

Asn Ala Lys Ser Gly Cys Asp Gly Gly Ser Ala Phe Ser Cys Ala Asp
 65                  70                  75                  80

Gln Thr Pro Trp Ala Val Ser Asp Asp Phe Ala Tyr Gly Phe Ala Ala
                 85                  90                  95

Thr Ala Leu Ala Gly Gln Ser Glu Ser Ser Trp Cys Cys Ala Cys Tyr
            100                 105                 110

Glu Leu Thr Phe Thr Ser Gly Pro Val Ala Gly Lys Lys Met Ala Val
            115                 120                 125

Gln Ser Thr Ser Thr Gly Gly Asp Leu Gly Ser Asn His Phe Asp Leu
        130                 135                 140

Asn Met Pro Gly Gly Gly Val Gly Ile Phe Asp Gly Cys Ser Pro Gln
145                 150                 155                 160

Val Gly Gly Leu Ala Gly Gln Arg Tyr Gly Gly Val Ser Ser Arg Ser
                165                 170                 175

Glu Cys Asp Ser Phe Pro Ala Ala Leu Lys Pro Gly Cys Tyr Trp Arg
            180                 185                 190

Tyr Asp Trp Phe Lys Asn Ala Asp Asn Pro Ser Phe Ser Phe Arg Gln
        195                 200                 205

Val Gln Cys Pro Ala Glu Leu Val Ala Arg Thr Gly Cys Arg Arg Asn
    210                 215                 220

Asp Asp Gly Asn Phe Pro Ala Val Gln Ile Pro Ser Ser Ser Thr Ser
225                 230                 235                 240

Ser Pro Val Asn Gln Pro Thr Ser Thr Ser Thr Ser Thr Ser Thr Ser
                245                 250                 255

Thr Ser Ser Pro Pro Val Gln Pro Thr Thr Pro Ser Gly Cys Thr Ala
            260                 265                 270

Glu Arg Trp Ala Gln Cys Gly Gly Asn Gly Trp Ser Gly Cys Thr Thr
        275                 280                 285

Cys Val Ala Gly Ser Thr Cys Thr Lys Ile Asn Asp Trp Tyr His Gln
    290                 295                 300

Cys Leu
305

<210> SEQ ID NO 21
<211> LENGTH: 304
<212> TYPE: PRT
<213> ORGANISM: Geomyces pannorum RF6293

<400> SEQUENCE: 21

Met Ala Leu Ser Lys Leu Thr Leu Leu Ala Leu Leu Pro Leu Phe Leu
1               5                  10                  15

Ala Thr Pro Ser Leu Ala Ala Ser Gly Asn Gly Lys Thr Thr Arg Tyr
                20                  25                  30

Trp Asp Cys Cys Lys Pro Ser Cys Ala Trp Ser Gly Lys Ala Ser Phe
            35                  40                  45

Lys Thr Gly Pro Val Gln Ser Cys Asp Lys Gly Asp Asn Val Leu Ala
        50                  55                  60

Asp Ala Asp Thr Lys Ser Ala Cys Asp Asn Gly Gly Pro Ala Phe Met
65                  70                  75                  80

Cys Ser Asp Glu Ser Pro Trp Ala Val Ser Asp Ser Leu Ala Tyr Gly
                85                  90                  95

Phe Ala Ala Val Ser Ile Ser Gly Gly Thr Glu Ala Ser Trp Cys Cys
```

```
            100                 105                 110
Ala Cys Tyr Glu Leu Thr Phe Thr Ser Gly Pro Val Ser Gly Lys Lys
            115                 120                 125

Met Val Val Gln Ala Thr Asn Thr Gly Gly Asp Leu Gly Gln Asn His
            130                 135                 140

Phe Asp Ile Gly Met Pro Gly Gly Phe Gly Leu Phe Asn Ala Cys
145                 150                 155                 160

Thr Pro Gln Tyr Gly Thr Pro Ser Thr Gly Trp Gly Asn Gln Tyr Gly
                165                 170                 175

Gly Leu Thr Ser Arg Ser Gln Cys Asp Ala Phe Pro Gln Ala Leu Lys
            180                 185                 190

Ala Gly Cys Tyr Trp Arg Phe Asp Trp Phe Gln Asn Ala Asp Asn Pro
            195                 200                 205

Ser Val Ser Phe Lys Ser Val Ala Cys Pro Leu Ala Leu Thr Asn Lys
            210                 215                 220

Ser Gly Cys Val Arg Ser Asp Asp Thr Pro Thr Gly Asp Gly Asn Val
225                 230                 235                 240

Pro Thr Ala Ser Gly Val Ala Pro Ala Ser Ser Thr Ser Ala Gly Thr
                245                 250                 255

Thr Thr Pro Ser Thr Gly Pro Gly Thr Gly Gly Ala Thr Val Ala Lys
            260                 265                 270

Tyr Gly Gln Cys Gly Gly Ser Gly Trp Thr Gly Thr Val Cys Ala
            275                 280                 285

Ser Gly Ser Thr Cys Lys Ala Thr Asn Gln Trp Tyr Ser Gln Cys Leu
            290                 295                 300

<210> SEQ ID NO 22
<211> LENGTH: 282
<212> TYPE: PRT
<213> ORGANISM: Geomyces pannorum RF6293

<400> SEQUENCE: 22

Met Thr Asn Leu Ser Arg Ser Leu Arg His Thr Phe Thr Leu Leu Leu
1               5                   10                  15

Phe Ala Leu Val Phe Ser Ser Val Asp Ala Ile Ser Asp Val Phe Gly
                20                  25                  30

Pro Ser Thr Ala Val Thr Ser Arg Tyr Trp Asp Cys Cys Lys Pro Ser
            35                  40                  45

Cys Gly Trp Ala Asp Lys Gly Asp Phe Val Asp Lys Ser Pro Val Gln
        50                  55                  60

Ser Cys Asp Ile Asn Ala Asn Pro Leu Leu Asp Val Thr Gln Gly Thr
65                  70                  75                  80

Gly Cys Asn Gly Gly Asn Ala Phe Gly Cys Ala Ser Asn Ser Pro Trp
                85                  90                  95

Ala Val Asn Asp Thr Phe Ser Tyr Gly Phe Val Gly Thr Phe Leu Ile
            100                 105                 110

Gly Gly Asp Glu Ser Ser Trp Cys Cys Ser Cys Phe Gln Leu Asn Phe
            115                 120                 125

Thr Ser Gly Ala Val Lys Gly Lys Ser Met Ile Val Gln Ala Ser Asn
        130                 135                 140

Thr Asn Tyr Asp Ser Pro Gly Ala Asn Val Phe Thr Leu Gly Ile Pro
145                 150                 155                 160

Gly Gly Asn Thr Ser Tyr Ala Gly Ala Cys Ala Ile Glu Tyr Asn Val
                165                 170                 175
```

```
Pro Asn Ser Val Phe Gly Thr Glu Asn Val Gly Val Ser Asn Arg Thr
            180                 185                 190

Asp Cys Asp Asp Phe Pro Ala Ala Leu Lys Pro Gly Cys Gln Trp Arg
        195                 200                 205

Phe Asp Trp Phe Lys Asp Ala Val Glu Pro Ser Val Glu Tyr Lys Arg
        210                 215                 220

Val Ala Cys Pro Lys Val Leu Thr Asp Ile Thr His Cys Lys Arg Asn
225                 230                 235                 240

Asp Asp Asp Thr Val Asp Glu Asp Ala Ile Lys Ala Asn Ser Pro Ser
                245                 250                 255

Ala Ala Ser Thr Leu Ser Ser Met Gly Pro Thr Ala Ile Thr Val Leu
            260                 265                 270

Phe Met Trp Trp Met Leu Gln Thr Leu Gly
        275                 280

<210> SEQ ID NO 23
<211> LENGTH: 366
<212> TYPE: PRT
<213> ORGANISM: Fusarium cf. equiseti RF6318

<400> SEQUENCE: 23

Met Arg Ser Phe Ala Leu Leu Ala Leu Val Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Lys Val Asn Ala Pro Ala Leu
        35                  40                  45

Thr Cys Asp Asn Lys Asp Asn Pro Ile Thr Asn Thr Asn Ser Val Asn
    50                  55                  60

Gly Cys Glu Gly Gly Gly Ser Ala Tyr Ala Cys Thr Asn Tyr Ser Pro
65                  70                  75                  80

Trp Ala Val Asn Asp Asp Leu Ala Tyr Gly Phe Thr Ala Thr Lys Leu
                85                  90                  95

Ala Gly Gly Thr Glu Ala Ser Trp Cys Cys Ala Cys Tyr Ala Leu Thr
            100                 105                 110

Phe Thr Thr Gly Pro Val Lys Gly Lys Lys Met Ile Val Gln Ser Thr
        115                 120                 125

Asn Thr Gly Gly Asp Leu Gly Asp Asn His Phe Asp Leu Met Met Pro
    130                 135                 140

Gly Gly Gly Val Gly Ile Phe Asp Gly Cys Thr Ser Gln Phe Gly Lys
145                 150                 155                 160

Ala Leu Gly Gly Ala Gln Tyr Gly Gly Ile Ser Ser Arg Ser Glu Cys
                165                 170                 175

Asp Ser Phe Pro Glu Leu Leu Lys Asp Gly Cys His Trp Arg Phe Asp
            180                 185                 190

Trp Phe Lys Asn Ala Asp Asn Pro Asp Phe Thr Phe Glu Gln Val Gln
        195                 200                 205

Cys Pro Lys Glu Leu Leu Ala Ile Ser Gly Cys Lys Arg Asp Asp Asp
    210                 215                 220

Ser Ser Phe Pro Ala Phe Ser Gly Asn Thr Thr Pro Ser Lys Ala Lys
225                 230                 235                 240

Pro Ser Gly Lys Lys Thr Thr Ala Ala Ala Gln Pro Gln Lys Thr Glu
                245                 250                 255

Gln Ala Val Pro Val Val Gln Lys Pro Ala Ala Thr Lys Pro Ala Ser
            260                 265                 270
```

```
Glu Pro Val Ser Lys Pro Ala Val Ser Lys Pro Ala Ala Asp
            275                 280                 285

Pro Thr Lys Val Val Ser Lys Pro Lys Ser Thr Ser Lys Val Gly Gly
                290                 295                 300

Thr Lys Thr His Lys Asp Cys Pro Ala Thr Lys Pro Thr Lys Pro Ala
305                 310                 315                 320

Ala Pro Gln Lys Ser Ala Val Ala Met Tyr Tyr Gln Cys Gly Gly Ser
                325                 330                 335

Lys Ser Ala Tyr Pro Asp Gly Asn Leu Pro Cys Ala Ser Gly Ser Lys
                340                 345                 350

Cys Val Lys Met Asn Asp Tyr Tyr Ser Gln Cys Val Pro Asn
                355                 360                 365

<210> SEQ ID NO 24
<211> LENGTH: 304
<212> TYPE: PRT
<213> ORGANISM: Geomyces pannorum RF6546

<400> SEQUENCE: 24

Met Ala Leu Ser Lys Arg Thr Leu Leu Ala Leu Leu Pro Phe Phe Leu
1               5                   10                  15

Ala Val Pro Ser Leu Ala Val Ser Gly Thr Gly Lys Thr Thr Arg Tyr
                20                  25                  30

Trp Asp Cys Cys Lys Pro Ser Cys Gly Trp Thr Gly Lys Ala Thr Leu
            35                  40                  45

Thr Ser Gly Pro Val Gln Ser Cys Asp Lys Asn Asp Asn Val Leu Ala
        50                  55                  60

Asp Pro Asp Thr Lys Ser Ala Cys Asp Asn Gly Gly Pro Ala Phe Met
65                  70                  75                  80

Cys Ser Asn Glu Ser Pro Trp Ala Val Ser Asp Ser Leu Ala Tyr Gly
                85                  90                  95

Tyr Ala Ala Val Ser Ile Ala Gly Gly Thr Glu Ala Ser Trp Cys Cys
                100                 105                 110

Ala Cys Tyr Glu Leu Thr Phe Thr Ser Gly Pro Val Ser Gly Lys Lys
            115                 120                 125

Met Ile Val Gln Ala Thr Asn Thr Gly Gly Asp Leu Gly Gln Asn His
        130                 135                 140

Phe Asp Ile Gly Met Pro Gly Gly Phe Gly Ile Phe Asn Ala Cys
145                 150                 155                 160

Thr Pro Gln Tyr Gly Thr Pro Ser Thr Gly Trp Gly Ala Gln Tyr Gly
                165                 170                 175

Gly Ile Ser Ser Arg Ser Gln Cys Asp Ala Phe Pro Glu Lys Leu Lys
            180                 185                 190

Ala Gly Cys Tyr Trp Arg Phe Asp Trp Phe Gln Asn Ala Asp Asn Pro
            195                 200                 205

Ser Val Ser Phe Gln Ser Val Ala Cys Pro Leu Ala Ile Thr Asn Lys
            210                 215                 220

Ser Gly Cys Val Arg Ala Asp Asp Lys Pro Thr Gly Gly Thr Val
225                 230                 235                 240

Pro Thr Val Ser Gly Gly Ala Pro Ala Thr Ser Gly Pro Gly
                245                 250                 255

Thr Thr Thr Pro Ser Ser Gly Thr Gly Asn Gly Gly Thr Val Ala Lys
            260                 265                 270

Tyr Ala Gln Cys Gly Gly Asn Gly Trp Thr Gly Gly Thr Val Cys Glu
```

Ala Gly Ser Thr Cys Lys Ala Thr Asn Glu Trp Tyr Ala Gln Cys Leu
            290                 295                 300

<210> SEQ ID NO 25
<211> LENGTH: 304
<212> TYPE: PRT
<213> ORGANISM: Geomyces pannorum RF6608

<400> SEQUENCE: 25

Met Ala Leu Ser Lys Leu Thr Leu Leu Ala Leu Leu Pro Phe Phe Leu
1               5                   10                  15

Ala Ala Pro Ser Leu Ala Val Ser Gly Thr Gly Gln Thr Thr Arg Tyr
            20                  25                  30

Trp Asp Cys Cys Lys Pro Ser Cys Ala Trp Thr Gly Lys Ala Ser Leu
        35                  40                  45

Thr Ser Gly Pro Val Gln Ala Cys Asp Lys Asn Asp Asn Val Leu Ala
    50                  55                  60

Asp Ala Asp Thr Lys Ser Ala Cys Asp Asn Gly Gly Pro Ala Tyr Met
65                  70                  75                  80

Cys Ser Asp Glu Ser Pro Trp Ala Val Ser Asp Ser Leu Ala Tyr Gly
                85                  90                  95

Tyr Ala Ala Val Ser Ile Ala Gly Gly Thr Glu Ala Ser Trp Cys Cys
            100                 105                 110

Ala Cys Tyr Glu Leu Thr Phe Thr Ser Gly Pro Val Ser Gly Lys Lys
        115                 120                 125

Met Ile Val Gln Ala Thr Asn Thr Gly Gly Asp Leu Gly Gln Asn Gln
    130                 135                 140

Phe Asp Leu Gly Met Pro Gly Gly Gly Phe Gly Leu Phe Asn Ala Cys
145                 150                 155                 160

Thr Pro Gln Tyr Gly Thr Pro Ser Thr Gly Trp Gly Ala Gln Tyr Gly
                165                 170                 175

Gly Ile Ser Ser Arg Ser Gln Cys Asp Ala Phe Pro Thr Ala Leu Lys
            180                 185                 190

Ala Gly Cys Tyr Trp Arg Phe Asp Trp Phe Gln Asn Ala Asp Asn Pro
        195                 200                 205

Thr Val Ser Phe Gln Ser Val Ala Cys Pro Leu Ala Leu Thr Asn Lys
    210                 215                 220

Ser Gly Cys Val Arg Ala Asp Asp Thr Pro Thr Gly Ser Gly Thr Val
225                 230                 235                 240

Ser Thr Ala Ser Gly Gly Gly Ala Val Ser Ser Thr Ser Ala Gly Thr
                245                 250                 255

Thr Thr Pro Ser Ser Gly Thr Gly Thr Gly Gly Ala Thr Val Ala Lys
            260                 265                 270

Phe Gly Gln Cys Gly Gly Ser Gly Trp Thr Gly Gly Thr Thr Cys Ala
        275                 280                 285

Ala Gly Ser Thr Cys Gln Val Asn Asn Gln Trp Tyr Ser Gln Cys Leu
    290                 295                 300

<210> SEQ ID NO 26
<211> LENGTH: 282
<212> TYPE: PRT
<213> ORGANISM: Geomyces pannorum RF6608

<400> SEQUENCE: 26

Met Thr Asn Leu Ser Arg Ser Leu Arg His Ile Phe Ala Val Leu Leu

```
              1               5                  10                 15
          Phe Ala Leu Val Phe Ser Cys Val Asp Ala Val Ser Asp Val Phe Gly
                          20                  25                  30

Pro Ser Thr Ala Val Thr Ser Arg Tyr Trp Asp Cys Cys Lys Pro Ser
                      35                  40                  45

Cys Gly Trp Ala Asp Lys Ala Asp Phe Val Asp Lys Ser Pro Val Gln
                  50                  55                  60

Ser Cys Asp Lys Asn Ala Asn Pro Leu Leu Asp Asn Ser Gln Gly Thr
          65                  70                  75                  80

Gly Cys Asn Gly Gly Asn Ala Phe Gly Cys Ala Ser Asn Ser Pro Trp
                              85                  90                  95

Ala Val Asn Asp Thr Phe Ser Tyr Gly Phe Val Gly Thr Phe Leu Val
                          100                 105                 110

Gly Gly Asp Glu Ser Ser Trp Cys Cys Ser Cys Tyr Gln Leu Asn Phe
                      115                 120                 125

Thr Ser Gly Ala Val Lys Gly Lys Ser Met Ile Val Gln Ala Ser Asn
                  130                 135                 140

Thr Asn Tyr Asp Ser Pro Asn Ala Asn Val Phe Thr Leu Gly Ile Pro
          145                 150                 155                 160

Gly Gly Asn Thr Ser Tyr Ala Gly Ala Cys Ala Leu Glu Tyr Ser Val
                              165                 170                 175

Pro Asn Ser Val Phe Gly Thr Glu Asn Val Gly Val Ser Asn Arg Thr
                          180                 185                 190

Asp Cys Asp Asn Leu Pro Ala Ala Leu Lys Pro Gly Cys Gln Trp Arg
                      195                 200                 205

Phe Asp Trp Phe Lys Asp Thr Glu Gly Pro Ser Val Glu Tyr Lys Arg
                  210                 215                 220

Val Thr Cys Pro Lys Val Leu Thr Asp Ile Thr His Cys Lys Arg Glu
          225                 230                 235                 240

Asp Asp Glu Arg Val Glu Glu Asp Ala Ile Lys Ala Asn Ser Pro Ser
                              245                 250                 255

Ala Ala Ser Ala Leu Pro Ser Met Val Pro Thr Ala Ile Ser Ala Ile
                          260                 265                 270

Phe Met Trp Trp Met Leu Gln Thr Leu Gly
                      275                 280

<210> SEQ ID NO 27
<211> LENGTH: 316
<212> TYPE: PRT
<213> ORGANISM: Staphylotrichum coccosporum

<400> SEQUENCE: 27

Met Arg Ser Ser Pro Val Leu Arg Thr Ala Leu Ala Ala Ala Leu Pro
1               5                  10                  15

Leu Ala Ala Leu Ala Ala Asp Gly Lys Ser Thr Arg Tyr Trp Asp Cys
            20                  25                  30

Cys Lys Pro Ser Cys Ser Trp Pro Gly Lys Ala Ser Val Asn Gln Pro
        35                  40                  45

Val Phe Ala Cys Ser Ala Asn Phe Gln Arg Ile Ser Asp Pro Asn Val
    50                  55                  60

Lys Ser Gly Cys Asp Gly Gly Ser Ala Tyr Ala Cys Ala Asp Gln Thr
65                  70                  75                  80

Pro Trp Ala Val Asn Asp Asn Phe Ser Tyr Gly Phe Ala Ala Thr Ser
                85                  90                  95
```

```
Ile Ser Gly Gly Asn Glu Ala Ser Trp Cys Cys Gly Cys Tyr Glu Leu
                100                 105                 110

Thr Phe Thr Ser Gly Pro Val Ala Gly Lys Thr Met Val Val Gln Ser
            115                 120                 125

Thr Ser Thr Gly Gly Asp Leu Gly Thr Asn His Phe Asp Leu Ala Met
        130                 135                 140

Pro Gly Gly Gly Val Gly Ile Phe Asp Gly Cys Ser Pro Gln Phe Gly
145                 150                 155                 160

Gly Leu Ala Gly Asp Arg Tyr Gly Gly Val Ser Ser Arg Ser Gln Cys
                165                 170                 175

Asp Ser Phe Pro Ala Ala Leu Lys Pro Gly Cys Tyr Trp Arg Phe Asp
            180                 185                 190

Trp Phe Lys Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
210                 215                 220

Gly Asn Phe Pro Val Phe Thr Pro Pro Ser Gly Gly Gln Ser Ser Ser
225                 230                 235                 240

Ser Ser Ser Ser Ser Ala Lys Pro Thr Ser Thr Ser Thr Ser Thr
                245                 250                 255

Thr Ser Thr Lys Ala Thr Ser Thr Ser Thr Ala Ser Ser Gln Thr
        260                 265                 270

Ser Ser Ser Thr Gly Gly Cys Ala Ala Gln Arg Trp Ala Gln Cys
    275                 280                 285

Gly Gly Ile Gly Phe Ser Gly Cys Thr Thr Cys Val Ser Gly Thr Thr
        290                 295                 300

Cys Asn Lys Gln Asn Asp Trp Tyr Ser Gln Cys Leu
305                 310                 315

<210> SEQ ID NO 28
<211> LENGTH: 235
<212> TYPE: PRT
<213> ORGANISM: Melanocarpus albomyces

<400> SEQUENCE: 28

Met Arg Ser Thr Pro Val Leu Arg Ala Leu Leu Ala Ala Ala Leu Pro
1               5                   10                  15

Leu Gly Ala Leu Ala Ala Asn Gly Gln Ser Thr Arg Tyr Trp Asp Cys
            20                  25                  30

Cys Lys Pro Ser Cys Gly Trp Arg Gly Lys Gly Pro Val Asn Gln Pro
        35                  40                  45

Val Tyr Ser Cys Asp Ala Asn Phe Gln Arg Ile His Asp Phe Asp Ala
50                  55                  60

Val Ser Gly Cys Glu Gly Gly Pro Ala Phe Ser Cys Ala Asp His Ser
65                  70                  75                  80

Pro Trp Ala Ile Asn Asp Asn Leu Ser Tyr Gly Phe Ala Ala Thr Ala
                85                  90                  95

Leu Ser Gly Gln Thr Glu Glu Ser Trp Cys Cys Ala Cys Tyr Ala Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Ser Asn His Phe Asp Leu Asn Ile
    130                 135                 140

Pro Gly Gly Gly Val Gly Leu Phe Asp Gly Cys Thr Pro Gln Phe Gly
145                 150                 155                 160
```

Gly Leu Pro Gly Ala Arg Tyr Gly Gly Ile Ser Ser Arg Gln Glu Cys
              165                 170                 175

Asp Ser Phe Pro Glu Pro Leu Lys Pro Gly Cys Gln Trp Arg Phe Asp
              180                 185                 190

Trp Phe Gln Asn Ala Asp Asn Pro Ser Phe Thr Phe Glu Arg Val Gln
              195                 200                 205

Cys Pro Glu Glu Leu Val Ala Arg Thr Gly Cys Arg Arg His Asp Asp
              210                 215                 220

Gly Gly Phe Ala Val Phe Lys Ala Pro Ser Ala
225                 230                 235

<210> SEQ ID NO 29
<211> LENGTH: 302
<212> TYPE: PRT
<213> ORGANISM: Podospora anserina

<400> SEQUENCE: 29

Met Arg Ser Ser Thr Val Leu Gln Thr Ser Leu Leu Ala Val Leu Pro
1               5                   10                  15

Leu Ala Val Gln Ala Gln Gly Ala Ser Gly Ser Gly Lys Ser Thr Arg
                20                  25                  30

Tyr Trp Asp Cys Cys Lys Pro Ser Cys Ala Trp Pro Gly Lys Ala Ala
            35                  40                  45

Val Asn Arg Pro Val Phe Ala Cys Asp Ala Asn Phe Gln Arg Ile Ser
        50                  55                  60

Asp Ser Gly Val Ala Ser Gly Cys Asn Gly Gly Ser Ala Tyr Ser Cys
65                  70                  75                  80

Ala Asp His Ser Ala Trp Ala Ile Asn Asp Asn Leu Ser Tyr Gly Phe
                85                  90                  95

Ala Ala Thr Ala Leu Ser Gly Gly Ser Glu Ala Ser Trp Cys Cys Ala
            100                 105                 110

Cys Tyr Glu Leu Thr Phe Thr Asp Gly Pro Val Ala Gly Lys Lys Met
            115                 120                 125

Val Val Gln Ser Thr Ser Thr Gly Gly Asp Leu Gly Ser Asn His Phe
        130                 135                 140

Asp Leu Asn Ile Pro Gly Gly Val Gly Leu Phe Asp Gly Cys Lys
145                 150                 155                 160

Pro Gln Phe Gly Gly Leu Pro Gly Ala Thr Tyr Gly Gly Ile Ser Asp
                165                 170                 175

Arg Ser Gln Cys Ala Ser Phe Pro Asp Ala Leu Lys Pro Gly Cys Asn
            180                 185                 190

Trp Arg Phe Asp Trp Phe Lys Asn Ala Asp Asn Pro Ser Phe Thr Phe
            195                 200                 205

Arg Gln Val Gln Cys Pro Ser Glu Leu Thr Ala Arg Ser Gly Cys Lys
        210                 215                 220

Arg Asp Asp Asp Ser Arg Phe Pro Val Phe Ser Pro Gly Gly Gly
225                 230                 235                 240

Ser Gln Pro Gln Pro Gln Pro Thr Ser Ser Ala Ala Gln Asn Pro Asn
                245                 250                 255

Pro Thr Pro Ser Ala Ala Pro Gly Gly Cys Arg Ala Ala Lys Tyr Ala
            260                 265                 270

Gln Cys Gly Gly Gln Gly Phe Thr Gly Cys Thr Thr Cys Glu Ala Gly
        275                 280                 285

Ser Thr Cys Thr Ala Ser Asn Gln Trp Tyr Ser Gln Cys Leu

<210> SEQ ID NO 30
<211> LENGTH: 315
<212> TYPE: PRT
<213> ORGANISM: Acremonium thermophilum

<400> SEQUENCE: 30

Met Arg Ser Ser Pro Phe Leu Arg Ala Ala Ala Ala Leu Pro
1               5                   10                  15

Leu Ser Ala His Ala Leu Asp Gly Lys Ser Thr Arg Tyr Trp Asp Cys
            20                  25                  30

Cys Lys Pro Ser Cys Gly Trp Ala Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Val Pro Gly Leu Asp Gly
225                 230                 235                 240

Ser Asn Pro Gly Asn Pro Thr Thr Val Val Pro Ala Ser Thr
                245                 250                 255

Ser Thr Ser Arg Pro Thr Ser Ser Thr Ser Ser Pro Val Ser Thr Pro
            260                 265                 270

Thr Gly Gln Pro Gly Gly Cys Thr Thr Gln Lys Trp Gly Gln Cys Gly
        275                 280                 285

Gly Ile Gly Tyr Thr Gly Cys Thr Asn Cys Val Ala Gly Thr Thr Cys
    290                 295                 300

Thr Gln Leu Asn Pro Trp Tyr Ser Gln Cys Leu
305                 310                 315

<210> SEQ ID NO 31
<211> LENGTH: 307
<212> TYPE: PRT
<213> ORGANISM: Trichothecium roseum

<400> SEQUENCE: 31

Pro Phe Met Met Val Ala Trp Trp Ser Leu Phe Leu Tyr Gly Leu Gln

```
            1               5                  10                 15
        Val Ala Ala Pro Ala Phe Ala Ala Asp Gly Arg Ser Thr Arg Tyr Trp
                         20                 25                 30

Asp Cys Cys Lys Pro Ser Cys Ser Trp Pro Asp Lys Ala Pro Val Gly
                     35                 40                 45

Ser Pro Val Gly Thr Cys Asp Ala Gly Asn Ser Pro Leu Gly Asp Pro
                 50                 55                 60

Leu Ala Lys Ser Gly Cys Glu Gly Gly Pro Ser Tyr Thr Cys Ala Asn
        65                 70                 75                 80

Tyr Gln Pro Trp Ala Val Asn Asp Gln Leu Ala Tyr Gly Phe Ala Ala
                         85                 90                 95

Thr Ala Ile Asn Gly Gly Thr Glu Asp Ser Trp Cys Cys Ala Cys Tyr
                     100                105                110

Lys Leu Thr Phe Thr Asp Gly Pro Ala Ser Gly Lys Thr Met Ile Val
                     115                120                125

Gln Ser Thr Asn Thr Gly Gly Asp Leu Ser Asp Asn His Phe Asp Leu
                     130                135                140

Leu Ile Pro Gly Gly Gly Val Gly Ile Phe Asp Gly Cys Thr Ser Gln
        145                150                155                160

Tyr Gly Gln Ala Leu Pro Gly Ala Gln Tyr Gly Gly Val Ser Ser Arg
                         165                170                175

Ala Glu Cys Asp Gln Met Pro Glu Ala Ile Lys Ala Gly Cys Gln Trp
                     180                185                190

Arg Tyr Asp Trp Phe Lys Asn Ala Asp Asn Pro Ser Phe Ser Phe Arg
                     195                200                205

Gln Val Gln Cys Pro Ala Glu Leu Val Ala Arg Thr Gly Cys Arg Arg
                     210                215                220

Asn Asp Asp Gly Asn Phe Pro Ala Val Gln Ile Pro Ser Ser Ser Thr
        225                230                235                240

Ser Ser Pro Val Asn Gln Pro Thr Ser Thr Ser Thr Ser Thr Ser Ser
                         245                250                255

Thr Thr Ser Ser Pro Pro Val Gln Pro Thr Thr Pro Ser Gly Cys Thr
                     260                265                270

Ala Glu Arg Trp Ala Gln Cys Gly Gly Asn Gly Trp Ser Gly Cys Thr
                     275                280                285

Thr Cys Val Ala Gly Ser Thr Cys Thr Lys Ile Asn Asp Trp Tyr His
                     290                295                300

Gln Cys Leu
        305

<210> SEQ ID NO 32
<211> LENGTH: 297
<212> TYPE: PRT
<213> ORGANISM: Acremonium thermophilum

<400> SEQUENCE: 32

Met Arg Ser Ser Pro Phe Leu Arg Ala Ala Leu Ala Ala Ala Leu Pro
1               5                  10                 15

Leu Ser Ala His Ala Leu Asp Gly Lys Ser Thr Arg Tyr Trp Asp Cys
            20                 25                 30

Cys Lys Pro Ser Cys Gly Trp Pro Gly Lys Ala Ser Val Asn Gln Pro
        35                 40                 45

Val Phe Ser Cys Ser Ala Asp Trp Gln Arg Ile Ser Asp Phe Asn Ala
    50                 55                 60
```

```
Lys Ser Gly Cys Asp Gly Ser Ala Tyr Ser Cys Ala Asp Gln Thr
 65                  70                  75                  80

Pro Trp Ala Val Asn Asp Asn Phe Ser Tyr Gly Phe Ala Ala Thr Ala
                 85                  90                  95

Ile Ala Gly Gly Ser Glu Ser Ser Trp Cys Cys Ala Cys Tyr Ala Leu
                100                 105                 110

Thr Phe Asn Ser Gly Pro Val Ala Gly Lys Thr Met Val Val Gln Ser
            115                 120                 125

Thr Ser Thr Gly Gly Asp Leu Gly Ser Asn Gln Phe Asp Leu Ala Ile
130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
210                 215                 220

Ala Ser Tyr Pro Val Phe Asn Pro Pro Ser Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
                260                 265                 270

Gly Phe Thr Gly Cys Thr Thr Cys Val Ser Gly Thr Thr Cys Gln Val
            275                 280                 285

Gln Asn Gln Trp Tyr Ser Gln Cys Leu
        290                 295

<210> SEQ ID NO 33
<211> LENGTH: 308
<212> TYPE: PRT
<213> ORGANISM: Fusarium anguioides

<400> SEQUENCE: 33

Pro Phe Met Met Val Ala Trp Trp Ser Leu Phe Leu Tyr Gly Leu Gln
  1               5                  10                  15

Val Ala Ala Pro Ala Phe Ala Ala Asp Gly Arg Ser Thr Arg Tyr Trp
                 20                  25                  30

Asp Cys Cys Lys Pro Ser Cys Ser Trp Gly Gly Lys Ala Ala Val Ser
             35                  40                  45

Ala Pro Ala Leu Thr Cys Asp Lys Lys Asp Asn Pro Ile Ser Asn Leu
 50                  55                  60

Asn Ala Val Asn Gly Cys Glu Gly Gly Ser Ala Phe Ala Cys Thr
 65                  70                  75                  80

Asn Tyr Ser Pro Trp Ala Val Asn Asp Asn Leu Ala Tyr Gly Phe Ala
                 85                  90                  95

Ala Thr Lys Leu Ala Gly Gly Ser Glu Gly Ser Trp Cys Cys Ala Cys
                100                 105                 110

Tyr Ala Leu Thr Phe Thr Thr Gly Pro Val Lys Gly Lys Thr Met Val
            115                 120                 125

Val Gln Ser Thr Asn Thr Gly Gly Asp Leu Gly Asp Asn His Phe Asp
130                 135                 140
```

```
Leu Met Met Pro Gly Gly Gly Val Gly Ile Phe Asp Gly Cys Thr Ser
145                 150                 155                 160

Gln Phe Gly Lys Ala Leu Gly Gly Ala Gln Tyr Gly Gly Ile Ser Ser
            165                 170                 175

Arg Ser Glu Cys Asp Ser Phe Pro Glu Thr Leu Lys Asp Gly Cys His
        180                 185                 190

Trp Arg Phe Asp Trp Phe Lys Asn Ala Asp Asn Pro Ser Phe Ser Phe
        195                 200                 205

Arg Gln Val Gln Cys Pro Ala Glu Leu Val Ala Arg Thr Gly Cys Arg
    210                 215                 220

Arg Asn Asp Asp Gly Asn Phe Pro Ala Val Gln Ile Pro Ser Ser Ser
225                 230                 235                 240

Thr Ser Ser Pro Val Asn Gln Pro Thr Ser Thr Ser Thr Thr Ser Thr
            245                 250                 255

Ser Thr Thr Ser Ser Pro Pro Val Gln Pro Thr Thr Pro Ser Gly Cys
        260                 265                 270

Thr Ala Glu Arg Trp Ala Gln Cys Gly Gly Asn Gly Trp Ser Gly Cys
    275                 280                 285

Thr Thr Cys Val Ala Gly Ser Thr Cys Thr Lys Ile Asn Asp Trp Tyr
    290                 295                 300

His Gln Cys Leu
305

<210> SEQ ID NO 34
<211> LENGTH: 304
<212> TYPE: PRT
<213> ORGANISM: Clonostachys rosea f. catenulata

<400> SEQUENCE: 34

Met Met Val Ala Trp Trp Ser Leu Phe Leu Tyr Gly Leu Gln Val Ala
1               5                   10                  15

Ala Pro Ala Phe Ala Ala Asp Gly Arg Ser Thr Arg Tyr Trp Asp Cys
            20                  25                  30

Cys Lys Pro Ser Cys Ala Trp Ser Gly Lys Ala Ser Val Ser Ser Pro
        35                  40                  45

Val Arg Thr Cys Asp Ala Asn Asn Ser Pro Leu Ser Asp Val Asp Ala
    50                  55                  60

Lys Ser Ala Cys Asp Gly Gly Val Ala Tyr Thr Cys Ser Asn Asn Ala
65                  70                  75                  80

Pro Trp Ala Val Asn Asp Asn Leu Ser Tyr Gly Phe Ala Ala Thr Ala
                85                  90                  95

Ile Asn Gly Gly Ser Glu Ser Ser Trp Cys Cys Ala Cys Tyr Lys Leu
            100                 105                 110

Thr Phe Thr Ser Gly Pro Ala Ser Gly Lys Val Met Val Val Gln Ser
        115                 120                 125

Thr Asn Thr Gly Tyr Asp Leu Ser Asn Asn His Phe Asp Ile Leu Met
    130                 135                 140

Pro Gly Gly Gly Val Gly Ala Phe Asp Gly Cys Ser Arg Gln Tyr Gly
145                 150                 155                 160

Ser Ile Pro Gly Glu Arg Tyr Gly Gly Val Thr Ser Arg Asp Gln Cys
                165                 170                 175

Asp Gln Met Pro Ser Ala Leu Lys Gln Gly Cys Tyr Trp Arg Phe Asp
            180                 185                 190

Trp Phe Lys Asn Ala Asp Asn Pro Ser Phe Ser Phe Arg Gln Val Gln
```

```
            195                 200                 205
Cys Pro Ala Glu Leu Val Ala Arg Thr Gly Cys Arg Arg Asn Asp Asp
210                 215                 220

Gly Asn Phe Pro Ala Val Gln Ile Pro Ser Ser Thr Ser Ser Pro
225                 230                 235                 240

Val Asn Gln Pro Thr Ser Thr Ser Thr Ser Thr Ser Thr Thr Ser
                    245                 250                 255

Ser Pro Pro Val Gln Pro Thr Thr Pro Ser Gly Cys Thr Ala Glu Arg
                260                 265                 270

Trp Ala Gln Cys Gly Gly Asn Gly Trp Ser Gly Cys Thr Thr Cys Val
                275                 280                 285

Ala Gly Ser Thr Cys Thr Lys Ile Asn Asp Trp Tyr His Gln Cys Leu
290                 295                 300
```

<210> SEQ ID NO 35
<211> LENGTH: 293
<212> TYPE: PRT
<213> ORGANISM: Neurospora crassa

<400> SEQUENCE: 35

```
Met Arg Ser Ser Thr Ile Leu Gln Thr Gly Leu Val Ala Ala Leu Pro
1               5                   10                  15

Phe Ala Val Gln Ala Ala Ser Gly Ser Gly Gln Ser Thr Arg Tyr Trp
                20                  25                  30

Asp Cys Cys Lys Pro Ser Cys Ser Trp Ser Gly Lys Ala Pro Val Asn
                35                  40                  45

Arg Pro Val Leu Ala Cys Asp Ala Asn Asn Asn Pro Leu Ser Asp Ala
50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
                100                 105                 110

Ala Leu Thr Phe Thr Ser Gly Pro Val Ala Gly Lys Thr Leu Val Val
                115                 120                 125

Gln Ser Thr Ser Thr Gly Gly Asp Leu Gly Ser Asn His Phe Asp Ile
130                 135                 140

Asn Met Pro Gly Gly Gly Val Gly Leu Phe Asp Gly Cys Lys Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
                180                 185                 190

Phe Asp Trp Phe Gln Asn Ala Asp Asn Pro Asn Phe Thr Phe Lys Gln
                195                 200                 205

Val Gln Cys Pro Ser Glu Leu Thr Ser Arg Thr Gly Cys Lys Arg Asn
                210                 215                 220

Asp Asp Ser Gln Phe Pro Val Phe Thr Pro Ser Gly Gly Ser
225                 230                 235                 240

Asn Pro Ser Thr Pro Thr Thr Pro Ser Ser Gly Gly Ser Gly
                245                 250                 255

Cys Thr Ala Asp Lys Tyr Ala Gln Cys Gly Gly Ser Gly Trp Ser Gly
                260                 265                 270
```

```
Cys Thr Asn Cys Pro Ser Gly Ser Thr Cys Lys Thr Ile Asn Asp Tyr
        275                 280                 285

Tyr His Gln Cys Ala
    290

<210> SEQ ID NO 36
<211> LENGTH: 310
<212> TYPE: PRT
<213> ORGANISM: Volutella colletotrichoides

<400> SEQUENCE: 36

Met Arg Ser Ser Ala Val Leu Ile Gly Leu Val Ala Gly Val Ala Ala
1               5                   10                  15

Gln Ser Ser Gly Thr Gly Arg Thr Thr Arg Tyr Trp Asp Cys Cys Lys
            20                  25                  30

Pro Ser Cys Gly Trp Asp Glu Lys Ala Ser Val Ser Gln Pro Val Lys
        35                  40                  45

Thr Cys Asp Arg Asn Asn Asn Pro Leu Ala Ser Thr Ala Arg Ser Gly
    50                  55                  60

Cys Asp Ser Asn Gly Val Ala Tyr Thr Cys Asn Asp Asn Gln Pro Trp
65                  70                  75                  80

Ala Val Asn Asp Asn Leu Ala Tyr Gly Phe Ala Ala Thr Ala Phe Ser
                85                  90                  95

Gly Gly Ser Glu Ala Ser Trp Cys Cys Ala Cys Tyr Ala Leu Gln Phe
            100                 105                 110

Thr Ser Gly Pro Val Ala Gly Lys Thr Met Val Val Gln Ser Thr Asn
        115                 120                 125

Thr Gly Gly Asp Leu Ser Gly Asn His Phe Asp Ile Leu Met Pro Gly
    130                 135                 140

Gly Gly Leu Gly Ile Phe Asp Gly Cys Thr Pro Gln Trp Gly Val Ser
145                 150                 155                 160

Phe Pro Gly Asn Arg Tyr Gly Gly Thr Thr Ser Arg Ser Gln Cys Ser
                165                 170                 175

Gln Ile Pro Ser Ala Leu Gln Pro Gly Cys Asn Trp Arg Tyr Asp Trp
            180                 185                 190

Phe Asn Asp Ala Asp Asn Pro Asp Val Ser Trp Arg Arg Val Gln Cys
        195                 200                 205

Pro Ala Ala Leu Thr Asp Arg Thr Gly Cys Arg Arg Ser Asp Asp Gly
    210                 215                 220

Asn Tyr Pro Val Phe Gln Pro Gly Pro Pro Pro Ala Thr Thr Ile Arg
225                 230                 235                 240

Thr Ser Thr Thr Ile Thr Ala Ser Ser Ser Ser Ser Ser Ser Ser Ser
                245                 250                 255

Ser Thr Thr Ala Gly Ser Pro Pro Val Pro Thr Gly Gly Gly Ser Gly
            260                 265                 270

Pro Thr Ser Pro Val Trp Gly Gln Cys Gly Gly Gln Gly Trp Ser Gly
        275                 280                 285

Pro Thr Arg Cys Val Ala Gly Ser Thr Cys Ser Val Val Asn Pro Trp
    290                 295                 300

Tyr Ser Gln Cys Phe Pro
305                 310

<210> SEQ ID NO 37
<211> LENGTH: 355
<212> TYPE: PRT
<213> ORGANISM: Gibberella zeae
```

<400> SEQUENCE: 37

```
Met Arg Ser Phe Ala Leu Leu Ala Leu Phe Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Lys Val Ser Ala Pro Ala Leu
        35                  40                  45

Thr Cys Asp Lys Lys Asp Asn Pro Ile Thr Asn Leu Asn Ala Val Asn
50                  55                  60

Gly Cys Glu Ser Gly Gly Ser Ala Phe Ala Cys Thr Asn Tyr Ser Pro
65                  70                  75                  80

Trp Ala Val Asn Asp Asp Leu Ala Tyr Gly Phe Thr Ala Thr Lys Leu
                85                  90                  95

Ala Gly Gly Thr Glu Ala Ser Trp Cys Cys Ala Cys Tyr Ala Leu Thr
            100                 105                 110

Phe Thr Thr Gly Pro Val Lys Gly Lys Lys Met Ile Val Gln Ser Thr
        115                 120                 125

Asn Thr Gly Gly Asp Leu Gly Asp Asn His Phe Asp Leu Met Met Pro
130                 135                 140

Gly Gly Gly Val Gly Ile Phe Asp Gly Cys Thr Ser Glu Phe Gly Lys
145                 150                 155                 160

Pro Leu Gly Gly Ala Gln Tyr Gly Gly Ile Ser Ser Arg Ser Gln Cys
                165                 170                 175

Asp Ser Phe Pro Glu Leu Leu Lys Asp Gly Cys His Trp Arg Phe Asp
            180                 185                 190

Trp Phe Lys Asn Ala Asp Asn Pro Asp Phe Thr Phe Glu Gln Val Gln
        195                 200                 205

Cys Pro Lys Glu Leu Leu Ala Ile Ser Gly Cys Lys Arg Asp Asp Asp
210                 215                 220

Ser Ser Phe Pro Ala Phe Lys Gly Asn Thr Thr Pro Ser Asn Ala Lys
225                 230                 235                 240

Pro Ser Gly Glu Lys Ser Ala Ala Ala Gln Pro Gln Lys Pro Ser
                245                 250                 255

Thr Lys Ala Ala Thr Glu Pro Ile Ala Thr Lys Pro Ala Thr Val Lys
            260                 265                 270

Pro Ala Pro Val Lys Pro Thr Lys Val Val Asn Lys Pro Lys Thr Ala
        275                 280                 285

Ser Lys Val Gly Gly Thr Lys Thr Arg Gly Lys Cys Pro Ala Thr Lys
290                 295                 300

Pro Thr Lys Pro Ala Ala Pro Gln Lys Ser Ala Val Ala Ile Tyr His
305                 310                 315                 320

Gln Cys Gly Gly Ser Lys Ser Ala Tyr Pro Asp Gly Ser Leu Ser Cys
                325                 330                 335

Ala Ser Gly Ser Lys Cys Val Lys Met Asn Asp Tyr Tyr Ser Gln Cys
            340                 345                 350

Val Pro Asn
        355
```

<210> SEQ ID NO 38
<211> LENGTH: 376
<212> TYPE: PRT
<213> ORGANISM: Fusarium oxysporum

<400> SEQUENCE: 38

Met Arg Ser Tyr Thr Leu Leu Ala Leu Ala Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Ala Val Asn Ala Pro Ala Leu
        35                  40                  45

Thr Cys Asp Lys Asn Asp Asn Pro Ile Ser Asn Thr Asn Ala Val Asn
    50                  55                  60

Gly Cys Glu Gly Gly Gly Ser Ala Tyr Ala Cys Thr Asn Tyr Ser Pro
65                  70                  75                  80

Trp Ala Val Asn Asp Glu Leu Ala Tyr Gly Phe Ala Ala Thr Lys Ile
                85                  90                  95

Ser Gly Gly Ser Glu Ala Ser Trp Cys Cys Ala Cys Tyr Ala Leu Thr
                100                 105                 110

Phe Thr Thr Gly Pro Val Lys Gly Lys Lys Met Ile Val Gln Ser Thr
            115                 120                 125

Asn Thr Gly Gly Asp Leu Gly Asp Asn His Phe Asp Leu Met Met Pro
130                 135                 140

Gly Gly Gly Val Gly Ile Phe Asp Gly Cys Thr Ser Glu Phe Gly Lys
145                 150                 155                 160

Ala Leu Gly Gly Ala Gln Tyr Gly Gly Ile Ser Ser Arg Ser Glu Cys
                165                 170                 175

Asp Ser Tyr Pro Glu Leu Leu Lys Asp Gly Cys His Trp Arg Phe Asp
            180                 185                 190

Trp Phe Glu Asn Ala Asp Asn Pro Asp Phe Thr Phe Glu Gln Val Gln
            195                 200                 205

Cys Pro Lys Ala Leu Leu Asp Ile Ser Gly Cys Lys Arg Asp Asp Asp
210                 215                 220

Ser Ser Phe Pro Ala Phe Lys Gly Asp Thr Ser Ala Ser Lys Pro Gln
225                 230                 235                 240

Pro Ser Ser Ser Ala Lys Lys Thr Thr Ser Ala Ala Ala Ala Ala Gln
                245                 250                 255

Pro Gln Lys Thr Lys Asp Ser Ala Pro Val Val Gln Lys Ser Ser Thr
            260                 265                 270

Lys Pro Ala Ala Gln Pro Glu Pro Thr Lys Pro Ala Asp Lys Pro Gln
            275                 280                 285

Thr Asp Lys Pro Val Ala Thr Lys Pro Ala Ala Thr Lys Pro Ala Gln
            290                 295                 300

Pro Val Asn Lys Pro Lys Thr Thr Gln Lys Val Arg Gly Thr Lys Thr
305                 310                 315                 320

Arg Gly Ser Cys Pro Ala Lys Thr Asp Ala Thr Ala Lys Ala Ser Val
                325                 330                 335

Val Pro Ala Tyr Tyr Gln Cys Gly Gly Ser Lys Ser Ala Tyr Pro Asn
                340                 345                 350

Gly Asn Leu Ala Cys Ala Thr Gly Ser Lys Cys Val Lys Gln Asn Glu
                355                 360                 365

Tyr Tyr Ser Gln Cys Val Pro Asn
370                 375

<210> SEQ ID NO 39
<211> LENGTH: 349
<212> TYPE: PRT
<213> ORGANISM: Acremonium sp.

<400> SEQUENCE: 39

```
Met Ile Ser Ala Trp Ile Leu Gly Leu Val Gly Ala Val Pro Ser
1               5                   10                  15

Ser Val Met Ala Ala Ser Gly Lys Gly His Thr Thr Arg Tyr Trp Asp
            20                  25                  30

Cys Cys Lys Thr Ser Cys Ala Trp Glu Gly Lys Ala Ser Val Ser Glu
            35                  40                  45

Pro Val Leu Thr Cys Asn Lys Gln Asp Asn Pro Ile Val Asp Ala Asn
        50                  55                  60

Ala Arg Ser Gly Cys Asp Gly Gly Ala Phe Ala Cys Thr Asn Asn
65              70                  75                  80

Ser Pro Trp Ala Val Ser Glu Asp Leu Ala Tyr Gly Phe Ala Ala Thr
                85                  90                  95

Ala Leu Ser Gly Gly Thr Glu Gly Ser Trp Cys Cys Ala Cys Tyr Ala
                100                 105                 110

Ile Thr Phe Thr Ser Gly Pro Val Ala Gly Lys Lys Met Val Val Gln
            115                 120                 125

Ser Thr Asn Thr Gly Gly Asp Leu Ser Asn Asn His Phe Asp Leu Met
130                 135                 140

Ile Pro Gly Gly Gly Leu Gly Ile Phe Asp Gly Cys Ser Ala Gln Phe
145                 150                 155                 160

Gly Gln Leu Leu Pro Gly Glu Arg Tyr Gly Gly Val Ser Ser Arg Ser
                165                 170                 175

Gln Cys Asp Gly Met Pro Glu Leu Leu Lys Asp Gly Cys Gln Trp Arg
            180                 185                 190

Phe Asp Trp Phe Lys Asn Ser Asp Asn Pro Asp Ile Glu Phe Glu Gln
            195                 200                 205

Val Gln Cys Pro Lys Glu Leu Ile Ala Val Ser Gly Cys Val Arg Asp
        210                 215                 220

Asp Asp Ser Ser Phe Pro Val Phe Gln Gly Ser Gly Ser Gly Asp Val
225                 230                 235                 240

Asn Pro Pro Pro Lys Pro Thr Thr Thr Thr Ser Ser Lys Pro Lys
                245                 250                 255

Thr Thr Ser Ala Pro Ser Thr Leu Ser Asn Pro Ser Ala Pro Gln Gln
            260                 265                 270

Pro Gly Asn Thr Asp Arg Pro Ala Glu Thr Thr Thr Lys Leu Pro
            275                 280                 285

Ala Leu Pro Ala Thr Thr Ser Ser Pro Ala Val Ser Val Pro Ser Ser
            290                 295                 300

Ser Ala Arg Val Pro Leu Trp Gly Gln Cys Asp Ser Glu Ala Ser Trp
305                 310                 315                 320

Asp Ala Pro Lys Lys Cys Ala Lys Gly Thr Lys Cys Val Tyr Val Asn
                325                 330                 335

Asp Trp Tyr Ser Gln Cys Gln Pro Lys Asn Ser Cys Ala
            340                 345
```

<210> SEQ ID NO 40
<211> LENGTH: 295
<212> TYPE: PRT
<213> ORGANISM: Acremonium sp.

<400> SEQUENCE: 40

```
Met Arg Ser Thr Ser Ile Leu Ile Gly Leu Val Ala Gly Val Ala Ala
1               5                   10                  15
```

Gln Ser Ser Gly Ser Gly His Thr Thr Arg Tyr Trp Asp Cys Cys Lys
              20                  25                  30

Pro Ser Cys Ala Trp Asp Glu Lys Ala Ala Val Ser Arg Pro Val Thr
             35                  40                  45

Thr Cys Asp Arg Asn Asn Ser Pro Leu Ser Pro Gly Ala Val Ser Gly
     50                  55                  60

Cys Asp Pro Asn Gly Val Ala Phe Thr Cys Asn Asp Asn Gln Pro Trp
65                  70                  75                  80

Ala Val Asn Asn Asn Val Ala Tyr Gly Phe Ala Ala Thr Ala Phe Pro
                 85                  90                  95

Gly Gly Asn Glu Ala Ser Trp Cys Cys Ala Cys Tyr Ala Leu Gln Phe
             100                 105                 110

Thr Ser Gly Pro Val Ala Gly Lys Thr Met Val Val Gln Ser Thr Asn
     115                 120                 125

Thr Gly Gly Asp Leu Ser Gly Thr His Phe Asp Ile Gln Met Pro Gly
130                 135                 140

Gly Gly Leu Gly Ile Phe Asp Gly Cys Thr Pro Gln Phe Gly Phe Thr
145                 150                 155                 160

Phe Pro Gly Asn Arg Tyr Gly Gly Thr Thr Ser Arg Ser Gln Cys Ala
                165                 170                 175

Glu Leu Pro Ser Val Leu Arg Asp Gly Cys His Trp Arg Tyr Asp Trp
            180                 185                 190

Phe Asn Asp Ala Asp Asn Pro Asn Val Asn Trp Arg Arg Val Arg Cys
        195                 200                 205

Pro Ala Ala Leu Thr Asn Arg Ser Gly Cys Val Arg Asn Asp Asp Asn
210                 215                 220

Ser Tyr Pro Val Phe Glu Pro Gly Thr Gly Thr Pro Thr Pro Thr
225                 230                 235                 240

Thr Thr Thr Thr Ser Ser Pro Pro Gln Pro Thr Asn Gly Gly Gly
                245                 250                 255

Gly Thr Ser Pro His Trp Gly Gln Cys Gly Gly Gln Gly Trp Ser Gly
            260                 265                 270

Pro Thr Ala Cys Ala Gly Gly Ser Thr Cys Asn Leu Ile Asn Pro Trp
        275                 280                 285

Tyr Ser Gln Cys Ile Pro Asn
290                 295

<210> SEQ ID NO 41
<211> LENGTH: 225
<212> TYPE: PRT
<213> ORGANISM: Chrysosporium lucknowense

<400> SEQUENCE: 41

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
             20                  25                  30

Cys Lys Pro Ser Cys Ala Trp Pro Gly Lys Gly Pro Ser Ser Pro Val
         35                  40                  45

Gln Ala Cys Asp Lys Asn Asp Asn Pro Leu Asn Asp Gly Gly Ser Thr
     50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

```
Lys Leu Ala Gly Ser Ser Glu Ser Gln Trp Cys Cys Ala Cys Tyr Glu
                100                 105                 110

Leu Thr Phe Thr Ser Gly Pro Val Ala Gly Lys Lys Met Ile Val Gln
            115                 120                 125

Ala Thr Asn Thr Gly Gly Asp Leu Gly Asp Asn His Phe Asp Leu Ala
        130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225

<210> SEQ ID NO 42
<211> LENGTH: 225
<212> TYPE: PRT
<213> ORGANISM: Thielavia heterothallica

<400> SEQUENCE: 42

Met His Leu Ser Ala Thr Thr Gly Phe Leu Ala Leu Pro Val Leu Ala
1               5                   10                  15

Leu Asp Gln Leu Ser Gly Ile Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
                100                 105                 110

Leu Thr Phe Thr Ser Gly Pro Val Ala Gly Lys Lys Met Ile Val Gln
            115                 120                 125

Ala Thr Asn Thr Gly Gly Asp Leu Gly Asp Asn His Phe Asp Leu Ala
        130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
```

<210> SEQ ID NO 43
<211> LENGTH: 338
<212> TYPE: PRT
<213> ORGANISM: Mucor circinelloides

<400> SEQUENCE: 43

Met Lys Phe Thr Val Ala Ile Thr Ser Ile Ala Val Ala Leu Ala Leu
1               5                   10                  15

Ser Ser Ser Ala Glu Ala Ala Ser Cys Ser Ser Val Tyr Gly Gln Cys
            20                  25                  30

Gly Gly Ile Gly Trp Ser Gly Pro Thr Cys Cys Glu Ser Gly Ser Thr
        35                  40                  45

Cys Val Ala Gln Glu Gly Asn Lys Tyr Tyr Ser Gln Cys Leu Pro Gly
    50                  55                  60

Ser His Ser Asn Asn Ala Gly Asn Ala Ser Ser Thr Lys Lys Thr Ser
65                  70                  75                  80

Thr Lys Thr Ser Thr Thr Thr Ala Lys Ala Thr Ala Thr Val Thr Thr
                85                  90                  95

Lys Thr Val Thr Lys Thr Thr Thr Lys Thr Thr Thr Lys Thr Ser Thr
            100                 105                 110

Thr Ala Ala Ser Thr Ser Thr Ser Ser Ser Ala Gly Tyr Lys Val
        115                 120                 125

Ile Ser Gly Gly Lys Ser Gly Ser Gly Ser Thr Thr Arg Tyr Trp Asp
130                 135                 140

Cys Cys Lys Ala Ser Cys Ser Trp Pro Gly Lys Ala Ser Val Thr Gly
145                 150                 155                 160

Pro Val Asp Thr Cys Ala Ser Asn Gly Ile Ser Leu Leu Asp Ala Asn
                165                 170                 175

Ala Gln Ser Gly Cys Asn Gly Gly Asn Gly Phe Met Cys Asn Asn Asn
            180                 185                 190

Gln Pro Trp Ala Val Asn Asp Glu Leu Ala Tyr Gly Phe Ala Ala Ala
        195                 200                 205

Ser Ile Ala Gly Ser Asn Glu Ala Gly Trp Cys Cys Gly Cys Tyr Glu
    210                 215                 220

Leu Thr Phe Thr Ser Gly Ala Ala Ser Gly Lys Lys Met Val Val Gln
225                 230                 235                 240

Val Thr Asn Thr Gly Gly Asp Leu Gly Ser Asn His Phe Asp Leu Gln
                245                 250                 255

Met Pro Gly Gly Gly Val Gly Ile Phe Asn Gly Cys Ala Ala Gln Trp
            260                 265                 270

Gly Ala Pro Asn Asp Gly Trp Gly Ala Arg Tyr Gly Gly Val Ser Ser
        275                 280                 285

Val Ser Asp Cys Ala Ser Leu Pro Ser Ala Leu Gln Ala Gly Cys Lys
    290                 295                 300

Trp Arg Phe Asn Trp Phe Lys Asn Ser Asp Asn Pro Thr Met Thr Phe
305                 310                 315                 320

Lys Glu Val Thr Cys Pro Ala Glu Leu Thr Thr Arg Ser Gly Cys Glu
                325                 330                 335

Arg Lys

<210> SEQ ID NO 44
<211> LENGTH: 220
<212> TYPE: PRT

<213> ORGANISM: Reticulitermes speratus

<400> SEQUENCE: 44

Met Leu Val Phe Val Phe Ser Leu Leu Ala Ser Val Leu Phe Gly Asp
1               5                   10                  15

Ser Gly Lys Thr Thr Arg Tyr Trp Asp Cys Cys Lys Gly Ser Cys Gly
            20                  25                  30

Trp Glu Ala Lys Ala Asp Val Ser Lys Pro Ile Asp Thr Cys Ala Lys
        35                  40                  45

Asp Gly Thr Thr Arg Val Ala Ser Asn Asp Thr Val Lys Ser Gly Cys
    50                  55                  60

Asp Gly Gly Asp Gly Tyr Met Cys Tyr Asp Gln Thr Pro Trp Gly Val
65                  70                  75                  80

Asn Asp Ser Tyr Ala Leu Gly Phe Ala Ala Ala Ile Ser Gly Gly
                85                  90                  95

Glu Lys Ala Ala Cys Cys Asn Cys Tyr Glu Leu Thr Phe Thr Ser Gly
            100                 105                 110

Pro Val Asn Gly Lys Lys Met Thr Val Gln Val Thr Asn Thr Gly Gly
        115                 120                 125

Asp Leu Gly Ser Asn Gln Phe Asp Leu Ala Ile Pro Gly Gly Gly Val
    130                 135                 140

Gly Ile Tyr Asn Gly Cys Thr Ala Gln Ser Gly Ala Pro Ala Asp Gly
145                 150                 155                 160

Trp Gly Ser Arg Tyr Gly Gly Val Ser Ser Arg Ser Glu Cys Ser Gln
                165                 170                 175

Leu Pro Ser Gly Leu Gln Ala Gly Cys Gln Trp Arg Phe Asp Trp Phe
            180                 185                 190

Gln Asn Ala Asp Asn Pro Ser Met Asn Phe Asn Val Val Ser Cys Pro
        195                 200                 205

Ser Glu Leu Ile Ala Lys Thr Asn Cys Arg Arg Asn
    210                 215                 220

<210> SEQ ID NO 45
<211> LENGTH: 224
<212> TYPE: PRT
<213> ORGANISM: Bursaphelenchus xylophilus

<400> SEQUENCE: 45

Met Lys Ser Leu Val Phe Leu Ala Val Leu Gly Leu Ala Val Ala Gln
1               5                   10                  15

Asp Thr Gly Lys Thr Thr Arg Tyr Trp Asp Cys Cys Lys Pro Ser Cys
            20                  25                  30

Ser Trp Pro Gly Lys Ala Gln Leu Lys Gln Gly Pro Ser Lys Thr Cys
        35                  40                  45

Asp Val Asn Asp Lys Pro Leu Ser Asp Gly Asn Ile Gln Ser Gly Cys
    50                  55                  60

Asn Gly Gly Ser Ala Tyr Ala Cys Ser Thr Asp Gln Pro Trp Ala Val
65                  70                  75                  80

Asp Asp Asn Leu Ser Tyr Gly Phe Ala Ala Val Lys Leu Ala Gly Lys
                85                  90                  95

Gln Glu Ser Asp Trp Cys Cys Ser Cys Tyr Glu Leu Thr Phe Thr Asp
            100                 105                 110

Gly Pro Val Ala Gly Lys Lys Phe Val Val Gln Ala Thr Asn Thr Gly
        115                 120                 125

Gly Asp Leu Gly Ser Asn His Phe Asp Leu Met Ile Pro Gly Gly Gly

```
              130                 135                 140
Val Gly Ile Phe Asn Gly Cys Gln Ala Gln Trp Lys Ser Pro Ala Glu
145                 150                 155                 160

Gly Trp Gly Gln Arg Tyr Gly Val Ser Ser Lys Ala Asp Cys Ala
                165                 170                 175

Thr Leu Pro Thr Ala Leu Gln Pro Gly Cys Asn Trp Arg Phe Asp Trp
                180                 185                 190

Phe Lys Asn Ala Asp Asn Pro Gly Met Thr Phe Lys Arg Val Lys Cys
                195                 200                 205

Pro Ala Glu Ile Thr Ala Lys Ser Gly Cys Ile Arg Ser Asp Asp Ala
                210                 215                 220

<210> SEQ ID NO 46
<211> LENGTH: 355
<212> TYPE: PRT
<213> ORGANISM: Botryotinia fuckeliana

<400> SEQUENCE: 46

Met Gln Val Pro Met Lys Ser Leu Val Ala Leu Leu Pro Phe Phe Leu
1               5                   10                  15

Gln Val Ser Ala Gln Ala Ser Gly Ser Gly Thr Thr Thr Arg Tyr Trp
                20                  25                  30

Asp Cys Cys Lys Pro Ser Cys Ala Trp Ser Gly Lys Ala Thr Leu Glu
            35                  40                  45

Ser Gly Ser Gly Pro Val Gly Thr Cys Asp Ile Asn Asp Ser Pro Leu
        50                  55                  60

Ser Asp Pro Thr Ala Ile Ala Val Ser Gly Cys Asp Gly Gly Asn Ser
65                  70                  75                  80

Tyr Met Cys Ser Asp Gln Ser Pro Trp Ala Val Ser Asp Asp Leu Ala
                85                  90                  95

Tyr Gly Tyr Ala Ala Val Asn Ile Ala Gly Gly Ser Glu Ala Ser Trp
                100                 105                 110

Cys Cys Ala Cys Tyr Glu Leu Thr Phe Thr Ser Thr Ala Leu Ala Gly
            115                 120                 125

Lys Lys Met Ile Val Gln Ala Thr Asn Thr Gly Gly Asp Leu Gly Ser
        130                 135                 140

Asn Gln Phe Asp Leu Ala Ile Pro Gly Gly Gly Val Gly Ile Phe Asn
145                 150                 155                 160

Gly Cys Thr Lys Glu Phe Gly Ala Pro Ser Ser Gly Trp Gly Ala Gln
                165                 170                 175

Tyr Gly Gly Val Ala Ala Val Ser Ser Cys Ala Ala Phe Pro Glu Ala
                180                 185                 190

Leu Lys Pro Gly Cys Ser Phe Arg Phe Asp Trp Phe Glu Gly Ala Asp
                195                 200                 205

Asn Pro Thr Val Asn Phe Lys Gln Val Asn Cys Pro Ala Glu Leu Thr
                210                 215                 220

Lys Ser Thr Gly Cys Lys Arg Ala Asp Asp Ser Met Pro Ala Pro
225                 230                 235                 240

Asp Ala Ser Gly Ser Ala Ser Ala Ser Pro Val Ala Ser Thr Ser Ala
                245                 250                 255

Lys Thr Ser Ser Val Ala Pro Thr Ser Val Ser Ser Ser Val Val
                260                 265                 270

Val Ala Pro Ser Ser Ala Thr Ser Ser Pro Val Val Val Pro Thr
                275                 280                 285
```

Ser Ala Ala Ser Ser Lys Ala Ser Ala Ala Val Val Ser His Pro
    290             295                 300

Val Val Pro Ser Ser Glu Ala Ser Ala Pro Ala Val Thr Ser His
305             310                 315                 320

Ser Ser Ala Thr Lys Ser Ala Lys Thr Ser Val Ala Ala Pro His Ser
                325             330                 335

Thr Ser Ala Ser Thr Gly Tyr Gly Ser Gly Asp Asp Asp Thr Cys
            340             345             350

Asp Ala Glu
        355

<210> SEQ ID NO 47
<211> LENGTH: 251
<212> TYPE: PRT
<213> ORGANISM: Acremonium thermophilum

<400> SEQUENCE: 47

Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Arg Tyr
                20                  25                  30

Trp Asp Cys Cys Lys Pro Ser Cys Ala Trp Pro Leu Lys Gly Asn Ser
            35                  40                  45

Pro Ser Pro Val Gln Thr Cys Asp Lys Asn Asp Arg Pro Leu Asn Asp
    50                  55                  60

Gly Gly Asn Thr Lys Ser Gly Cys Asp Asn Gly Gly Ala Phe Met
65                  70                  75                  80

Cys Ser Ser Gln Ser Pro Trp Ala Val Asn Glu Thr Thr Ser Tyr Gly
                85                  90                  95

Trp Ala Ala Val Arg Ile Ala Gly Ser Thr Glu Ser Ala Trp Cys Cys
                100                 105                 110

Ala Cys Tyr Glu Leu Thr Phe Thr Ser Gly Pro Val Ser Gly Lys Lys
            115                 120                 125

Leu Ile Val Gln Ala Thr Asn Thr Gly Gly Asp Leu Gly Ser Asn His
    130                 135                 140

Phe Asp Leu Ala Ile Pro Gly Gly Gly Val Gly Gln Ser Asn Ala Cys
145                 150                 155                 160

Thr Asn Gln Tyr Gly Ala Pro Pro Asn Gly Trp Gly Asp Arg Tyr Gly
                165                 170                 175

Gly Val His Ser Arg Ser Asp Cys Asp Ser Phe Pro Ala Ala Leu Lys
            180                 185                 190

Ala Gly Cys Tyr Trp Arg Phe Asp Trp Phe Gln Gly Ala Asp Asn Pro
    195                 200                 205

Ser Val Ser Phe Lys Gln Val Ala Cys Pro Ala Ala Ile Thr Ala Lys
210                 215                 220

Ser Gly Cys Thr Arg Gln Asn Asp Ala Ile Asn Glu Thr Pro Thr Gly
225                 230                 235                 240

Pro Ser Thr Val Pro Thr Tyr Thr Ala Ser Gly
                245                 250

<210> SEQ ID NO 48
<211> LENGTH: 229
<212> TYPE: PRT
<213> ORGANISM: Scopulariopsis brevicaulis

<400> SEQUENCE: 48

```
Met His Val Leu Pro Thr Leu Leu Ala Leu Thr Pro Leu Val Leu Pro
1               5                   10                  15

Ala Ala Ser Gln Ala Ser Gly Thr Gly Thr Thr Thr Arg Tyr Trp Asp
            20                  25                  30

Cys Cys Lys Pro Ser Cys Ser Trp Pro Asp Lys Ala Pro Leu Ser Gln
        35                  40                  45

Gly Pro Pro Met Thr Cys Asp Ile Asn Asp Asn Pro Leu Asp Asp Gly
    50                  55                  60

Gly Leu Thr Glu Ser Gly Cys Glu Pro Gly Gly Ala Tyr Met Cys
65                  70                  75                  80

Ser Ser His Ser Pro Trp Ala Val Asp Asp Glu Leu Ala Tyr Gly Trp
                85                  90                  95

Ala Ala Val Asn Ile Gly Gly Gln Thr Glu Ser Asp Trp Cys Cys Ala
            100                 105                 110

Cys Tyr Glu Leu Glu Phe Thr Thr Gly Ala Val Ser Gly Lys Lys Met
        115                 120                 125

Ile Val Gln Ala Thr Asn Thr Gly Gly Asp Leu Gly Asn Asn His Phe
            130                 135                 140

Asp Ile Ala Met Pro Gly Gly Gly Val Gly Ile Phe Asn Gly Cys Thr
145                 150                 155                 160

Asp Gln Trp Gly Ser Pro Pro Asn Gly Trp Gly Asp Arg Tyr Gly Gly
                165                 170                 175

Val His Thr Arg Ala Asp Cys Asp Ser Phe Pro Glu Ala Leu Lys Ala
            180                 185                 190

Gly Cys Glu Trp Arg Phe Asp Trp Phe Gly Gly Thr Asp Asn Pro Asp
        195                 200                 205

Val Ser Phe Arg Glu Val Glu Cys Pro Ala Glu Leu Val Gln Lys Ser
210                 215                 220

Gln Cys Gln Arg Ser
225

<210> SEQ ID NO 49
<211> LENGTH: 340
<212> TYPE: PRT
<213> ORGANISM: Syncephalastrum racemosum

<400> SEQUENCE: 49

Met Ile Leu His Arg Thr Glu Lys Asn Asn Asp Met Arg Leu Ser Phe
1               5                   10                  15

Ala Ala Ser Leu Leu Leu Ala Thr Val Gly Met Gln Leu Val Ser Ala
            20                  25                  30

Ala Asp Cys Ser Asn Lys Ala Tyr Ser Gln Cys Gly Gly Gln Asn Trp
        35                  40                  45

Ser Gly Glu Ser Cys Cys Val Ser Gly Tyr Glu Cys Lys Gln Leu Asn
    50                  55                  60

Asp Tyr Tyr His Gln Cys Val Pro Gln Asn Ser Gly Ser Phe Ser Gly
65                  70                  75                  80

Ser Ser Ser Ala Ala Ala Pro Ser His Met Ala Thr Ser Ser Ala Pro
                85                  90                  95

Ser Ser Ser Lys Ala Pro Ser Ser Pro Ala Ser Ser Lys Thr Pro
            100                 105                 110

Ser Ser Pro Ala Ala Ser Ser Ser Ser Ser Gly Ser Gly Tyr Lys
        115                 120                 125

Pro Ile Ser Gly Gly Ala Ser Gly Asp Gly Thr Thr Thr Arg Tyr Trp
    130                 135                 140
```

```
Asp Cys Cys Lys Ala Ser Cys Ser Trp Pro Gly Lys Ala Pro Val Thr
145                 150                 155                 160

Asn Pro Val Gly Thr Cys Ala Lys Asp Gly Val Lys Leu Val Asp Ala
                165                 170                 175

Asn Val Gln Ser Gly Cys Asn Gly Gly Glu Gly Tyr Met Cys Asn Asp
            180                 185                 190

Asn Gln Pro Trp Ala Ile Asp Asp Asn Leu Ser Tyr Gly Phe Ala Ala
        195                 200                 205

Ala Ser Ile Ser Gly Lys Ser Glu Ser Asp Phe Cys Cys Ser Cys Tyr
    210                 215                 220

Glu Leu Thr Phe Ser Ser Gly Glu Ile Glu Gly Lys Lys Met Val Val
225                 230                 235                 240

Gln Val Thr Asn Thr Gly Gly Asp Leu Ser Asn Asn His Phe Asp Leu
                245                 250                 255

Gln Ile Pro Gly Gly Gly Val Gly Ile Phe Asn Gly Cys Gln Thr Gln
            260                 265                 270

Trp Asp Ala Pro Ser Asp Gly Trp Gly Gln Arg Tyr Gly Gly Ile Ser
        275                 280                 285

Ser Ala Ser Glu Cys Ser Gln Leu Pro Lys Gln Leu Gln Asp Gly Cys
    290                 295                 300

Lys Trp Arg Phe Asp Trp Phe Lys Asn Ala Asp Asn Pro Asn Val Ser
305                 310                 315                 320

Phe Lys Gln Val Ser Cys Pro Ala Glu Leu Val Lys Lys Thr Gly Cys
                325                 330                 335

Glu Arg Thr Ser
            340

<210> SEQ ID NO 50
<211> LENGTH: 338
<212> TYPE: PRT
<213> ORGANISM: Rhizopus oryzae

<400> SEQUENCE: 50

Met Lys Phe Ile Thr Ile Ala Ser Ser Ala Leu Leu Ala Leu Ala Leu
1               5                   10                  15

Gly Thr Glu Met Ala Ser Ala Ala Glu Cys Ser Lys Leu Tyr Gly Gln
            20                  25                  30

Cys Gly Gly Lys Asn Trp Asn Gly Pro Thr Cys Cys Glu Ser Gly Ser
        35                  40                  45

Thr Cys Lys Val Ser Asn Asp Tyr Tyr Ser Gln Cys Leu Pro Ser Gly
    50                  55                  60

Ser Ser Gly Asn Lys Ser Ser Glu Ser Ala His Lys Lys Thr Thr Thr
65                  70                  75                  80

Ala Ala His Lys Lys Thr Thr Thr Ala Ala His Lys Lys Thr Thr Thr
                85                  90                  95

Ala Pro Ala Lys Lys Thr Thr Thr Val Ala Lys Ala Ser Thr Pro Ser
            100                 105                 110

Asn Ser Ser Ser Ser Ser Gly Lys Tyr Ser Ala Val Ser Gly Gly
        115                 120                 125

Ala Ser Gly Asn Gly Val Thr Thr Arg Tyr Trp Asp Cys Cys Lys Ala
    130                 135                 140

Ser Cys Ser Trp Pro Gly Lys Ala Asn Val Ser Ser Pro Val Lys Ser
145                 150                 155                 160

Cys Asn Lys Asp Gly Val Thr Ala Leu Ser Asp Ser Asn Ala Gln Ser
```

```
            165                 170                 175
Gly Cys Asn Gly Gly Asn Ser Tyr Met Cys Asn Asp Asn Gln Pro Trp
        180                 185                 190

Ala Val Asn Asp Asn Leu Ala Tyr Gly Phe Ala Ala Ala Ile Ser
            195                 200                 205

Gly Gly Gly Glu Ser Arg Trp Cys Cys Ser Cys Phe Glu Leu Thr Phe
    210                 215                 220

Thr Ser Thr Ser Val Ala Gly Lys Lys Met Val Gln Val Thr Asn
225                 230                 235                 240

Thr Gly Gly Asp Leu Gly Ser Ser Thr Gly Ala His Phe Asp Leu Gln
            245                 250                 255

Met Pro Gly Gly Gly Val Gly Ile Phe Asn Gly Cys Ser Ser Gln Trp
        260                 265                 270

Gly Ala Pro Asn Asp Gly Trp Gly Ser Arg Tyr Gly Gly Ile Ser Ser
            275                 280                 285

Ala Ser Asp Cys Ser Ser Leu Pro Ser Ala Leu Gln Ala Gly Cys Lys
    290                 295                 300

Trp Arg Phe Asn Trp Phe Lys Asn Ala Asp Asn Pro Ser Met Thr Tyr
305                 310                 315                 320

Lys Glu Val Thr Cys Pro Lys Glu Ile Thr Ala Lys Thr Gly Cys Ser
            325                 330                 335

Arg Lys

<210> SEQ ID NO 51
<211> LENGTH: 226
<212> TYPE: PRT
<213> ORGANISM: Crinipellis scabella

<400> SEQUENCE: 51

Met Val His Pro Asn Met Leu Lys Thr Leu Ala Pro Leu Ile Ile Leu
1               5                   10                  15

Ala Ala Ser Val Thr Ala Gln Thr Ala Gly Val Thr Thr Arg Tyr Trp
            20                  25                  30

Asp Cys Cys Lys Pro Ser Cys Gly Trp Ser Gly Lys Ala Ser Val Ser
        35                  40                  45

Ala Pro Val Arg Thr Cys Asp Arg Asn Gly Asn Thr Leu Gly Pro Asp
    50                  55                  60

Val Lys Ser Gly Cys Asp Ser Gly Gly Thr Ser Phe Thr Cys Ala Asn
65                  70                  75                  80

Asn Gly Pro Phe Ala Ile Asp Asn Asn Thr Ala Tyr Gly Phe Ala Ala
            85                  90                  95

Ala His Leu Ala Gly Ser Ser Glu Ala Ala Trp Cys Cys Gln Cys Tyr
        100                 105                 110

Glu Leu Thr Phe Thr Ser Gly Pro Val Val Gly Lys Lys Leu Thr Val
    115                 120                 125

Gln Val Thr Asn Thr Gly Gly Asp Leu Gly Asn Asn His Phe Asp Leu
            130                 135                 140

Met Ile Pro Gly Gly Gly Val Gly Leu Phe Thr Gln Gly Cys Pro Ala
145                 150                 155                 160

Gln Phe Gly Ser Trp Asn Gly Gly Ala Gln Tyr Gly Gly Val Ser Ser
            165                 170                 175

Arg Asp Gln Cys Ser Gln Leu Pro Ala Ala Val Gln Ala Gly Cys Gln
        180                 185                 190

Phe Arg Phe Asp Trp Met Gly Gly Ala Asp Asn Pro Asn Val Thr Phe
```

```
                195                 200                 205
Arg Pro Val Thr Cys Pro Ala Gln Leu Thr Asn Ile Ser Gly Cys Val
        210                 215                 220

Arg Lys
225

<210> SEQ ID NO 52
<211> LENGTH: 222
<212> TYPE: PRT
<213> ORGANISM: Macrophomina phaseolina

<400> SEQUENCE: 52

Met Phe Ser Pro Leu Trp Ala Leu Ser Ala Leu Leu Leu Phe Pro Ala
1               5                   10                  15

Thr Glu Ala Thr Ser Gly Val Thr Thr Arg Tyr Trp Asp Cys Cys Lys
            20                  25                  30

Pro Ser Cys Ala Trp Thr Gly Lys Ala Ser Val Ser Lys Pro Val Gly
        35                  40                  45

Thr Cys Asp Ile Asn Asp Asn Ala Gln Thr Pro Ser Asp Leu Leu Lys
    50                  55                  60

Ser Ser Cys Asp Gly Gly Ser Ala Tyr Tyr Cys Ser Asn Gln Gly Pro
65                  70                  75                  80

Trp Ala Val Asn Asp Ser Leu Ser Tyr Gly Phe Ala Ala Ala Lys Leu
                85                  90                  95

Ser Gly Lys Gln Glu Thr Asp Trp Cys Cys Gly Cys Tyr Lys Leu Thr
            100                 105                 110

Phe Thr Ser Thr Ala Val Ser Gly Lys Gln Met Ile Val Gln Ile Thr
        115                 120                 125

Asn Thr Gly Gly Asp Leu Gly Asn Asn His Phe Asp Ile Ala Met Pro
    130                 135                 140

Gly Gly Gly Val Gly Ile Phe Asn Gly Cys Ser Lys Gln Trp Asn Gly
145                 150                 155                 160

Ile Asn Leu Gly Asn Gln Tyr Gly Gly Phe Thr Asp Arg Ser Gln Cys
                165                 170                 175

Ala Thr Leu Pro Ser Lys Trp Gln Ala Ser Cys Asn Trp Arg Phe Asp
            180                 185                 190

Trp Phe Glu Asn Ala Asp Asn Pro Thr Val Asp Trp Glu Pro Val Thr
        195                 200                 205

Cys Pro Gln Glu Leu Val Ala Arg Thr Gly Cys Ser Arg Thr
    210                 215                 220

<210> SEQ ID NO 53
<211> LENGTH: 245
<212> TYPE: PRT
<213> ORGANISM: Podospora anserina

<400> SEQUENCE: 53

Met Gln Leu Ala Leu Thr Ile Leu Ala Phe Gly Gly Phe Ala Ser Ala
1               5                   10                  15

Gln Gly Ala Gln Gly Ala Gly Lys Thr Thr Arg Tyr Trp Asp Cys Cys
            20                  25                  30

Lys Pro Ser Cys Ala Trp Pro Gly Lys Ser Thr Ala Ser Thr Pro Val
        35                  40                  45

Leu Thr Cys Asp Arg Asn Asp Asn Pro Leu Asn Asp Arg Gly Ser Thr
    50                  55                  60

Arg Ser Gly Cys Asp Ser Gly Gly Ser Ala Phe Met Cys Ser Asn Gln
```

```
              65                  70                  75                  80
Ser Pro Trp Ala Val Asn Glu Thr Val Ala Tyr Gly Trp Ala Ala Val
                    85                  90                  95

Asn Ile Ala Gly Ser Asn Glu Ala Ser Trp Cys Cys Ser Cys Tyr Glu
                100                 105                 110

Leu Thr Phe Thr Ser Gly Pro Val Ser Gly Lys Lys Met Ile Val Gln
                115                 120                 125

Ala Thr Asn Thr Gly Gly Asp Leu Gly Asn Asn His Phe Asp Ile Ala
            130                 135                 140

Met Pro Gly Gly Gly Val Gly Ile Phe Asn Ala Cys Thr Gln Gln Tyr
145                 150                 155                 160

Gly Ala Pro Pro Asn Gly Trp Gly Glu Arg Tyr Gly Gly Val Gly Ser
                165                 170                 175

Lys Ser Ala Cys Glu Ser Phe Pro Asp Lys Leu Lys Ala Gly Cys Asn
                180                 185                 190

Trp Arg Phe Asp Trp Phe Met Gly Ala Asp Asn Pro Asp Val Arg Phe
                195                 200                 205

Arg Gln Val Ala Cys Pro Ala Ala Ile Thr Ala Lys Ser Gln Cys Val
            210                 215                 220

Arg Gln Arg Asp Val Ile Asp Gln Thr Pro Thr Gly Pro Ser Thr Val
225                 230                 235                 240

Pro Thr Trp Thr Pro
                245

<210> SEQ ID NO 54
<211> LENGTH: 366
<212> TYPE: PRT
<213> ORGANISM: Rhizopus oryzae

<400> SEQUENCE: 54

Met Lys Phe Ile Thr Ile Thr Ser Ser Ala Leu Leu Ala Leu Ala Leu
1               5                   10                  15

Gly Thr Glu Met Ala Ser Ala Ala Lys Cys Ser Lys Leu Tyr Gly Gln
                20                  25                  30

Cys Gly Gly Lys Asp Trp Asn Gly Pro Thr Cys Cys Glu Ser Gly Ser
            35                  40                  45

Thr Cys Lys Val Ser Asn Asp Tyr Tyr Ser Gln Cys Leu Ala Pro Glu
        50                  55                  60

Ser Asn Gly Asn Lys Ser Ser Glu Cys Ser Lys Leu Tyr Gly Gln Cys
65                  70                  75                  80

Gly Gly Lys Asp Trp Asn Gly Pro Thr Cys Cys Glu Ser Gly Ser Thr
                85                  90                  95

Cys Lys Val Ser Asn Asp Tyr Tyr Ser Gln Cys Leu Ala Pro Glu Ser
                100                 105                 110

Asn Gly Asn Lys Thr Ser Glu Ser Ala His Lys Thr Thr Thr Thr Thr
                115                 120                 125

Ala Pro Ala Lys Glu Ile Thr Thr Ala Lys Ala Ser Asn Ser Ser
            130                 135                 140

Asn Ser Ser Gly Lys Tyr Ser Ile Val Ser Gly Ala Ser Gly Asn
145                 150                 155                 160

Gly Val Thr Thr Arg Tyr Trp Asp Cys Cys Lys Ala Ser Cys Ser Trp
                165                 170                 175

Pro Gly Lys Ala Asn Val Ser Ser Pro Val Lys Ser Cys Asn Lys Asp
                180                 185                 190
```

```
Gly Val Thr Ala Leu Ser Asp Ser Asn Val Gln Ser Gly Cys Asn Gly
        195                 200                 205

Gly Asn Ser Tyr Met Cys Asn Asp Asn Gln Pro Trp Ala Val Asn Asp
    210                 215                 220

Asn Leu Ala Tyr Gly Phe Ala Ala Ala Ala Ile Ser Gly Gly Gly Glu
225                 230                 235                 240

Ser Arg Trp Cys Cys Ser Cys Phe Glu Leu Thr Phe Thr Ser Thr Ser
                245                 250                 255

Val Ala Gly Lys Lys Met Val Ile Gln Val Thr Asn Thr Gly Gly Asp
            260                 265                 270

Leu Gly Ser Ser Thr Gly Ala His Phe Asp Leu Gln Met Pro Gly Gly
        275                 280                 285

Gly Val Gly Ile Phe Asn Gly Cys Ser Lys Gln Trp Gly Ala Pro Asn
    290                 295                 300

Asp Gly Trp Gly Ser Arg Tyr Gly Gly Ile Ser Ser Ala Ser Asp Cys
305                 310                 315                 320

Ser Ser Leu Pro Ser Ala Leu Gln Ala Gly Cys Lys Trp Arg Phe Asn
                325                 330                 335

Trp Phe Lys Asn Ala Asp Asn Pro Ser Met Thr Tyr Lys Glu Val Thr
            340                 345                 350

Cys Pro Lys Glu Ile Thr Ala Lys Thr Gly Cys Ser Arg Lys
        355                 360                 365

<210> SEQ ID NO 55
<211> LENGTH: 286
<212> TYPE: PRT
<213> ORGANISM: Bursaphelenchus xylophilus

<400> SEQUENCE: 55

Met Ala Lys Leu Phe Val Ser Val Leu Val Val Ala Leu Leu Leu Glu
1               5                   10                  15

Val Val Val Glu Cys Lys Ser Ser Lys Thr Lys Lys Thr Lys Ala Thr
            20                  25                  30

Thr Val Lys Ser Thr Lys Ala Thr Ala Ala Pro Thr Lys Ala Thr Ala
        35                  40                  45

Ala Pro Thr Lys Ala Thr Thr Ala Ala Ser Ser Ser Ala Gly Gly Asn
    50                  55                  60

Ser Ala Asp Tyr Ser Tyr Ser Tyr Val Ser Gly Gly Thr Ser Gly Thr
65                  70                  75                  80

Gly Val Thr Thr Arg Tyr Trp Asp Cys Cys Lys Ser Ser Cys Ala Trp
                85                  90                  95

Pro Gly Lys Ala Ser Leu Lys Ser Gly Pro Ile Gln Thr Cys Asp Val
            100                 105                 110

His Asp Gln Pro Leu Asn Asp Gly Gly Asn Thr Gln Ser Gly Cys Asn
        115                 120                 125

Gly Gly Ser Ala Tyr Ser Cys Ser Thr Glu Gln Pro Tyr Ala Val Asn
    130                 135                 140

Asp Thr Leu Ser Phe Gly Phe Ala Ala Val Lys Leu Ala Gly Gly Ser
145                 150                 155                 160

Glu Ser Ser Trp Cys Cys Ala Cys Tyr Glu Leu Thr Phe Thr Ser Gly
                165                 170                 175

Ser Val Asn Gly Lys Lys Phe Val Ile Gln Ala Thr Asn Thr Gly Gly
            180                 185                 190

Asp Leu Gly Asp Asn His Phe Asp Leu Ala Ile Pro Gly Gly Gly Val
        195                 200                 205
```

```
Gly Ile Phe Asn Gly Cys Thr Ala Gln Trp Gly Ala Pro Ser Ser Gly
    210                 215                 220

Trp Gly Ala Gln Tyr Gly Gly Val Ser Ser Arg Ser Asp Cys Ser Gln
225                 230                 235                 240

Leu Pro Ala Lys Leu Gln Pro Gly Cys Asp Trp Arg Phe Asp Trp Phe
                245                 250                 255

Gly Asn Ser Asp Asn Pro Gly Val Thr Phe Lys Gln Val Thr Cys Pro
            260                 265                 270

Lys Thr Leu Thr Asp Lys Ser Lys Cys Ile Arg Ala Asp Asp
        275                 280                 285

<210> SEQ ID NO 56
<211> LENGTH: 359
<212> TYPE: PRT
<213> ORGANISM: Bursaphelenchus xylophilus

<400> SEQUENCE: 56

Met Asn Lys Leu Leu Val Ser Val Leu Val Leu Ala Leu Leu Phe Glu
1               5                   10                  15

Asn Val Val Glu Gly Lys Thr Cys Gly Pro Leu Thr Thr Ala Ala Gly
            20                  25                  30

Ala Thr Gln Thr Ala Pro Pro Ala Ser Ala Ala Ser Thr Thr Lys Gly
        35                  40                  45

Gln Thr Ala Ala Ser Gly Ser Pro Ala Thr Thr Ala Ser Ala Ala Pro
    50                  55                  60

Thr Lys Ala Ser Ala Ala Pro Ser Thr Ala Ser Ala Ala Pro Ser Lys
65                  70                  75                  80

Ala Ser Ala Ala Pro Ser Thr Ala Ser Ala Ala Pro Ser Thr Ala Ser
                85                  90                  95

Ala Ala Pro Ser Lys Ala Ser Ala Ala Pro Ser Thr Ala Ser Ser Thr
            100                 105                 110

Ala Ser Ser Thr Thr Pro Thr Thr Thr Thr Lys Ala Ser Ser Thr Ala
        115                 120                 125

Ala Ala Thr Thr Gln Ala Ser Gly Asn Ser Ala Asp Tyr Ser Tyr Ser
    130                 135                 140

Tyr Ile Ser Gly Gly Thr Ser Gly Thr Gly Val Thr Thr Arg Tyr Trp
145                 150                 155                 160

Asp Cys Cys Lys Ser Ser Cys Ala Trp Pro Gly Lys Ala Thr Leu Lys
                165                 170                 175

Ser Gly Pro Ile Gln Thr Cys Asp Val His Asp Gln Pro Leu Asn Asp
            180                 185                 190

Gly Gly Asn Thr Gln Ser Gly Cys Asn Gly Gly Ser Ala Tyr Ser Cys
        195                 200                 205

Ser Thr Glu Gln Pro Tyr Ala Val Asn Asp Thr Leu Ser Phe Gly Phe
    210                 215                 220

Ala Ala Val Lys Leu Ala Gly Gly Ser Glu Ser Thr Trp Cys Cys Ala
225                 230                 235                 240

Cys Tyr Glu Leu Thr Phe Thr Ser Gly Ser Val Ala Gly Lys Lys Phe
                245                 250                 255

Val Ile Gln Ala Thr Asn Thr Gly Gly Asp Leu Gly Asp Asn His Phe
            260                 265                 270

Asp Leu Ala Ile Pro Gly Gly Gly Val Gly Ile Phe Asn Gly Cys Thr
        275                 280                 285

Ala Gln Trp Gly Ala Pro Ser Ser Gly Trp Gly Ser Gln Tyr Gly Gly
```

```
                290                 295                 300
Val Ser Ser Arg Ser Asp Cys Ser Gln Leu Pro Ala Thr Leu Gln Pro
305                 310                 315                 320

Gly Cys Asp Trp Arg Phe Asp Trp Phe Gly Asn Ser Asp Asn Pro Gly
                325                 330                 335

Val Thr Phe Lys Gln Val Thr Cys Pro Lys Thr Ile Thr Asp Lys Ser
                340                 345                 350

Lys Cys Ile Arg Ala Asp Asp
        355

<210> SEQ ID NO 57
<211> LENGTH: 227
<212> TYPE: PRT
<213> ORGANISM: Humicolagrisea var. thermoidea

<400> SEQUENCE: 57

Met Gln Leu Pro Leu Thr Thr Leu Leu Thr Leu Leu Pro Ala Leu Ala
1               5                   10                  15

Ala Ala Gln Ser Gly Ser Gly Arg Thr Thr Arg Tyr Trp Asp Cys Cys
                20                  25                  30

Lys Pro Ser Cys Ala Trp Pro Gly Lys Gly Pro Ala Pro Val Arg Thr
            35                  40                  45

Cys Asp Arg Trp Asp Asn Pro Leu Phe Asp Gly Gly Asn Thr Arg Ser
        50                  55                  60

Gly Cys Asp Ala Gly Gly Ala Tyr Met Cys Ser Asp Gln Ser Pro
65                  70                  75                  80

Trp Ala Val Ser Asp Asp Leu Ala Tyr Gly Trp Ala Ala Val Asn Ile
                85                  90                  95

Ala Gly Ser Asn Glu Arg Gln Trp Cys Cys Ala Cys Tyr Glu Leu Thr
            100                 105                 110

Phe Thr Ser Gly Pro Val Ala Gly Lys Arg Met Ile Val Gln Ala Ser
        115                 120                 125

Asn Thr Gly Gly Asp Leu Gly Asn Asn His Phe Asp Ile Ala Met Pro
    130                 135                 140

Gly Gly Gly Val Gly Ile Phe Asn Ala Cys Thr Asp Gln Tyr Gly Ala
145                 150                 155                 160

Pro Pro Asn Gly Trp Gly Gln Arg Tyr Gly Gly Ile Ser Gln Arg His
                165                 170                 175

Glu Cys Asp Ala Phe Pro Glu Lys Leu Lys Pro Gly Cys Tyr Trp Arg
            180                 185                 190

Phe Asp Trp Cys Val Ser Leu Phe Pro Pro Leu Ser Leu Ser Leu Pro
        195                 200                 205

Pro Gly Thr Gly Gln Thr Met Gly Arg Ser Cys Val Phe Phe Pro Leu
    210                 215                 220

Ser Ala Asn
225

<210> SEQ ID NO 58
<211> LENGTH: 346
<212> TYPE: PRT
<213> ORGANISM: Phycomyces nitens

<400> SEQUENCE: 58

Met Lys Phe Ser Ile Ile Ala Ser Ala Leu Leu Leu Ala Ala Ser Ser
1               5                   10                  15

Thr Tyr Ala Ala Glu Cys Ser Gln Gly Tyr Gly Gln Cys Gly Gly Lys
```

```
            20                  25                  30
Met Trp Thr Gly Pro Thr Cys Cys Thr Ser Gly Phe Thr Cys Val Gly
            35                  40                  45

Ala Glu Asn Asn Glu Trp Tyr Ser Gln Cys Ile Pro Asn Asp Gln Val
 50                  55                  60

Gln Gly Asn Pro Lys Thr Thr Thr Thr Thr Lys Ala Ala Thr
 65                  70                  75                  80

Thr Thr Lys Ala Pro Val Thr Thr Lys Ala Thr Thr Thr Thr
                     85                  90                  95

Thr Lys Ala Pro Val Thr Thr Thr Lys Ala Thr Thr Thr Thr
                    100                 105                 110

Lys Thr Thr Thr Lys Thr Thr Thr Lys Ala Ala Thr Thr Thr Ser
                115                     120                 125

Ser Ser Asn Thr Gly Tyr Ser Pro Ile Ser Gly Gly Phe Ser Gly Asn
            130                     135                 140

Gly Arg Thr Thr Arg Tyr Trp Asp Cys Cys Lys Pro Ser Cys Ala Trp
145                 150                 155                 160

Asp Gly Lys Ala Ser Val Thr Lys Pro Val Leu Thr Cys Ala Lys Asp
                    165                 170                 175

Gly Val Ser Arg Leu Gly Ser Asp Val Gln Ser Gly Cys Val Gly Gly
                180                     185                 190

Gln Ala Tyr Met Cys Asn Asp Asn Gln Pro Trp Val Val Asn Asp Asp
                195                     200                 205

Leu Ala Tyr Gly Phe Ala Ala Ala Ser Leu Gly Ser Ala Gly Ala Ser
            210                     215                 220

Ala Phe Cys Cys Gly Cys Tyr Glu Leu Thr Phe Thr Asn Thr Ala Val
225                     230                 235                 240

Ala Gly Lys Lys Phe Val Val Gln Val Thr Asn Thr Gly Asp Asp Leu
                    245                 250                 255

Ser Thr Asn His Phe Asp Leu Gln Met Pro Gly Gly Gly Val Gly Tyr
                260                     265                 270

Phe Asn Gly Cys Gln Ser Gln Trp Asn Thr Asn Thr Asp Gly Trp Gly
            275                     280                 285

Ala Arg Tyr Gly Gly Ile Ser Ser Ile Ser Glu Cys Asp Lys Leu Pro
            290                     295                 300

Thr Gln Leu Gln Ala Gly Cys Lys Trp Arg Phe Gly Trp Phe Lys Asn
305                     310                 315                 320

Ala Asp Asn Pro Glu Val Thr Phe Lys Ala Val Thr Cys Pro Ala Glu
                    325                 330                 335

Ile Ile Ala Lys Thr Gly Cys Glu Arg Lys
                340                 345

<210> SEQ ID NO 59
<211> LENGTH: 360
<212> TYPE: PRT
<213> ORGANISM: Rhizopus oryzae

<400> SEQUENCE: 59

Met Lys Phe Leu Thr Ile Ala Ser Ser Ala Ile Leu Ala Leu Ala Val
 1               5                  10                  15

Gly Thr Glu Met Ala His Ala Ala Glu Cys Ser Lys Ala Tyr Tyr Gln
                20                  25                  30

Cys Gly Gly Lys Asn Trp Asp Gly Pro Thr Cys Cys Glu Ser Gly Ser
            35                  40                  45
```

Thr Cys Val Asp Tyr Pro Asp Asn Pro Phe Tyr Ser Gln Cys Val Pro
    50                  55                  60

Asn Glu Asn Leu Thr Ser Thr Asn Lys Ser Ser His Lys Thr Thr Thr
65                  70                  75                  80

Thr Glu Ser Ala Lys Lys Thr Thr Thr Lys Gly Ser Lys Lys Thr
                85                  90                  95

Thr Thr Thr Glu Ala Ser Lys Lys Thr Thr Thr Glu Ala Ser Lys
            100                 105                 110

Lys Thr Thr Thr Glu Ala Ser Lys Lys Thr Thr Thr Thr Lys
            115                 120                 125

Lys Ala Ser Thr Ser Thr Ser Ser Ser Ser Ser Ala Ser Thr Asn
130                 135                 140

Tyr Ser Ala Val Ser Gly Gly Ala Ser Gly Asn Gly Glu Thr Thr Arg
145                 150                 155                 160

Tyr Trp Asp Cys Cys Lys Pro Ser Cys Ser Trp Pro Gly Lys Ala Asp
                165                 170                 175

Val Thr Ser Pro Val Gly Ser Cys Asn Lys Asp Gly Lys Thr Leu Ala
            180                 185                 190

Asp Asn Asn Thr Gln Asn Gly Cys Val Gly Gly Ser Ser Tyr Thr Cys
            195                 200                 205

Asn Asp Asn Gln Pro Trp Val Val Ser Asp Leu Ala Tyr Gly Phe
210                 215                 220

Ala Ala Ala Ser Ile Ser Gly Gly Ser Glu Ala Thr Trp Cys Cys Ala
225                 230                 235                 240

Cys Phe Glu Leu Thr Phe Thr Ser Thr Ala Val Lys Gly Lys Lys Met
                245                 250                 255

Val Val Gln Val Thr Asn Thr Gly Ser Asp Leu Gly Ser Asn Thr Gly
            260                 265                 270

Ala His Phe Asp Leu Gln Met Pro Gly Gly Gly Val Gly Ile Tyr Asn
        275                 280                 285

Gly Cys Ala Thr Gln Trp Gly Ala Pro Thr Asp Gly Trp Gly Ala Arg
        290                 295                 300

Tyr Gly Gly Val Ser Ser Ala Ser Asp Cys Ser Asn Leu Pro Ser Ala
305                 310                 315                 320

Leu Gln Ala Gly Cys Lys Trp Arg Phe Gly Trp Phe Lys Asn Ala Asp
                325                 330                 335

Asn Pro Thr Met Thr Tyr Lys Gln Val Thr Cys Pro Lys Ala Ile Thr
            340                 345                 350

Ala Lys Ser Gly Cys Ser Arg Lys
            355                 360

<210> SEQ ID NO 60
<211> LENGTH: 219
<212> TYPE: PRT
<213> ORGANISM: Mastotermes darwiniensis hindgut symbiont sp

<400> SEQUENCE: 60

Met Phe Val Ala Phe Val Ile Gly Ala Leu Cys Lys Asp Phe Ser Gly
1               5                   10                  15

Asn Gly Gln Thr Thr Arg Tyr Trp Asp Cys Cys Lys Pro Ser Cys Ser
                20                  25                  30

Trp Ser Lys Lys Ala Gln Val Ser His Val Val Asn Ser Cys Asn Ala
            35                  40                  45

Asn Asn Gln His Asp Ser Thr Val Asp Leu Lys Ser Gly Cys Asp Gly
50                  55                  60

-continued

```
Gly Pro Ser Tyr Ala Cys Ala Asp Gln Ala Pro Trp Ala Val Asn Ser
 65                  70                  75                  80

Ser Tyr Phe Met Gly Thr Ala Ala Ala Leu Ser Gly Ala Ser Glu
             85                  90                  95

Ala Asp Leu Cys Cys Lys Cys Phe Glu Leu Thr Phe Thr Ser Gly Thr
            100                 105                 110

Pro Asn Gly Lys Lys Met Leu Val Gln Ile Thr Asn Thr Gly Ser Asp
            115                 120                 125

Leu Ser Gly Asn Gln Phe Asp Leu Leu Ile Pro Gly Gly Val Gly
        130                 135                 140

Ile Phe Asp Gly Cys Thr Arg Gln Tyr Pro Ser Tyr Asp Trp Gly
145                 150                 155                 160

Gln Arg Tyr Gly Gly Val Thr Ser Arg Asp Gly Cys Ser Lys Leu Pro
                165                 170                 175

Ser Thr Leu Gln Thr Gly Cys Gln Phe Arg Phe Asp Tyr Ile Gly Asp
            180                 185                 190

Asn Pro Ser Val Ser Phe Lys Ser Thr His Cys Pro Asp Ser Ile Val
            195                 200                 205

Gly Lys Thr Asn Ser Arg Arg Asn Asp Asp Ala
        210                 215

<210> SEQ ID NO 61
<211> LENGTH: 218
<212> TYPE: PRT
<213> ORGANISM: Magnaporthe grisea

<400> SEQUENCE: 61

Met Lys Ile Thr Thr Ser Ala Val Leu Ala Cys Leu Thr Ala Ala Val
 1               5                  10                  15

Ser Ala Gln Val Gln Gly Thr Gly Ala Thr Thr Arg Tyr Trp Asp Cys
            20                  25                  30

Cys Lys Pro Ser Cys Gly Trp Pro Gly Lys Ala Asn Leu Ala Ser Gly
         35                  40                  45

Pro Leu Arg Thr Cys Asp Lys Ala Asp Asn Pro Leu Asn Asp Gly Gly
 50                  55                  60

Asn Thr Lys Ser Gly Cys Asp Asn Gly Gly Ala Phe Met Cys Ser
 65                  70                  75                  80

Ser Gln Glu Pro Leu Ala Val Asp Asp Ser Leu Ala Tyr Gly Phe Ala
             85                  90                  95

Ala Val Arg Ile Ser Gly Gln Arg Glu Ser Asp Trp Cys Cys Ala Cys
            100                 105                 110

Tyr Glu Leu Thr Phe Thr Asn Leu Leu Arg Asn Thr Gly Gly Asp Leu
            115                 120                 125

Gly Gln Asn His Phe Asp Ile Ala Met Pro Gly Gly Val Gly Ile
        130                 135                 140

Phe Asn Ala Cys Thr Glu Gln Tyr Gly Ala Pro Ala Asn Gly Trp Gly
145                 150                 155                 160

Glu Arg Tyr Gly Gly Val Arg Ser Arg Ser Glu Cys Asp Ala Phe Pro
                165                 170                 175

Glu Lys Leu Lys Lys Gly Cys Tyr Trp Arg Phe Asp Trp Phe Lys Gly
            180                 185                 190

Ala Asp Asn Pro Ser Val Ser Phe Lys Gln Val Thr Cys Pro Ser Glu
            195                 200                 205

Leu Thr Ser Lys Ser Gly Cys Val Arg Ala
```

<210> SEQ ID NO 62
<211> LENGTH: 219
<212> TYPE: PRT
<213> ORGANISM: Mastotermes darwiniensis hindgut symbiont sp.

<400> SEQUENCE: 62

Met Phe Val Ala Phe Val Ile Gly Ala Leu Cys Lys Asp Tyr Ser Gly
1               5                   10                  15

Asn Gly Gln Thr Thr Arg Tyr Trp Asp Cys Cys Lys Pro Ser Cys Ser
            20                  25                  30

Trp Ser Lys Lys Ala Gln Val Ser His Val Val Asn Ser Cys Asn Ala
        35                  40                  45

Asn Gly Gln His Asp Ser Thr Val Asp Leu Lys Ser Gly Cys Asp Gly
    50                  55                  60

Gly Pro Ser Tyr Ala Cys Thr Asp Gln Ala Pro Trp Ala Val Asn Ser
65                  70                  75                  80

Ser Tyr Phe Met Gly Thr Ala Ala Ala Leu Ser Gly Gly Ser Glu
                85                  90                  95

Ser Asp Leu Cys Cys Lys Cys Phe Glu Leu Thr Phe Thr Ser Gly Thr
                100                 105                 110

Pro Asn Gly Lys Lys Met Leu Val Gln Ile Thr Asn Thr Gly Ser Asp
            115                 120                 125

Leu Ser Gly Asn Gln Phe Asp Leu Leu Ile Pro Gly Gly Val Gly
    130                 135                 140

Ile Phe Asp Gly Cys Thr Arg Gln Tyr Pro Gly Ser Tyr Asp Trp Gly
145                 150                 155                 160

Gln Arg Tyr Gly Gly Val Thr Ser Arg Asp Gly Cys Ser Lys Leu Pro
                165                 170                 175

Ser Ala Leu Gln Ser Gly Phe Gln Phe Arg Phe Asp Tyr Ile Ala Asp
            180                 185                 190

Asn Pro Ser Val Ser Phe Lys Ser Thr His Cys Pro Asp Thr Ile Val
        195                 200                 205

Ser Lys Pro Thr Cys Arg Arg Asn Asp Asp Ser
    210                 215

<210> SEQ ID NO 63
<211> LENGTH: 220
<212> TYPE: PRT
<213> ORGANISM: Mastotermes darwiniensis hindgut symbiont sp.

<400> SEQUENCE: 63

Met Ile Val Val Phe Val Ile Gly Ala Leu Cys Lys Asp Tyr Ser Gly
1               5                   10                  15

Asn Gly Gln Thr Thr Arg Tyr Trp Asp Cys Cys Lys Pro Ser Cys Ser
            20                  25                  30

Trp Ser Lys Lys Ala Gln Val Ser His Val Val Asn Ser Cys Thr Ala
        35                  40                  45

Thr Gly Ser His Asp Thr Thr Val Asp Leu Lys Ser Gly Cys Asp Gly
    50                  55                  60

Gly Pro Ser Tyr Val Cys Val Asp Gln Ala Pro Trp Ala Val Asn Ser
65                  70                  75                  80

Ser Tyr Phe Met Gly Thr Ala Ala Ala Leu Ser Gly Gly Ser Glu
                85                  90                  95

Ser Asp Leu Cys Cys Arg Cys Phe Glu Leu Thr Phe Thr Ser Gly Gln

```
            100                 105                 110
Pro Asn Gly Lys Lys Met Leu Val Gln Val Thr Asn Thr Gly Ser Asp
            115                 120                 125

Leu Ser Gly Asn Gln Phe Asp Leu Leu Ile Pro Gly Gly Val Gly
        130                 135                 140

Ile Phe Asp Gly Cys Ser Arg Gln Tyr Pro Gly Gly Asn Tyr Asp Trp
145                 150                 155                 160

Gly Gln Arg Tyr Gly Gly Val Thr Ser Lys Ala Gly Cys Ala Lys Ile
                165                 170                 175

Pro Ala Glu Leu Lys Ala Gly Cys Glu Phe Arg Phe Asp Tyr Ile Gly
            180                 185                 190

Asp Asn Pro Ser Val Ser Phe Lys Ser Val His Cys Pro Asp Thr Ile
        195                 200                 205

Thr Ser Lys Thr Asn Cys Arg Arg Asn Asp Asp Asn
        210                 215                 220

<210> SEQ ID NO 64
<211> LENGTH: 220
<212> TYPE: PRT
<213> ORGANISM: Mastotermes darwiniensis hindgut symbiont sp.

<400> SEQUENCE: 64

Met Ile Val Val Phe Val Ile Gly Ala Leu Cys Lys Asp Tyr Ser Gly
1               5                   10                  15

Ser Gly Lys Thr Thr Arg Tyr Trp Asp Cys Cys Lys Pro Ser Cys Ser
            20                  25                  30

Trp Ser Lys Ala Gln Val Ser His Val Val Asn Ser Cys Thr Ala
        35                  40                  45

Ser Gly Gln His Asp Thr Thr Val Asp Leu Lys Ser Gly Cys Asp Gly
    50                  55                  60

Gly Pro Ser Tyr Val Cys Val Asp Gln Ala Pro Trp Ala Val Asn Ser
65                  70                  75                  80

Ser Tyr Phe Met Gly Thr Ala Ala Ala Leu Ser Gly Gly Ser Glu
                85                  90                  95

Ser Asp Leu Cys Cys Arg Cys Phe Glu Leu Thr Phe Thr Ser Gly Gln
            100                 105                 110

Ser Asn Gly Lys Lys Met Leu Val Gln Ile Thr Asn Thr Gly Ser Asp
            115                 120                 125

Leu Ser Gly Asn Gln Phe Asp Leu Leu Ile Pro Gly Gly Val Gly
        130                 135                 140

Ile Phe Asp Gly Cys Ser Arg Gln Tyr Pro Gly Gly Asn Tyr Asp Trp
145                 150                 155                 160

Gly Gln Arg Tyr Gly Gly Val Thr Ser Lys Ala Gly Cys Ala Lys Ile
                165                 170                 175

Pro Ala Glu Leu Lys Ala Gly Cys Glu Phe Arg Phe Asp Tyr Ile Gly
            180                 185                 190

Asp Asn Pro Ser Val Ser Phe Lys Ser Val His Cys Pro Asp Thr Ile
        195                 200                 205

Thr Ser Lys Thr Asn Cys Arg Arg Asn Asp Asp Gln
        210                 215                 220

<210> SEQ ID NO 65
<211> LENGTH: 614
<212> TYPE: PRT
<213> ORGANISM: Pichia pastoris GS115
```

<400> SEQUENCE: 65

```
Met Ser Thr Leu Thr Leu Leu Ala Val Leu Leu Ser Leu Gln Asn Ser
1               5                   10                  15

Ala Leu Ala Ala Gln Ala Glu Thr Ala Ser Leu Tyr His Gln Cys Gly
            20                  25                  30

Gly Ala Asn Trp Glu Gly Ala Thr Gln Cys Ile Ser Gly Ala Tyr Cys
        35                  40                  45

Gln Ser Gln Asn Pro Tyr Tyr Tyr Gln Cys Val Ala Thr Ser Trp Gly
    50                  55                  60

Tyr Tyr Thr Asn Thr Ser Ile Ser Ser Thr Ala Thr Leu Pro Ser Ser
65                  70                  75                  80

Ser Thr Thr Val Ser Pro Thr Ser Ser Val Val Pro Thr Gly Leu Val
                85                  90                  95

Ser Pro Leu Tyr Gly Gln Cys Gly Gly Gln Asn Trp Asn Gly Ala Thr
            100                 105                 110

Ser Cys Ala Gln Gly Ser Tyr Cys Lys Tyr Met Asn Asn Tyr Tyr Phe
        115                 120                 125

Gln Cys Val Pro Glu Ala Asp Gly Asn Pro Ala Glu Ile Ser Thr Phe
    130                 135                 140

Ser Glu Asn Gly Glu Ile Ile Val Thr Ala Ile Ala Pro Thr Trp
145                 150                 155                 160

Ala Gln Cys Gly Gly His Gly Tyr Tyr Gly Pro Thr Lys Cys Gln Val
                165                 170                 175

Gly Thr Ser Cys Arg Glu Leu Asn Ala Trp Tyr Tyr Gln Cys Ile Pro
            180                 185                 190

Asp Asp His Thr Asp Ala Ser Thr Thr Thr Leu Asp Pro Thr Ser Ser
        195                 200                 205

Phe Val Ser Thr Thr Ser Leu Ser Thr Leu Pro Ala Ser Ser Glu Thr
    210                 215                 220

Thr Ile Val Thr Pro Thr Ser Ile Ala Ala Glu Gln Val Pro Leu Trp
225                 230                 235                 240

Gly Gln Cys Gly Gly Ile Gly Tyr Thr Gly Ser Thr Ile Cys Glu Gln
                245                 250                 255

Gly Ser Cys Val Tyr Leu Asn Asp Trp Tyr Tyr Gln Cys Leu Ile Ser
            260                 265                 270

Asp Gln Gly Thr Ala Ser Thr Thr Ser Ala Thr Thr Ser Ile Thr Ser
        275                 280                 285

Phe Asn Val Ser Ser Ser Ser Glu Thr Thr Val Ile Ala Pro Thr Ser
    290                 295                 300

Ile Ser Thr Glu Asp Val Pro Leu Trp Gly Gln Cys Gly Gly Ile Gly
305                 310                 315                 320

Tyr Thr Gly Ser Thr Thr Cys Ser Gln Gly Ser Cys Val Tyr Leu Asn
                325                 330                 335

Asp Trp Tyr Phe Gln Cys Leu Pro Glu Glu Thr Thr Ser Ser Thr
            340                 345                 350

Ser Ser Ser Ser Ser Ser Ser Ser Ser Thr Ser Ser Ala Ser Ser
        355                 360                 365

Thr Ser Ser Thr Ser Ser Thr Ser Ser Thr Ser Ser Ser Ser Ser
    370                 375                 380

Thr Ser Ser Ser Ser Ile Pro Thr Ser Thr Ser Ser Gly Asp Phe
385                 390                 395                 400

Glu Thr Ile Pro Asn Gly Phe Ser Gly Thr Gly Arg Thr Thr Arg Tyr
                405                 410                 415
```

-continued

Trp Asp Cys Cys Lys Pro Ser Cys Ser Trp Pro Gly Lys Ser Asn Ser
                420                 425                 430

Val Thr Gly Pro Val Arg Ser Cys Gly Val Ser Gly Asn Val Leu Asp
            435                 440                 445

Ala Asn Ala Gln Ser Gly Cys Ile Gly Gly Glu Ala Phe Thr Cys Asp
450                 455                 460

Glu Gln Gln Pro Trp Ser Ile Asn Asp Asp Leu Ala Tyr Gly Phe Ala
465                 470                 475                 480

Ala Ala Ser Leu Ala Gly Gly Ser Glu Asp Ser Ser Cys Cys Thr Cys
                485                 490                 495

Met Lys Leu Thr Phe Thr Ser Ser Ile Ala Gly Lys Thr Met Ile
                500                 505                 510

Val Gln Leu Thr Asn Thr Gly Ala Asp Leu Gly Ser Asn His Phe Asp
            515                 520                 525

Ile Ala Leu Pro Gly Gly Leu Gly Ile Phe Thr Glu Gly Cys Ser
530                 535                 540

Ser Gln Phe Gly Ser Gly Tyr Gln Trp Gly Asn Gln Tyr Gly Gly Ile
545                 550                 555                 560

Ser Ser Leu Ala Glu Cys Asp Gly Leu Pro Ser Glu Leu Gln Pro Gly
                565                 570                 575

Cys Gln Phe Arg Phe Gly Trp Phe Glu Asn Ala Asp Asn Pro Ser Val
            580                 585                 590

Glu Phe Glu Gln Val Ser Cys Pro Pro Glu Ile Thr Ser Ile Thr Gly
            595                 600                 605

Cys Ala Arg Thr Asp Glu
            610

<210> SEQ ID NO 66
<211> LENGTH: 410
<212> TYPE: PRT
<213> ORGANISM: Piromyces equi

<400> SEQUENCE: 66

Met Arg Leu Ala Leu Thr Ser Cys Ile Ala Leu Ala Ala Ser Ile Ala
1               5                   10                  15

Lys Val Ser Ala Ala Cys Trp Ala Gln Ser Gln Gly Tyr Asn Cys Cys
                20                  25                  30

Asn Asn Pro Ser Ser Thr Lys Val Glu Tyr Thr Asp Ala Ser Gly Gln
            35                  40                  45

Trp Gly Val Gln Asn Gly Gln Trp Cys Gly Ile Asp Tyr Ser Tyr Gly
    50                  55                  60

Gln Asn Gln Gly Asn Glu Ser Cys Thr Gly Asn Gly Ser Tyr Pro Cys
65                  70                  75                  80

Cys Asn Thr Cys Gln Ala Thr Tyr Thr Asp Gly Asp Gly Asp Trp Ala
                85                  90                  95

Phe Glu Asn Gly Asn Trp Cys Gly Ile Lys Asn Ser Cys Lys Gln Gln
            100                 105                 110

Pro Gln Asn Asn Asn Gln Cys Thr Gly Asn Gly Ala Tyr Arg Cys Cys
        115                 120                 125

Asn Thr Cys Gln Ala Thr Tyr Thr Asp Asn Glu Gly Lys Trp Ala Phe
        130                 135                 140

Glu Asn Gly Asp Trp Cys Gly Ile Lys Tyr Ser Cys Pro Ser Gln Gln
145                 150                 155                 160

Val Thr Thr Thr Thr Thr Arg Arg Thr Thr Thr Thr Gln Gln Gln

-continued

```
                165                 170                 175
Gln Pro Thr Gly Ser Gly Gly Asn Ser Asn Val Pro Leu Asn Pro Pro
            180                 185                 190

Asp Phe Ser Gly Gln Thr Gly Lys Thr Thr Arg Tyr Trp Asp Cys Cys
            195                 200                 205

Leu Ala Ser Cys Ser Trp Gln Glu Asn Cys Lys Asn Asp Gly Ala Gln
            210                 215                 220

Gly Val Val Arg Ser Cys Asn Val Asp Gly Ile Thr Pro Phe Thr Asp
225                 230                 235                 240

Leu Ser Asn Leu Trp Arg Val Lys Ser Gly Cys Asn Gly Gly Ser Val
                245                 250                 255

Tyr Met Cys Asn Asp Gln Gln Pro Trp Ala Ile Asn Asp Asn Val Ala
                260                 265                 270

Tyr Gly Phe Val Ala Ser His Glu Lys Cys Cys Thr Cys Gln Arg Leu
                275                 280                 285

Lys Phe Thr Ser Gly Pro Ile Ala Gly Lys Gln Met Ile Val Gln Thr
                290                 295                 300

Thr Asn Thr Gly Gly Asp Leu Ser Ser Asn His Phe Asp Ile Gln Met
305                 310                 315                 320

Pro Gly Gly Gly Phe Gly Ile Phe Asp Gly Cys Thr Ser Gln Phe Gly
                325                 330                 335

Gly Ser Tyr Gln Trp Gly Glu Arg Tyr Gly Gly Ile Ser Ser Ala Ser
                340                 345                 350

Gln Cys Ala Asn Leu Pro Pro Gln Leu Lys Ala Gly Cys Glu Trp Arg
                355                 360                 365

Phe Asn Trp Phe Lys Asn Ala Asp Asn Pro Ala Val Val Phe Glu Arg
                370                 375                 380

Val Gln Cys Pro Lys Glu Leu Thr Glu Ile Thr Gly Cys Val Pro Gly
385                 390                 395                 400

Asp Asp Ala Ser Ala Lys Lys Leu Pro Trp
                405                 410

<210> SEQ ID NO 67
<211> LENGTH: 237
<212> TYPE: PRT
<213> ORGANISM: Apriona germari

<400> SEQUENCE: 67

Met Lys Val Phe Val Ala Ile Leu Ala Val Phe Cys Thr Phe Glu Val
1               5                   10                  15

Ser Leu Ser Lys Val Tyr Asn Leu Asn Lys Val Pro Tyr Gly Ile Ser
                20                  25                  30

Gly Ser Gly Thr Thr Thr Arg Tyr Trp Asp Cys Cys Lys Pro Ser Cys
            35                  40                  45

Gly Trp Val Glu Asn Leu Ala Lys Glu Gly Thr Pro Val Ala Thr Cys
50                  55                  60

Ser Ala Asp Gly Ser Thr Thr Val Ala Ala Ser Val Lys Ser Ser Cys
65                  70                  75                  80

Val Gly Gly Thr Ser Tyr Met Cys Ser Asn Gln Gln Pro Lys Ser Val
                85                  90                  95

Asn Ser Thr Phe Ala Leu Gly Phe Val Ala Ser Phe Thr Gly Gly
            100                 105                 110

Ala Asp Thr Asn Tyr Cys Cys Ala Cys Ile Lys Leu Thr Phe Gln Asp
            115                 120                 125
```

```
Ala Leu Gln Gly Lys Thr Met Val Gln Val Thr Asn Thr Gly Gly
    130                 135                 140

Asp Leu Gly Ser Asn Gln Phe Asp Ile Ala Ile Pro Gly Gly Val
145                 150                 155                 160

Gly Ile Phe Thr Asp Gly Cys Ser Ser Gln Trp Gly Thr Pro Ser Asn
                165                 170                 175

Gly Trp Gly Asp Gln Tyr Trp Val Trp Gly Ser Glu Ala Asp Cys
            180                 185                 190

Ala Gln Leu Pro Ser Asp Leu Gln Glu Gly Cys Lys Phe Arg Phe Glu
            195                 200                 205

Phe Met Glu Gly Ala Ser Asn Pro Gly Val Thr Phe Glu Gln Val Asp
210                 215                 220

Cys Pro Ser Glu Leu Val Ser Ile Thr Gly Cys Asn Tyr
225                 230                 235
```

<210> SEQ ID NO 68
<211> LENGTH: 239
<212> TYPE: PRT
<213> ORGANISM: Apriona germari

<400> SEQUENCE: 68

```
Met Lys Val Leu Leu Ala Val Val Ala Val Leu Cys Thr Phe Glu Ala
1               5                   10                  15

Ser Leu Ser Gln Asp Tyr His Val Thr Pro Leu Val Gly Gly Val Ser
            20                  25                  30

Gly Thr Gly Lys Thr Thr Arg Tyr Trp Asp Cys Cys Lys Pro Ser Cys
        35                  40                  45

Ser Trp Lys Ala Asn Leu Lys Ser Lys Ser Gly Lys Pro Val Glu Ala
50                  55                  60

Cys Ala Ala Asp Gly Lys Thr Val Val Lys Ser Thr Lys Ser Ala
65                  70                  75                  80

Cys Glu Glu Gly Ala Gly Ala Tyr Met Cys Ser Asp Gln Gln Pro Lys
            85                  90                  95

Val Val Asn Ser Thr Phe Ala Leu Gly Tyr Val Ala Ala Ser Phe Thr
        100                 105                 110

Gly Gly Ile Asp Val Asn Met Cys Cys Ala Cys Leu Arg Leu Lys Phe
    115                 120                 125

Gln Gly Asp Leu Ser Gly Lys Gln Met Ile Val Gln Val Thr Asn Thr
130                 135                 140

Gly Ser Asp Leu Gly Ser Asn Gln Phe Asp Ile Ala Ile Pro Gly Gly
145                 150                 155                 160

Gly Val Gly Ile Phe Thr Lys Gly Cys Ser Ser Gln Trp Gly Thr Pro
                165                 170                 175

Ser Asn Gly Trp Gly Asp Gln Tyr Gly Gly Val Ser Ser Glu Ser Gln
            180                 185                 190

Cys Ser Gln Leu Pro Ser Ser Leu Arg Glu Gly Cys Lys Phe Arg Phe
        195                 200                 205

Thr Phe Met Lys Ser Val Ser Asn Pro Ala Val Thr Phe Glu Gln Val
210                 215                 220

Ser Cys Pro Ser Glu Ile Val Ser Ala Ser Gly Cys Asn Tyr Ser
225                 230                 235
```

<210> SEQ ID NO 69
<211> LENGTH: 271
<212> TYPE: PRT
<213> ORGANISM: Alternaria alternata

<400> SEQUENCE: 69

```
Met Pro Gln His Leu Arg Asn Ile Ala Leu Thr Ile Glu Phe Phe Ala
1               5                   10                  15

Val Leu Ala Arg Cys Ala His Leu Asn Tyr Thr Gly Glu Ala Val Thr
            20                  25                  30

Thr Arg Phe Trp Asp Cys Cys Lys Pro Ser Cys Gly Trp Asn Gly Lys
        35                  40                  45

Ala Gln Phe Ser Arg Pro Val Glu Ser Cys Thr Ala Asp Asp Lys Pro
    50                  55                  60

Thr Asp Ile Ala Ala Gly Thr Gly Cys Asn Ser Gly Ser Ala Phe Gln
65                  70                  75                  80

Cys Ser Asn Gln Gln Pro Trp Ala Ile Asn Asp Thr Leu Ser Tyr Gly
                85                  90                  95

Tyr Ala Gly Val Tyr Ile Thr Pro Asp Leu Thr His Gly Gly Ile Glu
            100                 105                 110

Asp Ala Trp Cys Cys Ala Cys Tyr Gln Leu Asn Phe Thr Ser Glu Pro
        115                 120                 125

Leu Ile Gly Lys Ser Met Ile Val Gln Ala Ser Asn Thr Ala Tyr Asp
    130                 135                 140

Val Thr Asn Ala Asn Arg Phe Ser Leu Ala Val Pro Gly Gly Asn Thr
145                 150                 155                 160

Thr Ser Thr Asn Ala Cys Ala Gln Gln Tyr Gly Val Ser Gln Ser Val
                165                 170                 175

Phe Gly Glu Asn Met Ala Gly Val Lys Ser Ile Asp Asp Cys Gln Asn
            180                 185                 190

Leu Pro Glu Asn Leu Arg Ala Gly Cys Glu Trp Arg Phe Asp Trp Phe
        195                 200                 205

Lys Asn Ala Ser Phe Pro Ser Ala Asn Phe Lys Arg Val Val Cys Pro
    210                 215                 220

Ser Glu Ile Thr Ala Lys Thr Asn Cys Ile Arg Asn Asp Asp Lys Val
225                 230                 235                 240

Leu Ala Gly Glu Ala Ser Ser Ala Gln Ser Leu Thr Pro Ser Ser Ser
                245                 250                 255

Thr Met Ala Phe Phe Ala Val Ile Ile Leu Gly Leu Ile Ser Ile
            260                 265                 270
```

<210> SEQ ID NO 70
<211> LENGTH: 242
<212> TYPE: PRT
<213> ORGANISM: Phaedon cochleariae

<400> SEQUENCE: 70

```
Met Gln Val Ile Val Leu Pro Leu Val Phe Leu Ala Thr Phe Ala Thr
1               5                   10                  15

Ser Gly Ser Leu Ala Ala Pro Asp Ala Ser Pro Glu Ile Val Pro Val
            20                  25                  30

Asp Gly Gly Leu Ser Gly Tyr Gly Thr Thr Thr Arg Tyr Trp Asp Cys
        35                  40                  45

Cys Lys Pro Ser Cys Ala Trp Lys Glu Asn Ile Asn Thr Pro Thr Met
    50                  55                  60

Thr Pro Val Gln Thr Cys Ala Ile Asp Gly Asn Thr Val Val Asn Ala
65                  70                  75                  80

Ser Val Gln Ser Gly Cys Ile Gly Gly Ser Ser Tyr Met Cys Ser Asn
                85                  90                  95
```

```
Gln Gln Ala Phe Val Val Asn Ser Thr Leu Ala Phe Gly Phe Ala Ala
            100                 105                 110

Gly Ser Phe Thr Gly Gly Val Asp Asn Asn Leu Cys Cys Ser Cys Met
            115                 120                 125

Leu Leu Thr Phe Gln Gly Gln Leu Ala Gly Lys Gln Phe Leu Val Gln
        130                 135                 140

Ile Thr Asn Thr Gly Gly Asp Leu Gly Ser Thr Ser Ser Ile Trp Pro
145                 150                 155                 160

Phe Pro Gly Gly Gly Val Gly Ile Phe Thr Gln Gly Cys His Asp Gln
                165                 170                 175

Trp Thr Pro Arg Gly Ala Ala Gly Gly Asp Gln Tyr Gly Gly Val Tyr
            180                 185                 190

Ser Val Glu Gln Cys Ser Asp Leu Pro Glu Val Leu Gln Pro Gly Cys
            195                 200                 205

Arg Phe Arg Phe Glu Phe Leu Glu Asn Val Ser Asn Pro Gln Val Ser
        210                 215                 220

Phe Gln Gln Val Gln Cys Pro Ala Glu Ile Val Ala Ile Ser Asn Cys
225                 230                 235                 240

Ala Leu

<210> SEQ ID NO 71
<211> LENGTH: 222
<212> TYPE: PRT
<213> ORGANISM: Talaromyces emersonii

<400> SEQUENCE: 71

Met Asn Val Arg Ala Val Val Ser Val Ser Ala Phe Leu Leu Thr Pro
1               5                   10                  15

Leu Ala Ser Ala Leu Thr Gly Thr Thr Thr Thr Thr Trp Asp Cys Cys
            20                  25                  30

Lys Pro Ala Cys Ser Trp Thr Gln Asn Ala Gln Ala Gly Gly Ala Ser
        35                  40                  45

Gly Thr Val Ala Thr Cys Asn Ile Asn Asn Gln Val Leu Ser Asn Gly
    50                  55                  60

Ala Ser Ala Pro Ser Ala Cys Gln Gly Gly Asp Ala Tyr Ser Cys Ser
65                  70                  75                  80

Asp Phe Gln Pro Ile Ile Ile Ser Asp Thr Leu Ser Tyr Gly Phe Ala
                85                  90                  95

Gly Asn Trp Glu Thr Ser Asn Cys Cys Lys Cys Phe Gln Phe Thr Trp
            100                 105                 110

Thr Ser Gly Ala Gly Ala Gly Lys Ser Met Ile Val Gln Val Val Asn
        115                 120                 125

Ser Gly Gly Val Ser Thr Gly Asp Phe Asp Ile Tyr Thr Pro Gly Gly
    130                 135                 140

Gly Val Gly Asp Tyr Asn Ala Cys Thr Ser Gln Tyr Gly Ala Pro Pro
145                 150                 155                 160

Gln Gly Trp Gly Ala Gln Tyr Gly Gly Val Ser Ser Asp Ala Glu Cys
                165                 170                 175

Asp Gln Leu Pro Ser Ile Leu Gln Pro Gly Cys His Trp Arg Phe Glu
            180                 185                 190

Trp Ala Gly Gly Gly Ile Asn Gly Trp Thr Thr Glu Tyr Glu Glu Val
        195                 200                 205

Asp Cys Pro Ser Gln Leu Thr Ser Ile Ser Gly Cys Tyr Pro
    210                 215                 220
```

```
<210> SEQ ID NO 72
<211> LENGTH: 393
<212> TYPE: PRT
<213> ORGANISM: Ustilago maydis

<400> SEQUENCE: 72

Met Ala Phe Lys Leu Asn Ile Gly Leu Leu Ala Leu Ser Leu Ser Leu
1               5                   10                  15

Ser Leu Val His Leu Asp Gly Val Arg Ala Gly Met Ala Thr Arg Tyr
            20                  25                  30

Trp Asp Cys Cys Leu Ala Ser Ala Ser Trp Glu Gly Lys Ala Pro Val
        35                  40                  45

Tyr Ala Pro Val Asp Ala Cys Lys Ala Asp Gly Val Thr Leu Ile Asp
    50                  55                  60

Ser Lys Lys Asp Pro Ser Gly Gln Ser Gly Cys Asn Gly Gly Asn Lys
65                  70                  75                  80

Phe Met Cys Ser Cys Met Gln Pro Phe Asp Asp Glu Thr Asp Pro Thr
                85                  90                  95

Leu Ala Phe Gly Phe Gly Ala Phe Thr Thr Gly Gln Glu Ser Asp Thr
            100                 105                 110

Asp Cys Ala Cys Phe Tyr Ala Glu Phe Glu His Asp Ala Gln Gly Lys
        115                 120                 125

Ala Met Lys Arg Asn Lys Leu Ile Phe Gln Val Thr Asn Val Gly Gly
    130                 135                 140

Asp Val Gln Ser Gln Asn Phe Asp Phe Gln Ile Pro Gly Gly Gly Leu
145                 150                 155                 160

Gly Ala Phe Pro Lys Gly Cys Pro Ala Gln Trp Gly Val Glu Ala Ser
                165                 170                 175

Leu Trp Gly Asp Gln Tyr Gly Gly Val Lys Ser Ala Thr Glu Cys Ser
            180                 185                 190

Lys Leu Pro Lys Pro Leu Gln Glu Gly Cys Lys Trp Arg Phe Ser Glu
        195                 200                 205

Trp Gly Asp Asn Pro Val Leu Lys Gly Ser Pro Lys Arg Val Lys Cys
    210                 215                 220

Pro Lys Ser Leu Ile Asp Arg Ser Gly Cys Gln Arg Lys Asp Asp Asn
225                 230                 235                 240

Thr Ile Ser Pro Tyr Ser Gly Lys Val Asp Ser Ala Asn Thr Ala Ala
                245                 250                 255

Pro Ala Gln Tyr Lys Arg Asp Arg Ser Val Cys Leu Ala Gly Gly Lys
            260                 265                 270

Lys Gly Lys Ser Ala Ala Gly Val Asp Gly Ser Gly Asp Ala Ser
        275                 280                 285

Gly Gly Ala Asp Ala Ser Gly Ala Gly Ala Ala Glu Gly Ser Gln
    290                 295                 300

Gly Gln Pro Glu Gly Tyr Gly Gln Pro Ser Gly Gly Asn Asp Gln Gly
305                 310                 315                 320

Ser Ser Asn Gly Asp Ala Thr Thr Gly Ala Gly Ser Gly Ser Gly Ser
                325                 330                 335

Asp Ser Gly Ser Thr Ala Asn Gly Ser Gly Ser Gly Ala Pro Thr Ser
            340                 345                 350

Gly Ser Asp Gly Ser Ala Val Ala Pro Pro Ser Gly Gly Ser Asn Pro
        355                 360                 365
```

```
Gly Ala Ala Gln Gly Gly Gln Gly Gly Ala Gln Pro Gly Pro Ser Gly
    370                 375                 380

Gly His Lys Lys Cys His Lys Lys His
385                 390
```